US012605480B2

(12) United States Patent
Freedman et al.

(10) Patent No.: US 12,605,480 B2
(45) Date of Patent: Apr. 21, 2026

(54) TOUGH GEL-BASED DRUG DELIVERY COMPOSITIONS AND METHODS THEREOF

(71) Applicant: President and Fellows of Harvard College, Cambridge, MA (US)

(72) Inventors: Benjamin Ross Freedman, Brookline, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 738 days.

(21) Appl. No.: 17/761,193

(22) PCT Filed: Sep. 18, 2020

(86) PCT No.: PCT/US2020/051427

§ 371 (c)(1),
(2) Date: Mar. 17, 2022

(87) PCT Pub. No.: WO2021/055703

PCT Pub. Date: Mar. 25, 2021

(65) Prior Publication Data

US 2024/0016972 A1 Jan. 18, 2024

Related U.S. Application Data

(60) Provisional application No. 62/903,315, filed on Sep. 20, 2019.

(51) Int. Cl.
*A61L 24/00* (2006.01)
*A61L 24/02* (2006.01)

(52) U.S. Cl.
CPC ....... *A61L 24/0089* (2013.01); *A61L 24/0015* (2013.01); *A61L 24/0031* (2013.01); *A61L 24/02* (2013.01); *A61L 2300/222* (2013.01)

(58) Field of Classification Search
CPC ............. A61L 24/0089; A61L 24/0015; A61L 24/0031; A61L 24/02; A61L 2300/222
See application file for complete search history.

(56) References Cited

U.S. PATENT DOCUMENTS

| | | |
|---|---|---|
| 3,611,732 A | 10/1971 | Epstein |
| 4,768,523 A | 9/1988 | Cahalan et al. |
| 5,334,640 A | 8/1994 | Desai et al. |
| 5,563,186 A | 10/1996 | Thompson |
| 5,620,702 A | 4/1997 | Podell et al. |
| 5,644,049 A | 7/1997 | Giusti et al. |
| 6,030,634 A | 2/2000 | Wu et al. |
| 6,271,278 B1 | 8/2001 | Park et al. |
| 6,352,707 B1 | 3/2002 | Usala |
| 6,960,617 B2 | 11/2005 | Omidian et al. |
| 8,293,510 B2 | 10/2012 | Detamore et al. |
| 9,387,276 B2 | 7/2016 | Sun et al. |
| 9,987,221 B2 | 6/2018 | Richard |
| 10,383,980 B2 | 8/2019 | Sun et al. |

| | | |
|---|---|---|
| 11,033,658 B2 | 6/2021 | Sun et al. |
| 2003/0232895 A1 | 12/2003 | Omidian et al. |
| 2008/0139694 A1 | 6/2008 | Ratcliffe |
| 2008/0317818 A1 | 12/2008 | Griffith et al. |
| 2010/0021416 A1 | 1/2010 | Lichter et al. |
| 2010/0055184 A1 | 3/2010 | Zeitels et al. |
| 2010/0234784 A1 | 9/2010 | Hartwell |
| 2012/0009223 A1 | 1/2012 | Wenguang et al. |
| 2013/0172419 A1 | 7/2013 | Saxena et al. |
| 2014/0295553 A1 | 10/2014 | Du et al. |
| 2015/0038613 A1 | 2/2015 | Sun et al. |
| 2017/0197392 A1 | 7/2017 | Illeperuma et al. |
| 2017/0202789 A1* | 7/2017 | Sexton ................. A61K 31/519 |
| 2019/0091367 A1* | 3/2019 | Li ......................... A61K 9/7046 |
| 2021/0338577 A1 | 11/2021 | Freedman et al. |
| 2021/0353830 A1 | 11/2021 | Sun et al. |

FOREIGN PATENT DOCUMENTS

| | | | |
|---|---|---|---|
| FR | 2938544 A1 | 5/2010 |
| JP | 2005-110537 A | 4/2005 |
| JP | 2009-507110 A | 2/2009 |
| JP | 2009-120855 A | 6/2009 |
| KR | 20100096676 A | 9/2010 |
| WO | 1998/012228 A1 | 3/1998 |
| WO | 1998/52543 A1 | 11/1998 |
| WO | 2003/089506 A1 | 10/2003 |
| WO | 2007/028258 A2 | 3/2007 |
| WO | 2009/134414 A2 | 11/2009 |

(Continued)

OTHER PUBLICATIONS

Aguzzi et al., Use of clays as drug delivery systems: Possibilities and limitations. Applied Clay Science. 2007;36:22-36.

Bakarich et al., Recovery from applied strain in interpenetrating polymer network hydrogels with ionic and covalent cross-links. Soft Matter. Sep. 2012;8:9985-8.

Braun et al., The relative contribution of calcium, zinc and oxidation-based cross-links to the stiffness of Arion subfuscus glue. J Exp Biol. Apr. 15, 2013;216(Pt 8):1475-83.

Choi et al., Depolymerization of Alginates by Hydrogen Peroxide/Ultrasonic Irradiation. Polymer(Korea). 2011;35(5):444-450.

Cohen et al., Gelatin-alginate novel tissue adhesives and their formulation-strength effects. Acta Biomater. Nov. 2013;9(11):9004-11.

(Continued)

*Primary Examiner* — Shirley V Gembeh

(74) *Attorney, Agent, or Firm* — McCarter & English, LLP; Maria Laccotripe Zacharakis; Wei Song

(57) ABSTRACT

Described herein are tough gel compositions that comprise an interpenetrating networks (IPN) hydrogel. The IPN hydrogel comprises a first polymer network (covalently crosslinked) and a second polymer network (ionically cross-linked), at least one therapeutic agent, and a clay material. The tough gel compositions may further include an adhesive polymer layer attached to the IPN hydrogel. Methods of use of these compositions, such as for extended release drug delivery, are also described.

17 Claims, 59 Drawing Sheets

(56) References Cited

FOREIGN PATENT DOCUMENTS

| WO | 2010/093528 A2 | 8/2010 | | |
| WO | 2013/025763 A2 | 2/2013 | | |
| WO | 2013/103956 A1 | 7/2013 | | |
| WO | 2015/143078 A1 | 9/2015 | | |
| WO | 2015/154078 A1 | 10/2015 | | |
| WO | 2016/007429 A1 | 1/2016 | | |
| WO | WO 2016/100355 * | 6/2016 | | |
| WO | WO-2016100355 A1 * | 6/2016 | .......... | A61F 9/0008 |
| WO | 2017/165490 A1 | 9/2017 | | |
| WO | 2019/203974 A1 | 10/2019 | | |
| WO | 2020/077173 A1 | 4/2020 | | |

OTHER PUBLICATIONS

Duan et al., Double-network carboxymethyl chitosan grafting polyacrylamide/alginate hydrogel compositions adapted to achieve high stretchable properties. J Mol Genet Med. 2015;9(3):1-3.

Farahmandghavi et al., Silicone matrices loaded with levonorgestrel particles: Impact of the particle size on drug release. Journal of Drug Delivery Science and Technology. 2019;49:132-142.

George et al., Polyionic hydrocolloids for the intestinal delivery of protein drugs: alginate and chitosan—a review. J Control Release. Aug. 10, 2006;114(1):1-14.

Gilles et al., Stability of water-soluble carbodiimides in aqueous solution. Anal Biochem. Feb. 1, 1990;184(2):244-8.

Haug et al., The Effect of Divalent Metals on the Properties of Alginate Solutions. II. Comparison of Different Metal Ions. Acta Chemica Scandinavica. 1965;19;341-51.

Hong et al., 3D Printing of Highly Stretchable and Tough Hydrogels into Complex, Cellularized Structures. Adv Mater. Jul. 15, 2015;27(27):4035-40.

Ishihara et al., Photocrosslinkable chitosan as a dressing for wound occlusion and accelerator in healing process. Biomaterials. Feb. 2002;23(3):833-40.

Kong et al., Controlling rigidity and degradation of alginate hydrogels via molecular weight districution. Biomacromolecules. 2004;5:1720-7.

Leo et al., Effects of sterilization treatments on some properties of alginate solutions and gels. Biotechnol Prog. Jan.-Feb. 1990;6(1):51-3.

Li et al., Hybrid Hydrogels with Extremely High Stiffness and Toughness. ACS Macro Lett. 2014;3:520-523.

Li et al., Novel Poly(N-isopropylacrylamide)/Clay/Poly(acrylamide) IPN Hydrogels with the Response Rate and Drug Release Controlled by Clay Content. J Polym Sci Part B: Polym Phys. 2009;47:96-106.

Li et al., Tough adhesives for diverse wet surfaces. Science. Jul. 28, 2017;357(6349):378-381.

Naficy et al., Mechanical properties of interpenetrating polymer network hydrogels based on hybrid ionically and covalently cross-linked networks. J Appl Polym Sci. Nov. 2013;130(4):2504-13.

Nakajima et al., Mechanism of amide formation by carbodiimide for bioconjugation in aqueous media. Bioconjug Chem. Jan.-Feb. 1995;6(1):123-30.

Omidian et al., Elastic, superporous hydrogel hybrids of polyacrylamide and sodium alginate. Macromol Biosci. Sep. 15, 2006;6(9):703-10.

Park et al., Types of Biodegradable Hydrogels. Biodegradable Hydrogels for Drug Delivery. Technomic Publishing Company, Inc., Lancaster, Pennsylvania. Chapter 3, pp. 35-66, (1993).

Picart et al., Controlled degradability of polysaccharide multilayer films in vitro and in vivo. Adv Funct Mater. 2005;15:1771-80.

Shariatinia et al., Carboxymethyl chitosan: Properties and biomedical applications. Int J Biol Macromol. Dec. 2018;120(Pt B):1406-1419.

Sun et al., Highly stretchable and tough hydrogels. Nature. Sep. 6, 2012;489(7414):133-6.

Tsujino et al., A new unsaturated uronide isolated from alginase hydrolysate. Nature. Dec. 9, 1961;192:970-1.

Yuk et al., Tough bonding of hydrogels to diverse non-porous surfaces. Nat Mater. Feb. 2016;15(2):190-6.

U.S. Appl. No. 14/370,451, filed Jul. 2, 2014, U.S. Pat. No. 9,387,276, Issued.

U.S. Appl. No. 15/172,549, filed Jun. 3, 2016, U.S. Pat. No. 10,383,980, Issued.

U.S. Appl. No. 16/459,907, filed Jul. 2, 2019, U.S. Pat. No. 11,033,658, Issued.

U.S. Appl. No. 17/320,726, filed May 14, 2021, 2021-0353830, Abandoned.

U.S. Appl. No. 16/086,631,filed Sep. 20, 2018, 2019-0091367, Allowed.

U.S. Appl. No. 17/283,412, filed Apr. 7, 2021, 2021-0338577, Published.

International Search Report and Written Opinion for Application No. PCT/US2020/051427, dated Feb. 4, 2021, 11 pages.

Liu, Application principle of polymer materials in pharmaceutical formulation. Pharmaceutical Polymer Materials, 2nd Edition. Chemical Industry Press. Yao Risheng (Ed.). pp. 69-70, Mar. 2008.

* cited by examiner 0.1mg/ml
(~1.1μm²)

1mg/ml
(~58μm²)

10mg/ml
(~491μm²)

200μm

CORT

Time 0

Time X

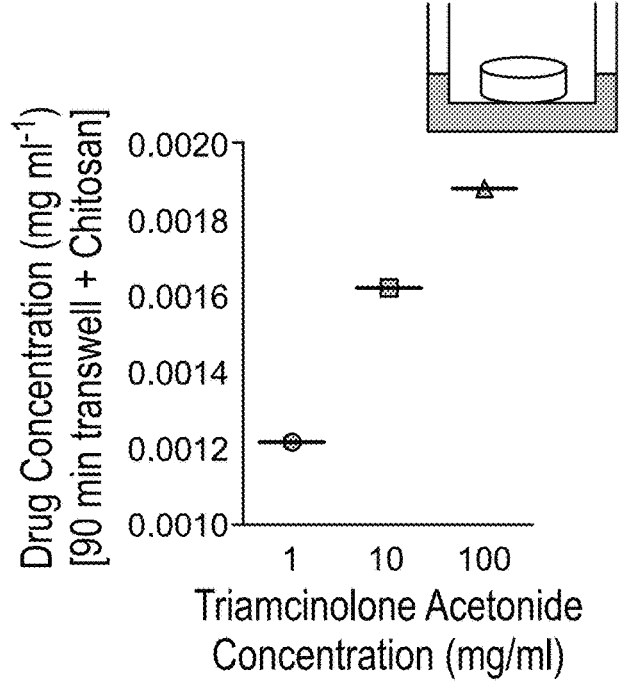
FIG. 2K
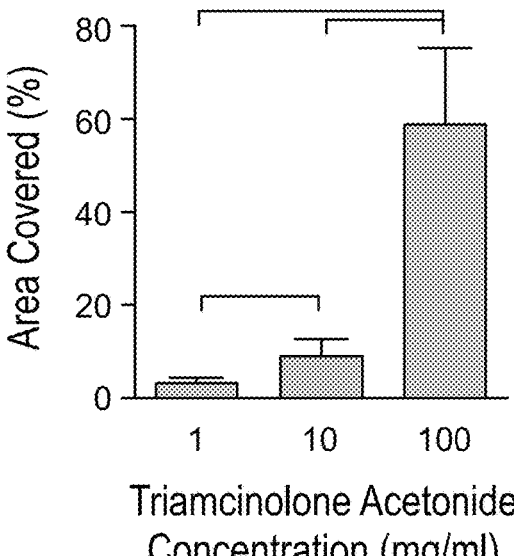
FIG. 2L
FIG. 2M

1mg/ml
(~33μm²)

10mg/ml
(~157μm²)

100mg/ml

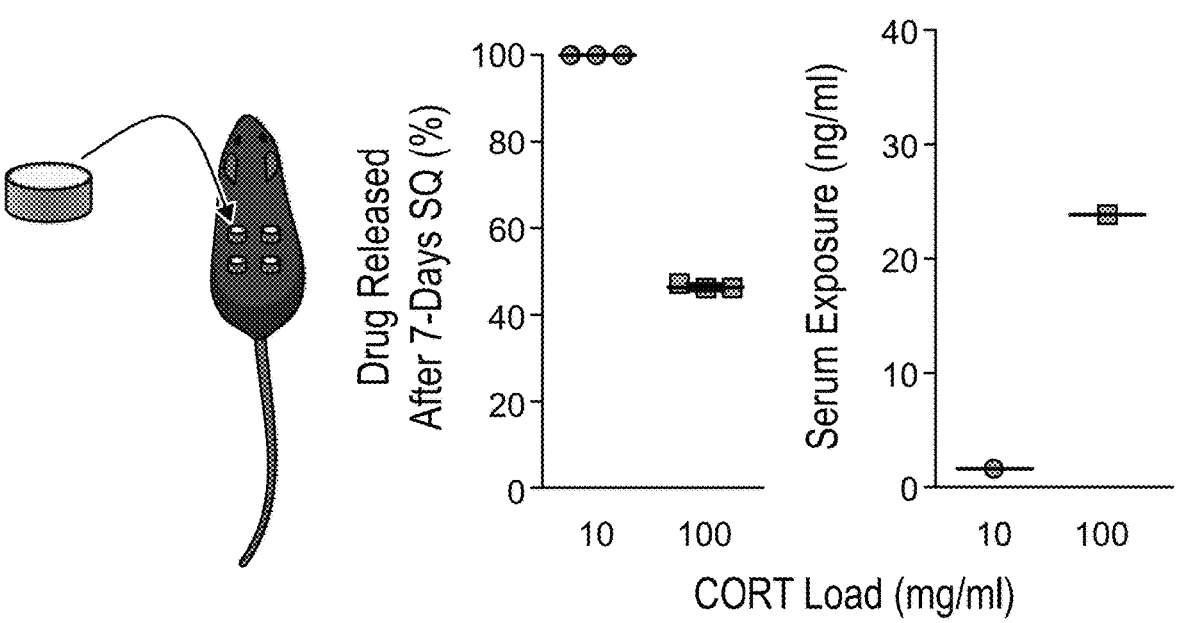
FIG. 3C
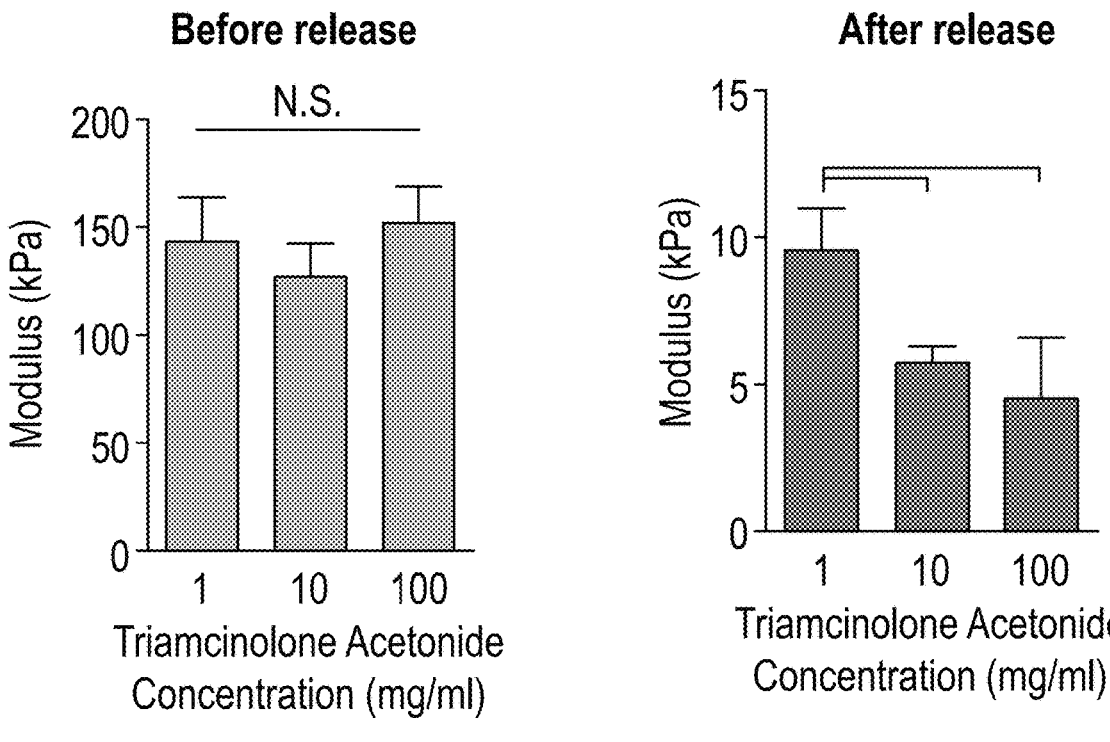
FIG. 3D                    FIG. 3E

TRC

Sandoz (NIBR)

TRC

Sandoz
(NIBR)

Large
particles

1mg/ml          10mg/ml          100mg/ml

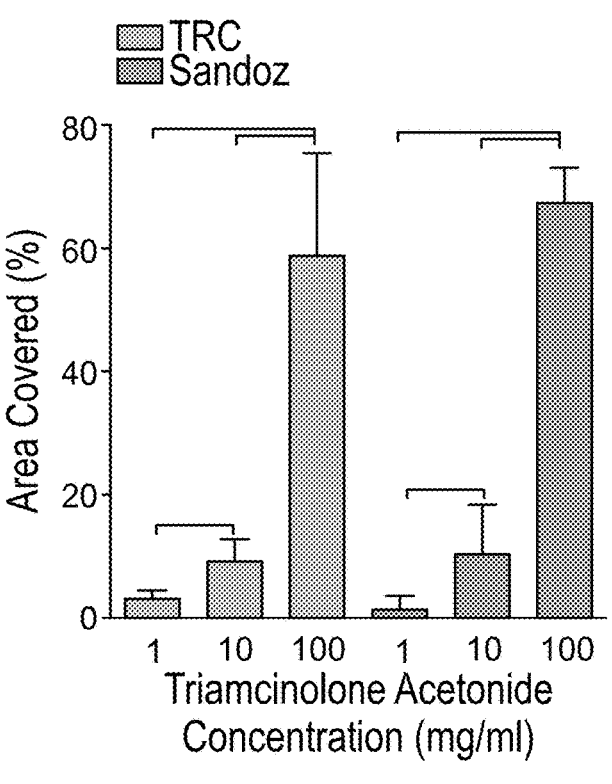
- (monomer solution)
- No effect of CORT type
FIG. 4K
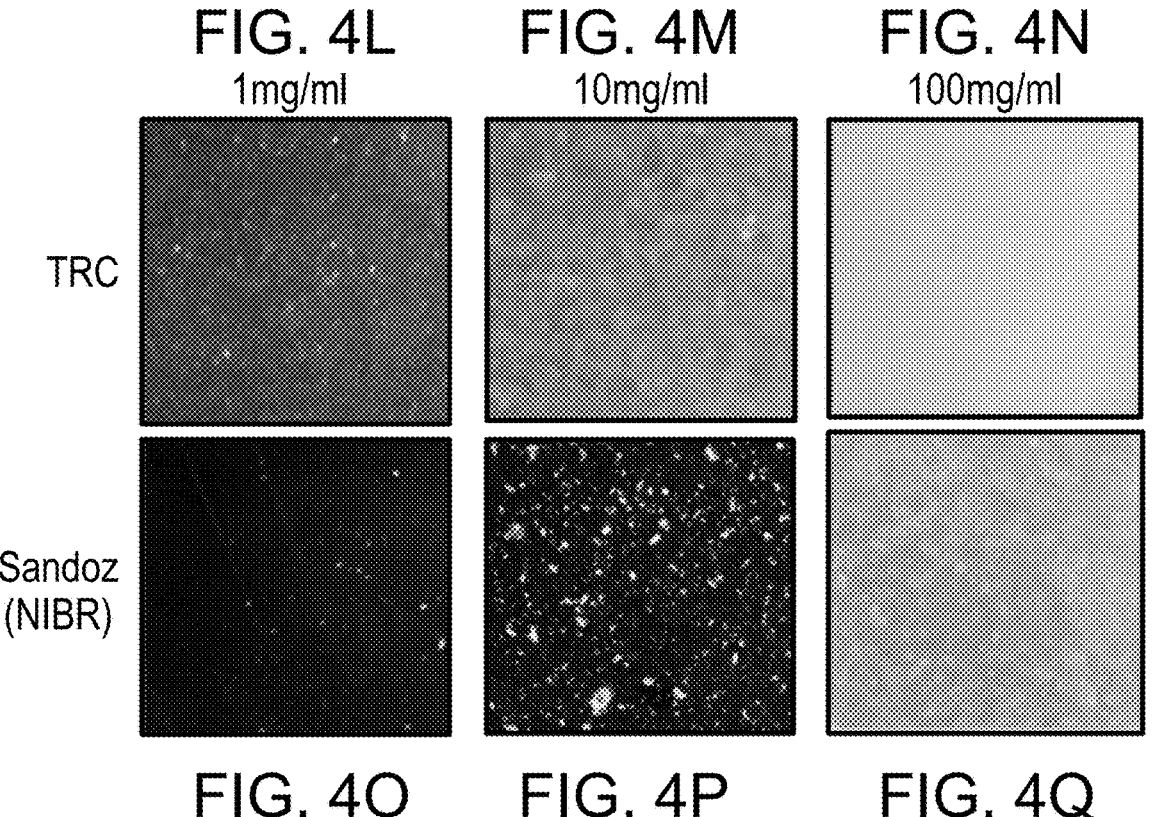
FIG. 4L
1mg/ml
FIG. 4M
10mg/ml
FIG. 4N
100mg/ml
FIG. 4O
FIG. 4P
FIG. 4Q

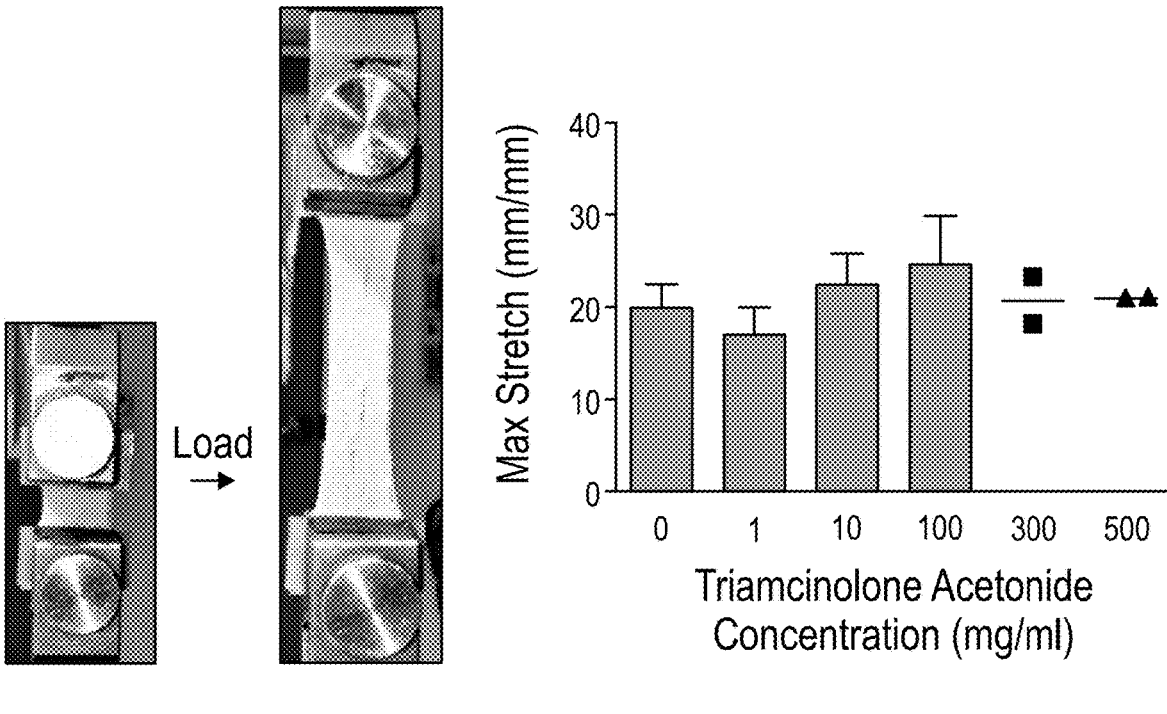
FIG. 5A                                    FIG. 5B
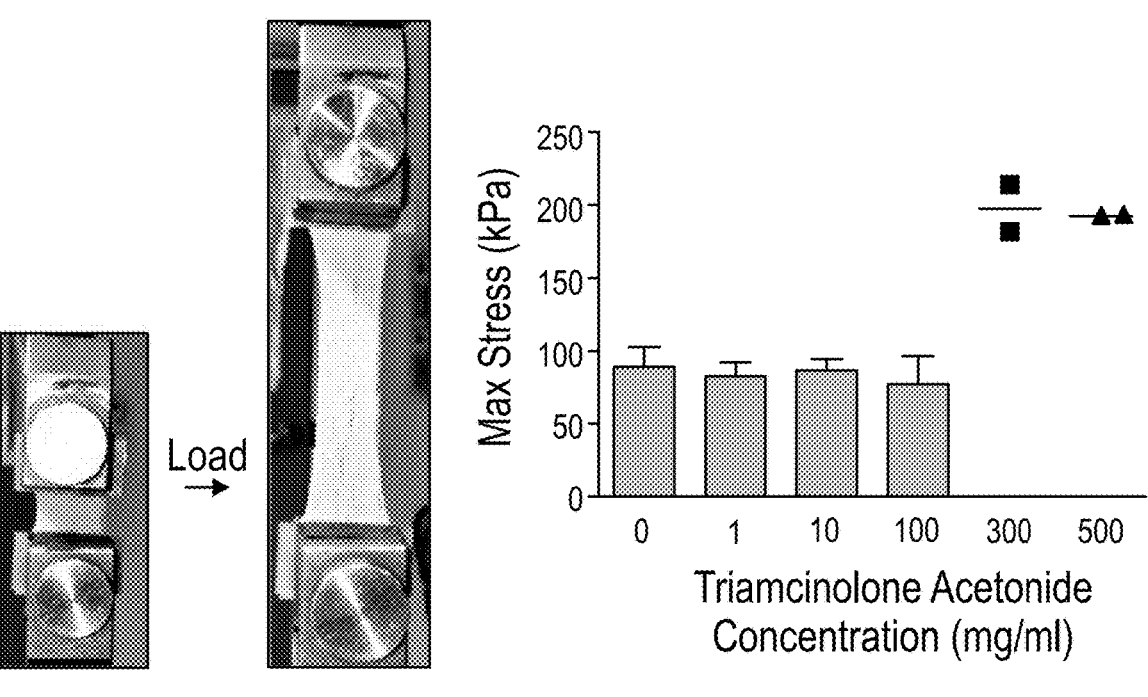
FIG. 5C                                    FIG. 5D

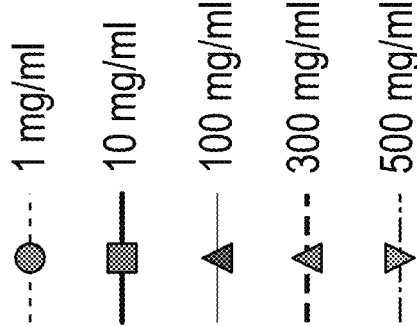
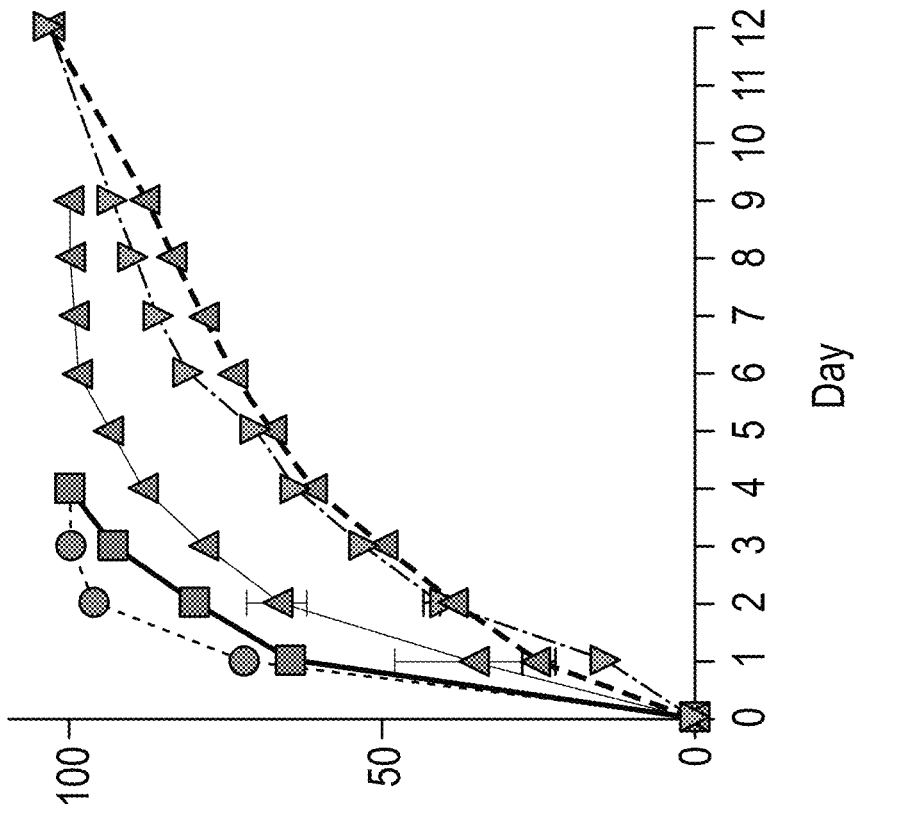
FIG. 5E

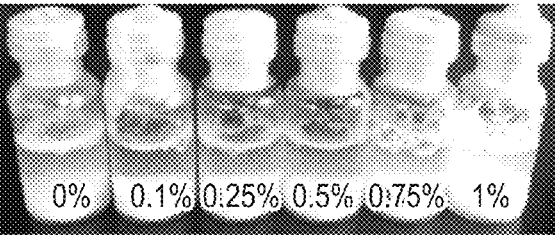
Poloxamer 188
Wetting agent (0→1%)
FIG. 6A
1 min (Sandoz)                5 min (Sandoz)
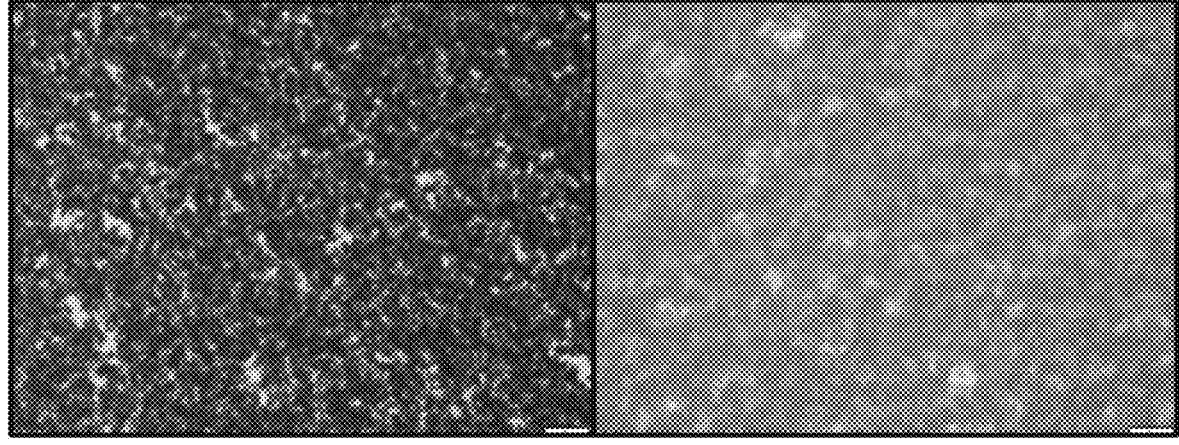
FIG. 6B             FIG. 6C
0%                  1%
FIG. 6D            FIG. 6E PVP: Alter viscosity (intrinsic
viscosity of monomer)

TRC                          Sandoz

0% PVP                    0.2% PVP

R = H or

Hydroxypropyl cellulose

| 0% | 0.5% | 3% |
|---|---|---|
| FIG. 8B | FIG. 8C | FIG. 8D |

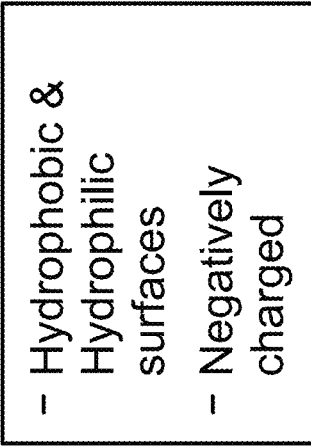
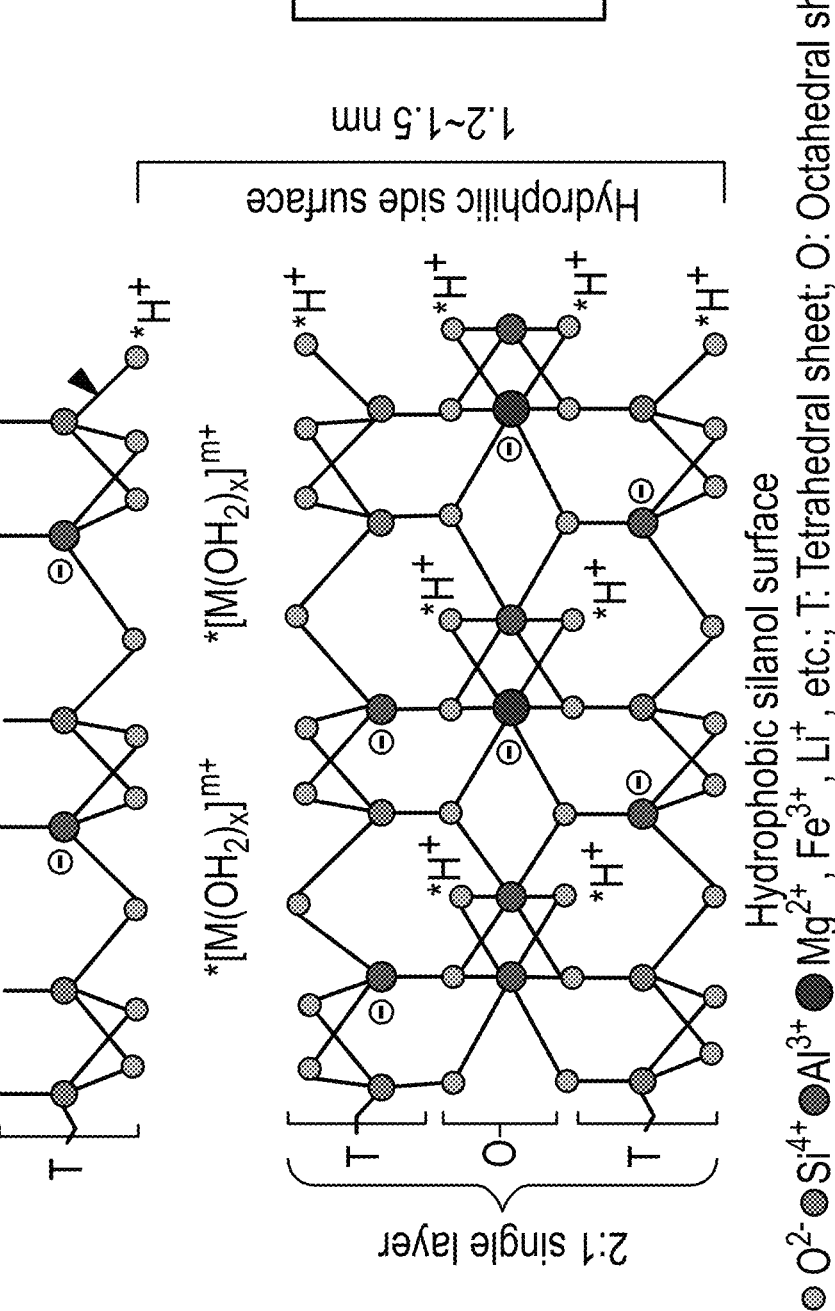
FIG. 10C

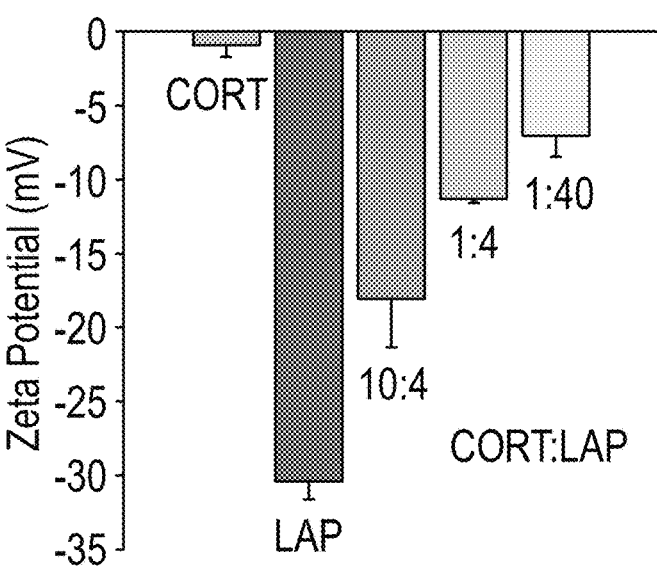
FIG. 13A
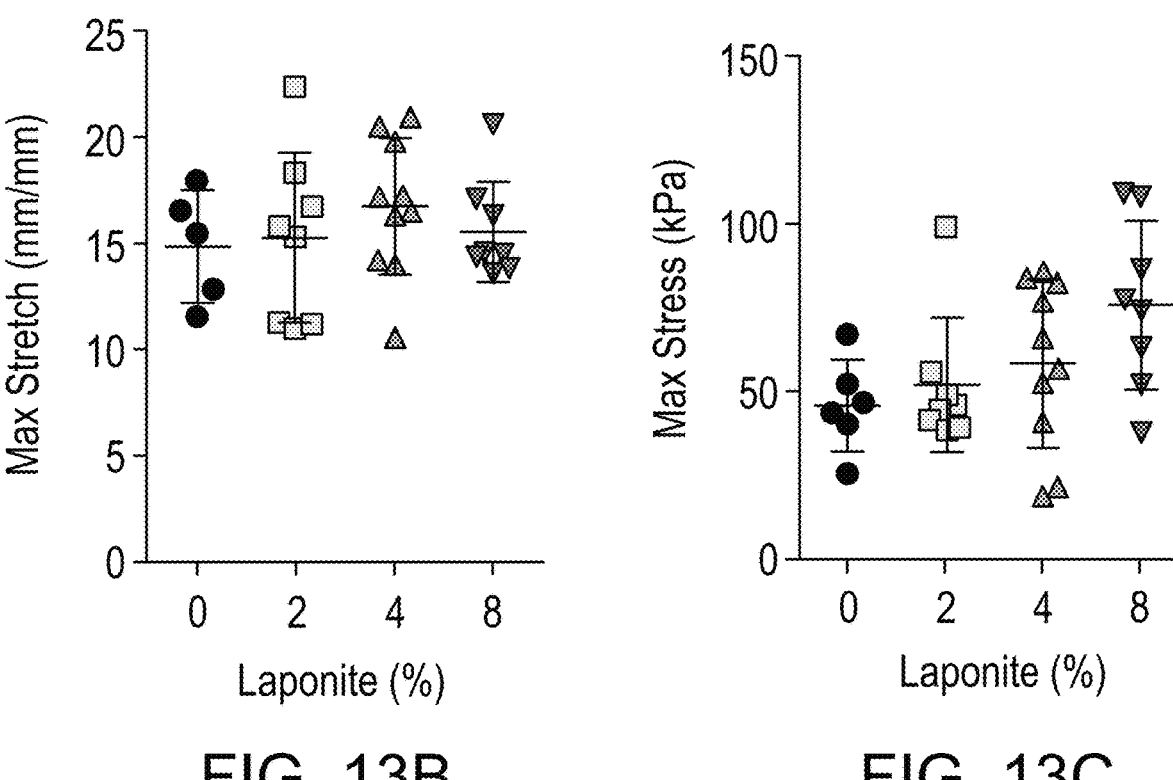
FIG. 13B
FIG. 13C

FIG. 14A                                   TRC
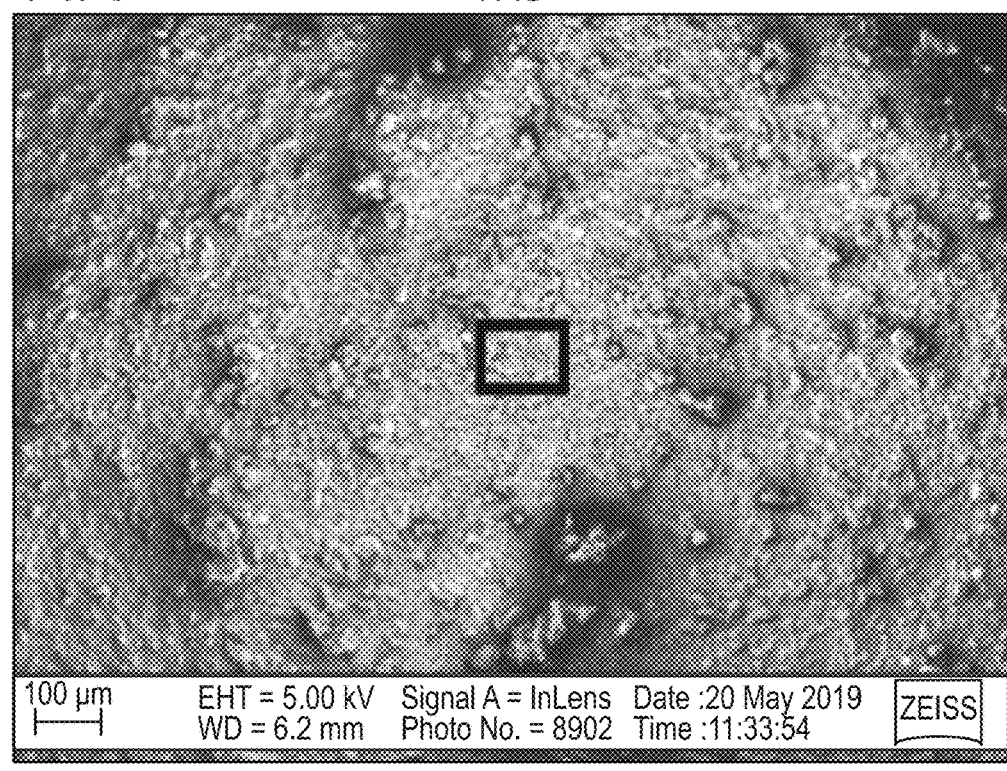
200x
FIG. 14B                         Sandoz: First Batch
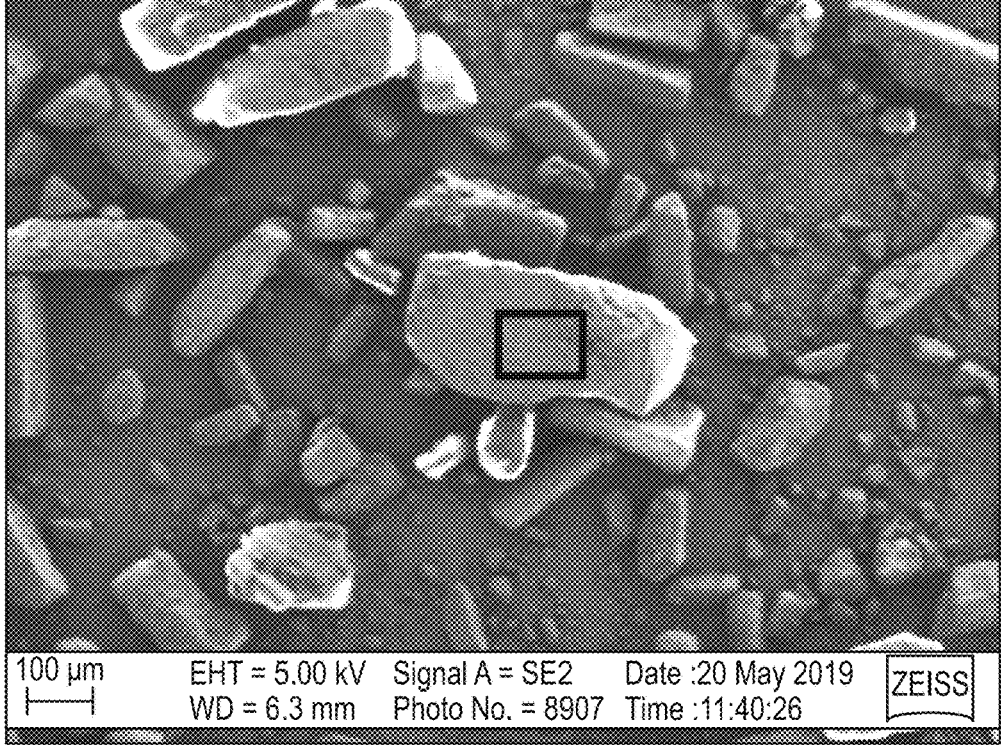

FIG. 14C    Sandoz: Second Batch
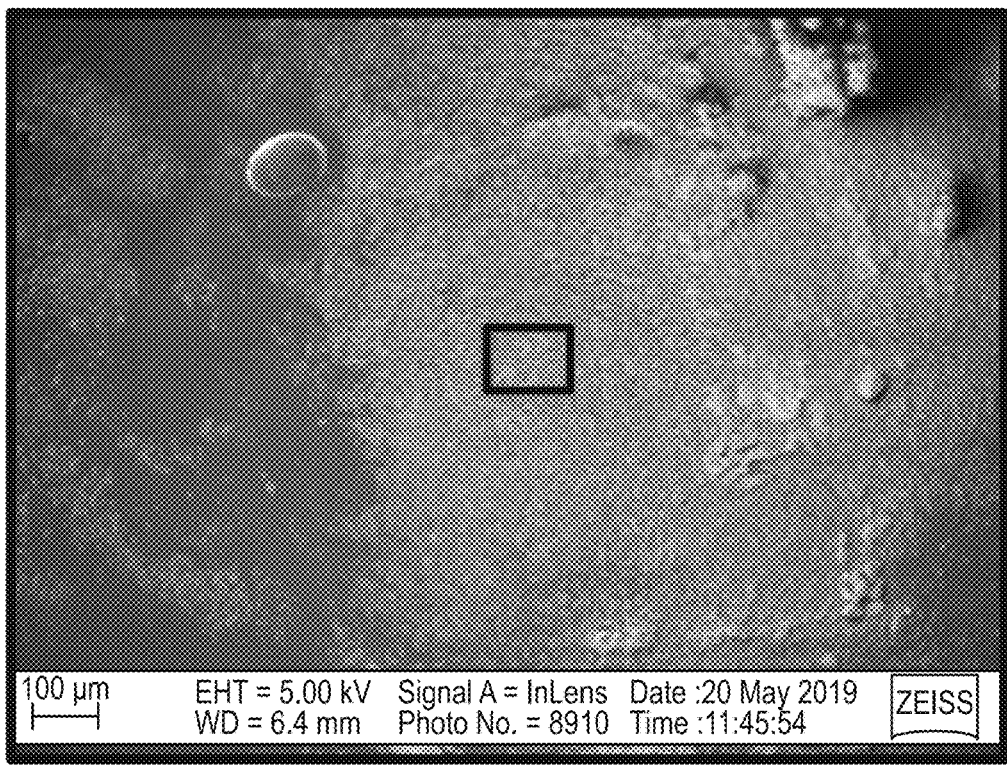
100 µm    EHT = 5.00 kV    Signal A = InLens    Date :20 May 2019    ZEISS
          WD = 6.4 mm      Photo No. = 8910    Time :11:45:54
FIG. 14D
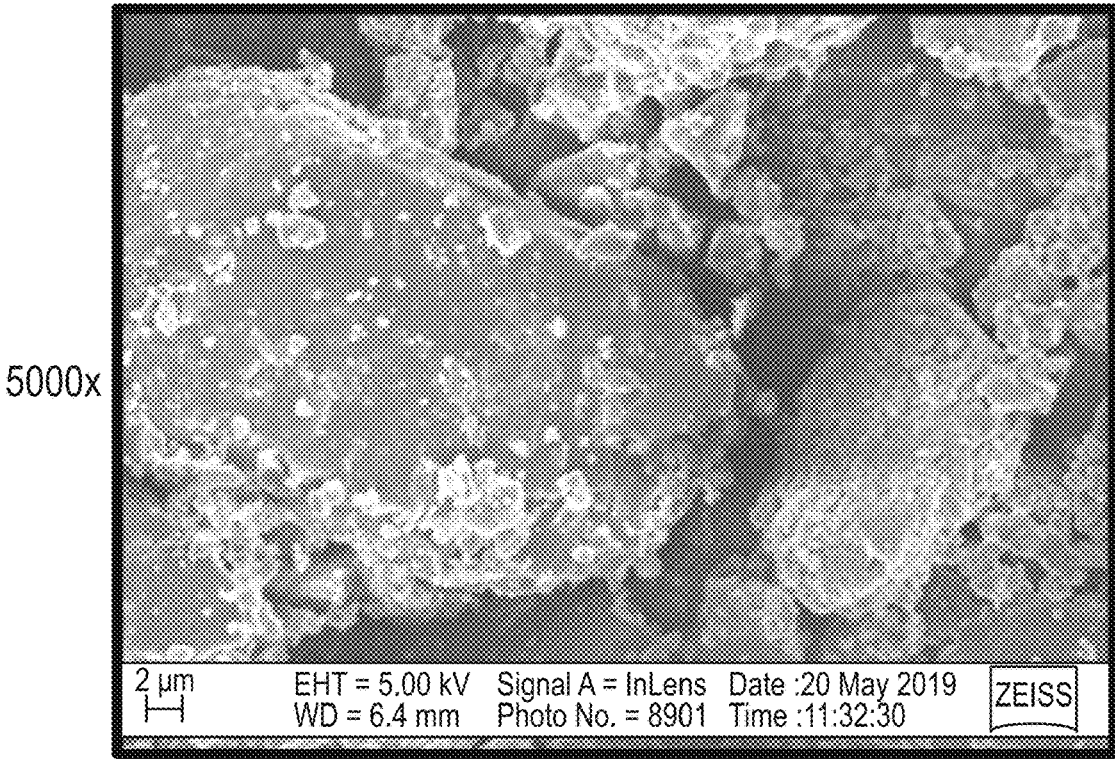
5000x
2 µm    EHT = 5.00 kV    Signal A = InLens    Date :20 May 2019    ZEISS
        WD = 6.4 mm      Photo No. = 8901    Time :11:32:30

1mg/ml     10mg/ml     100mg/ml

Sandoz (micronized)

Sandoz (unmicronized)

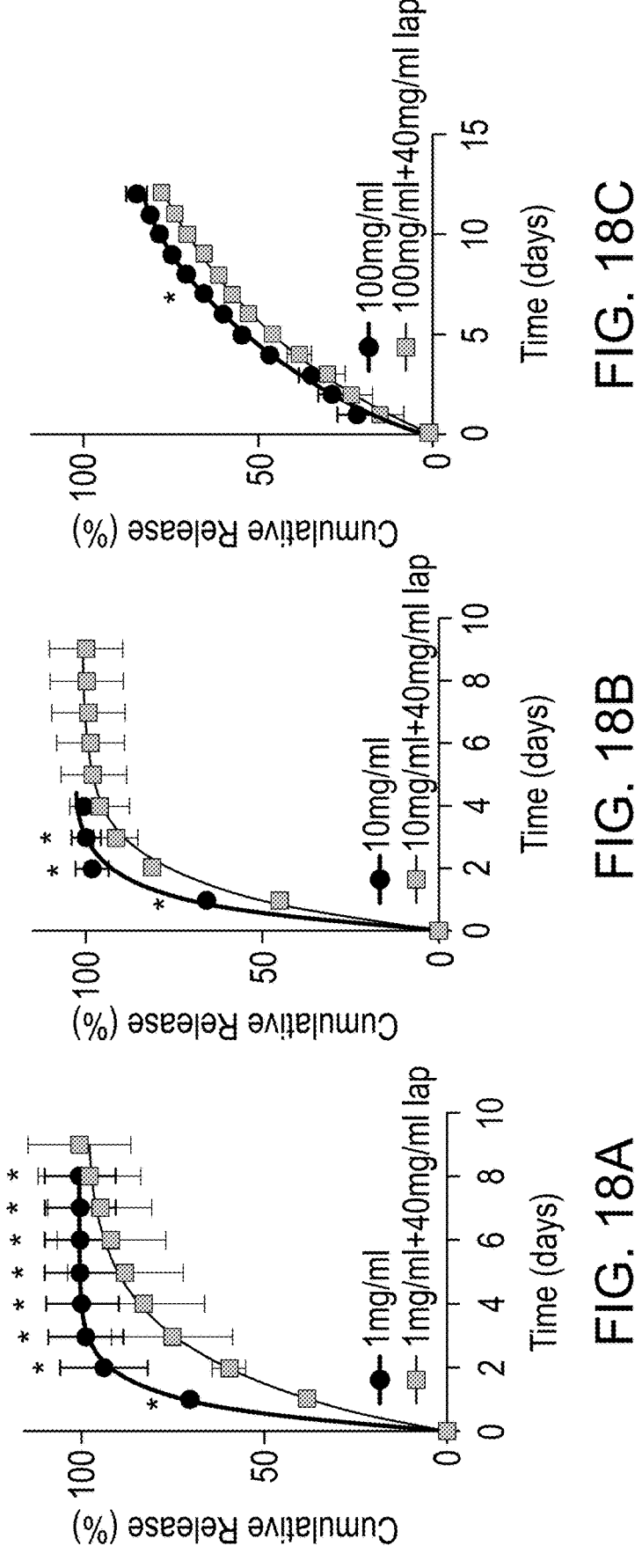

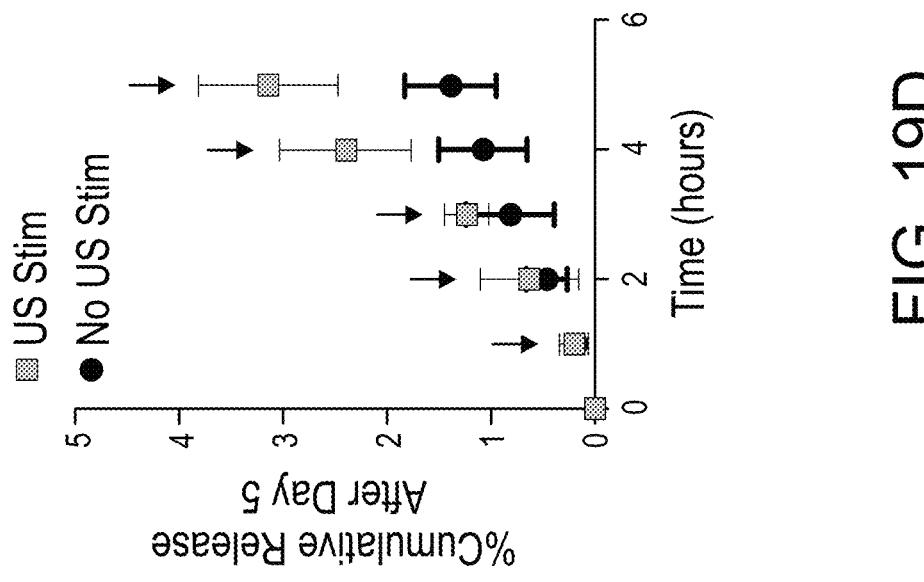
FIG. 19D
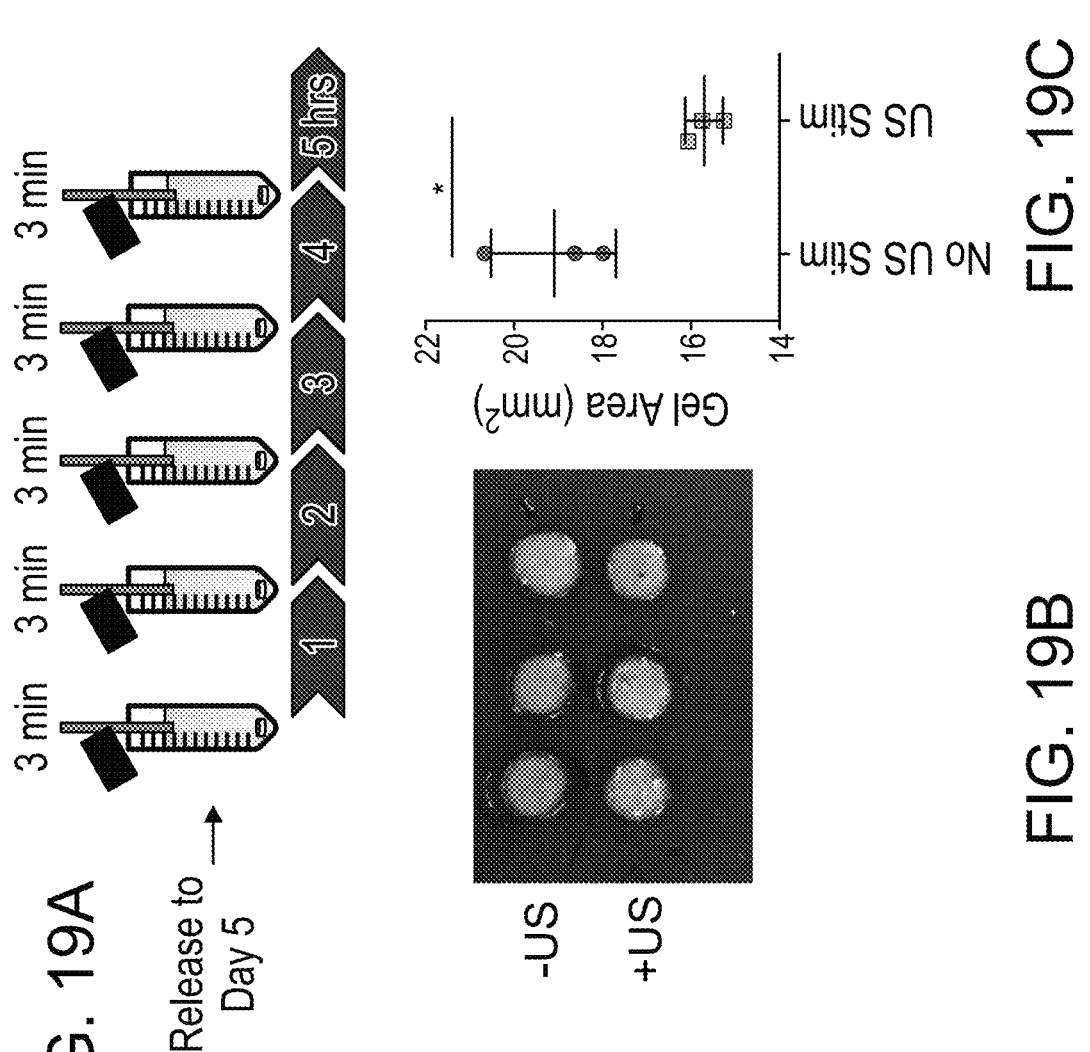
FIG. 19A
FIG. 19B
FIG. 19C

• 1xPBS with Ca++, RT, 2-days

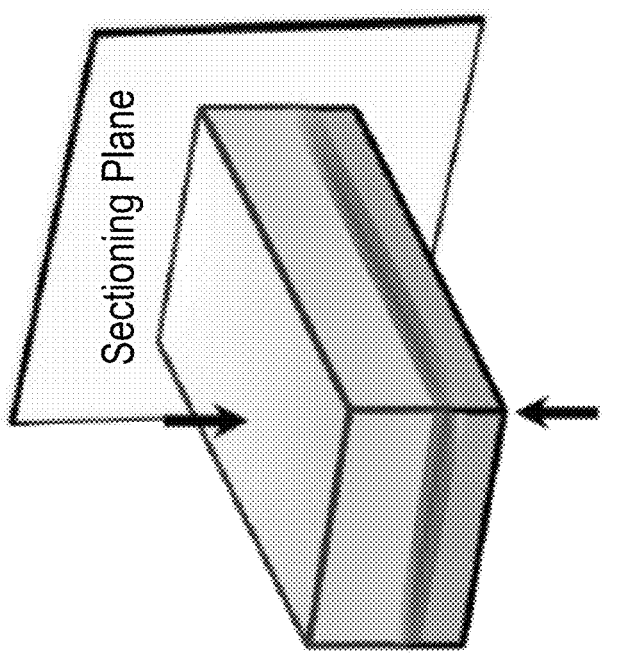
FIG. 23B
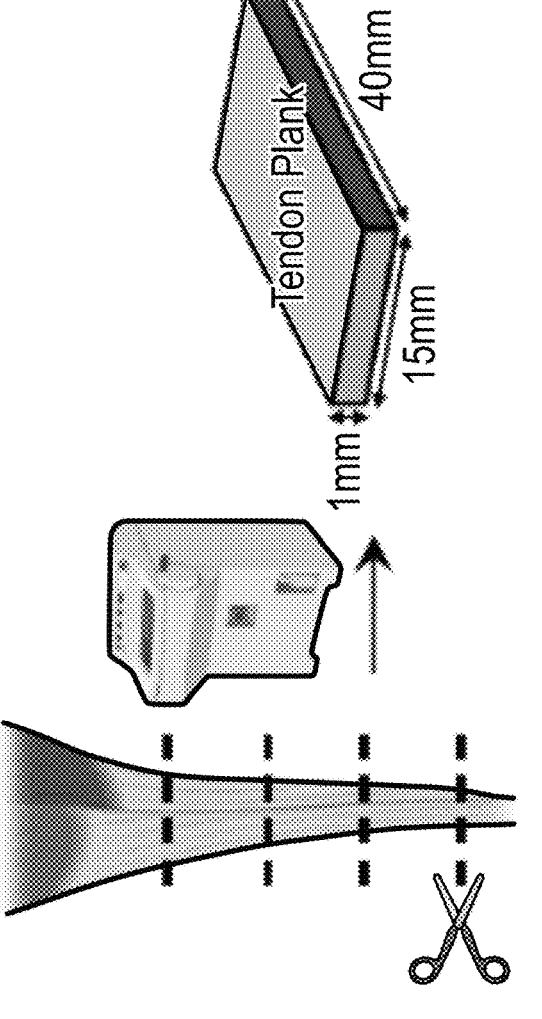
FIG. 23A

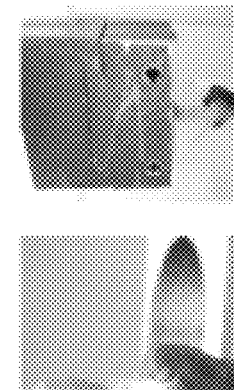
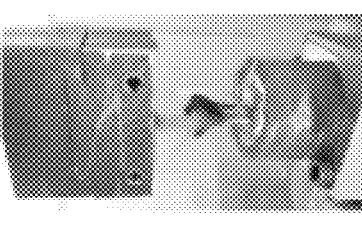
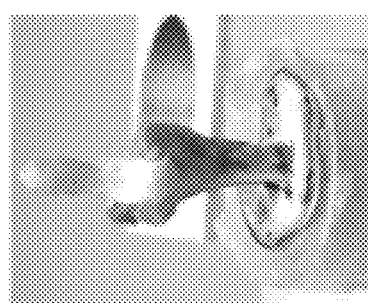
Test fixtures
in bath
Secure tibia in
pot (liquid
metal)
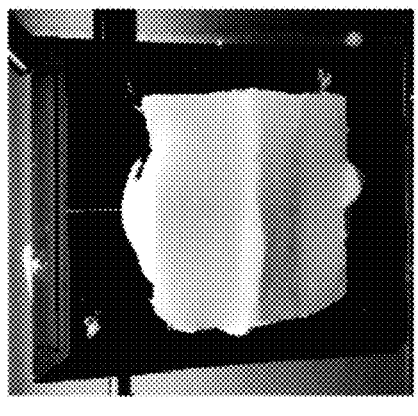
FIG. 24A
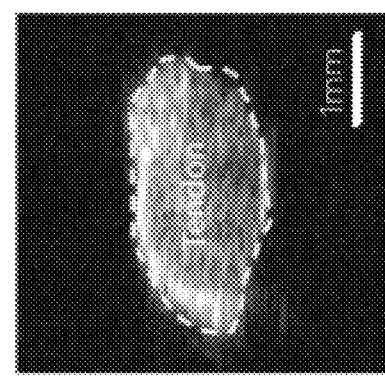
High frequency
ultrasound imaging
FIG. 24B
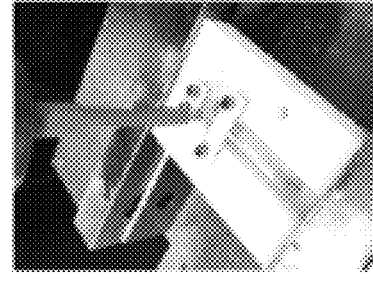
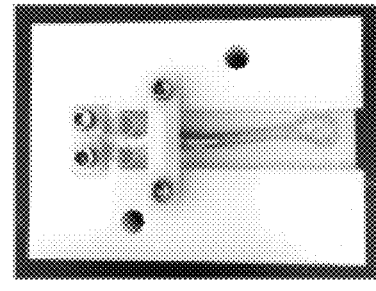
Stamp tendon
into "dog bone" shape

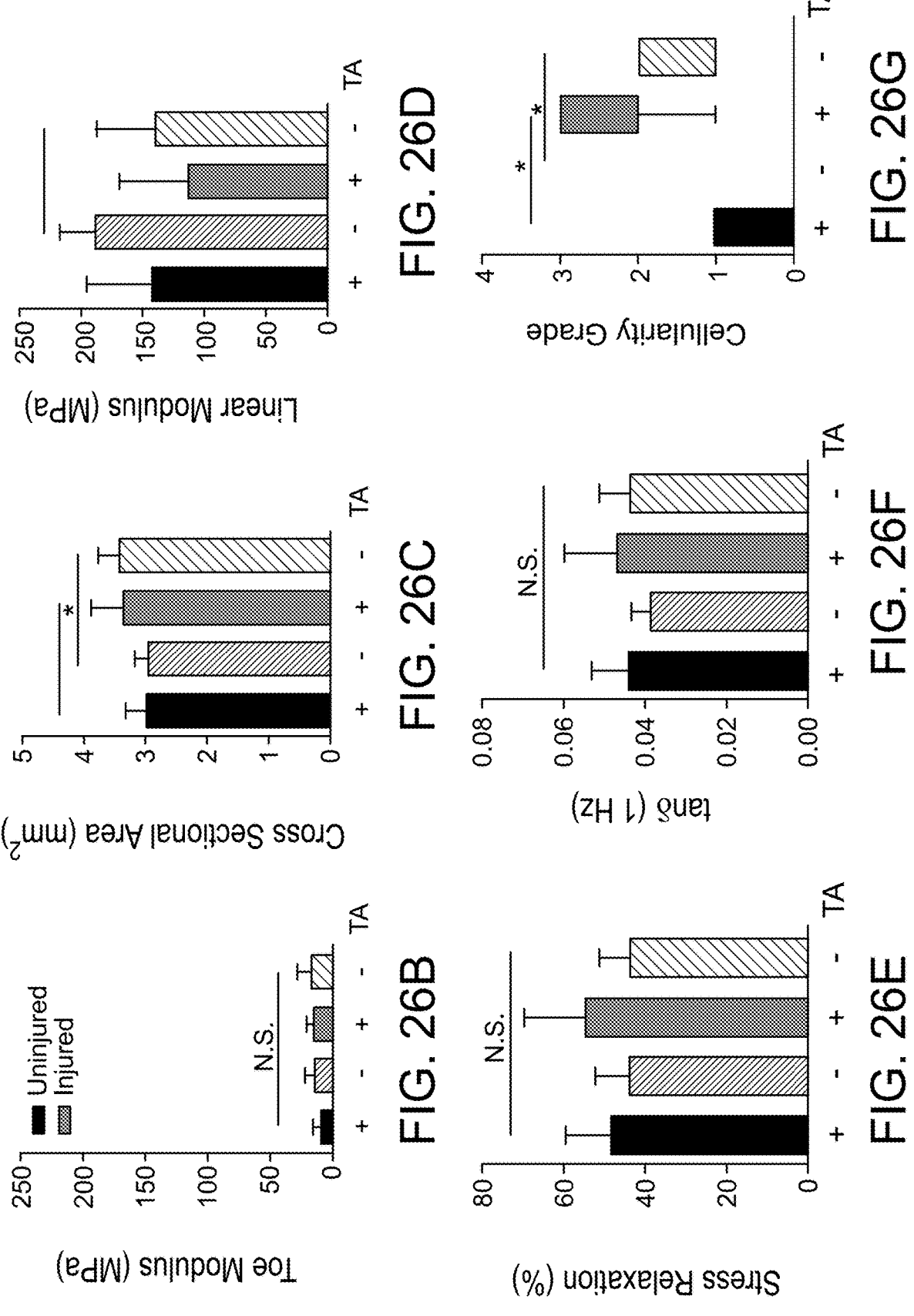

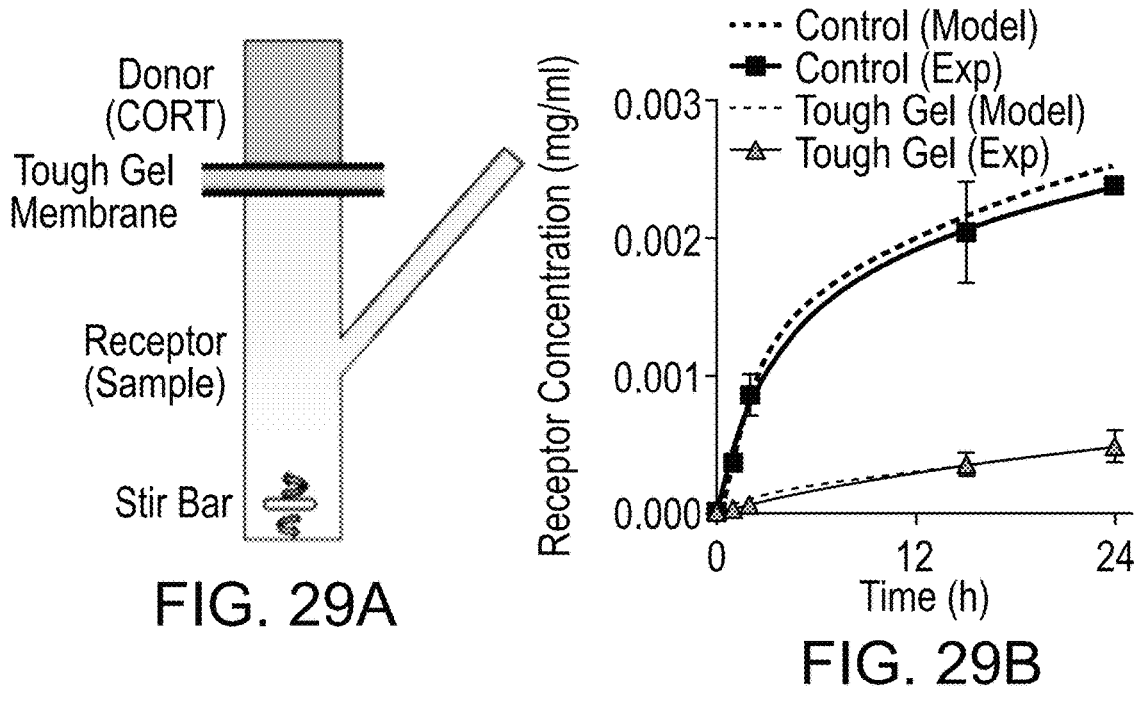
FIG. 29A
FIG. 29B
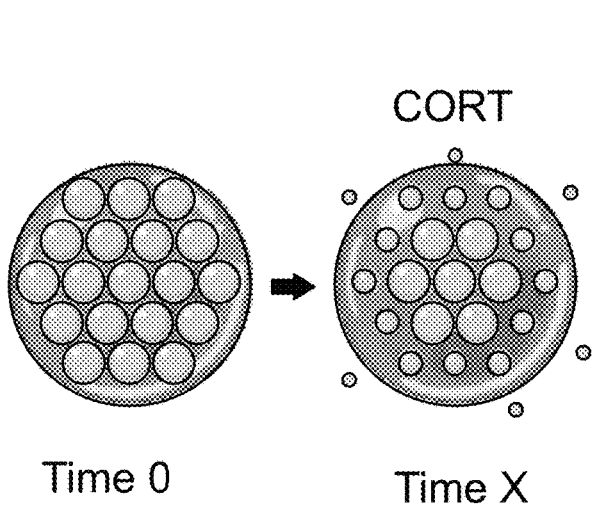
CORT
Time 0          Time X
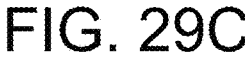
FIG. 29C
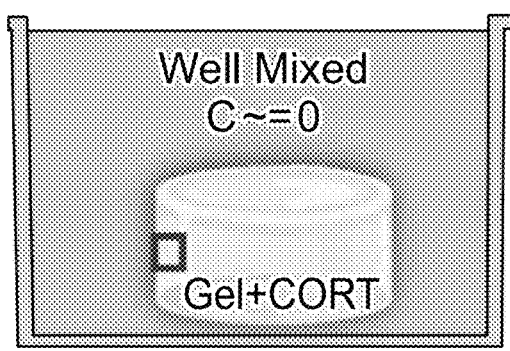
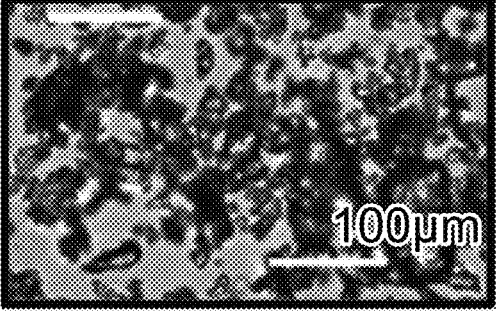
FIG. 29D

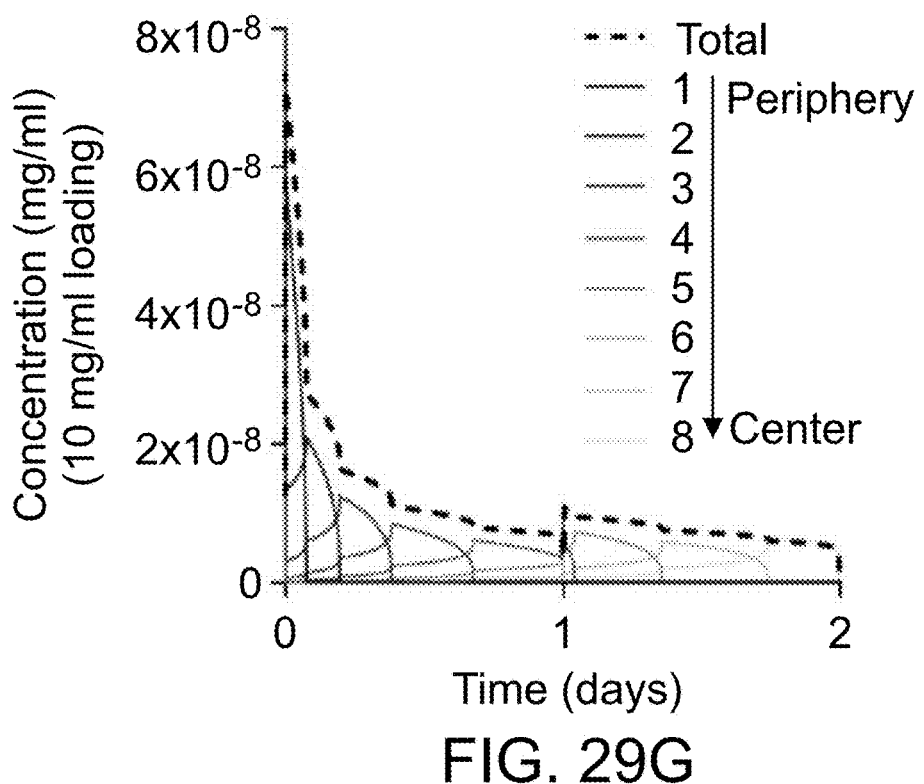
FIG. 29G
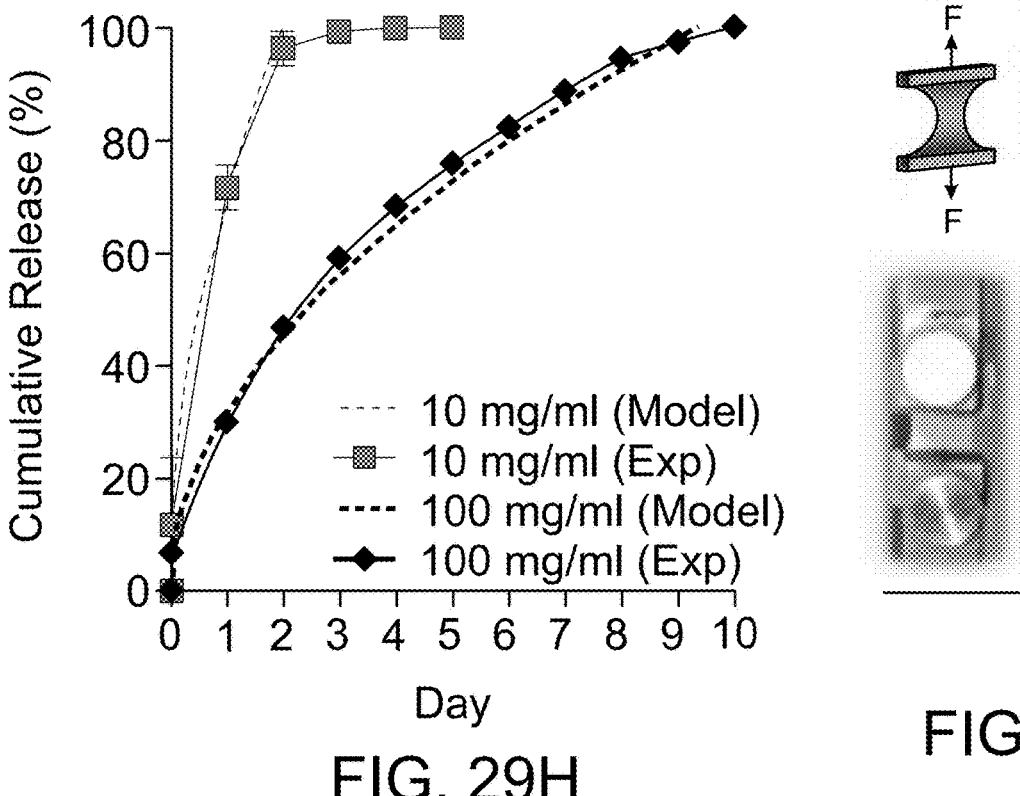
FIG. 29H
FIG. 29I

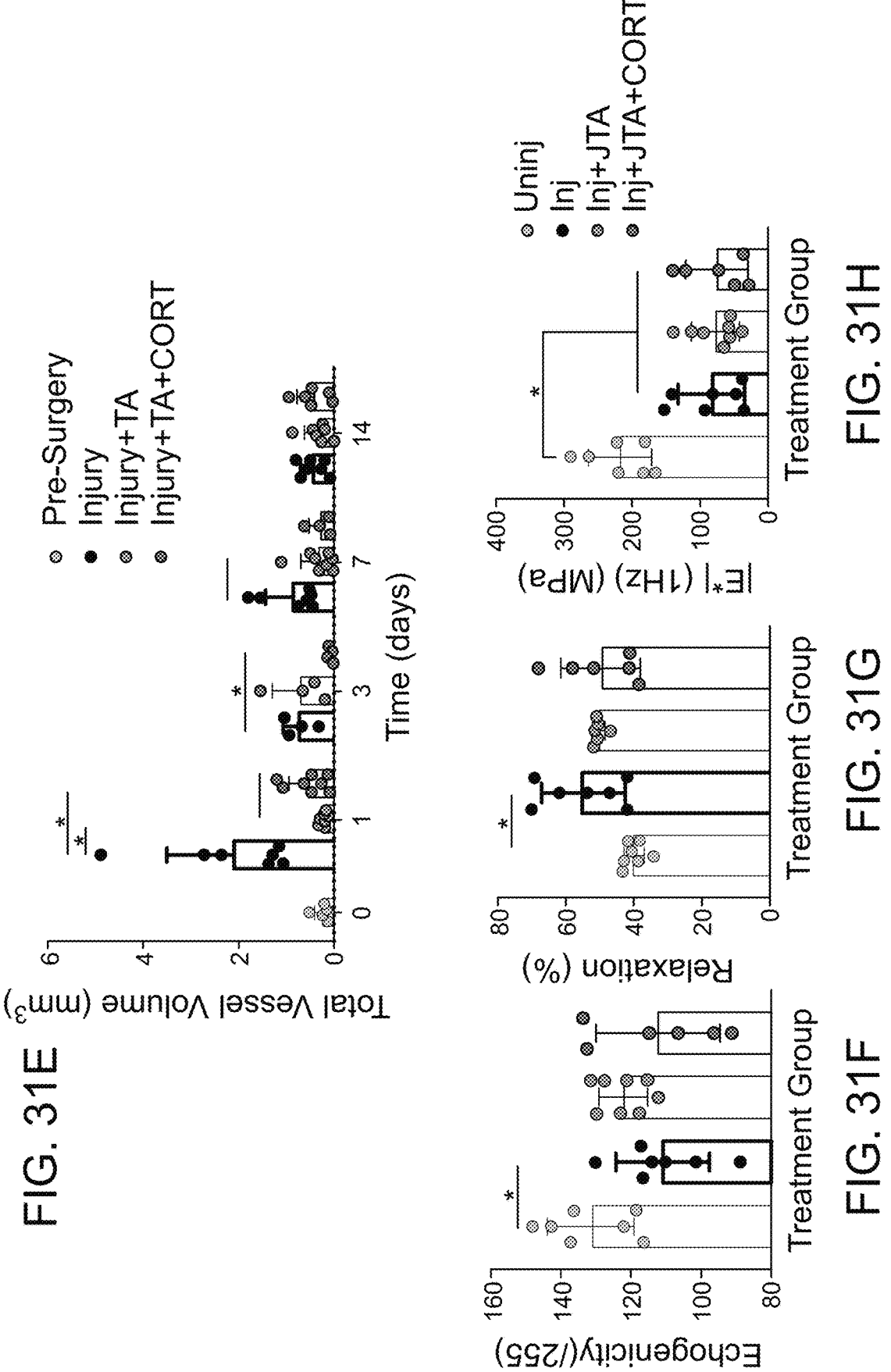

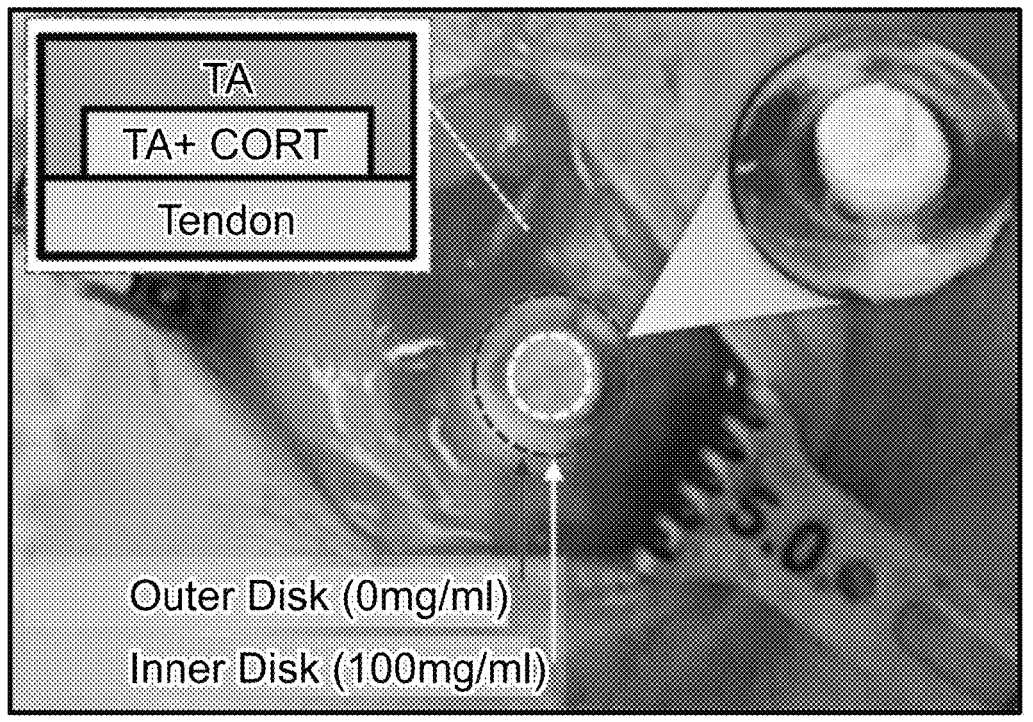
FIG. 32A
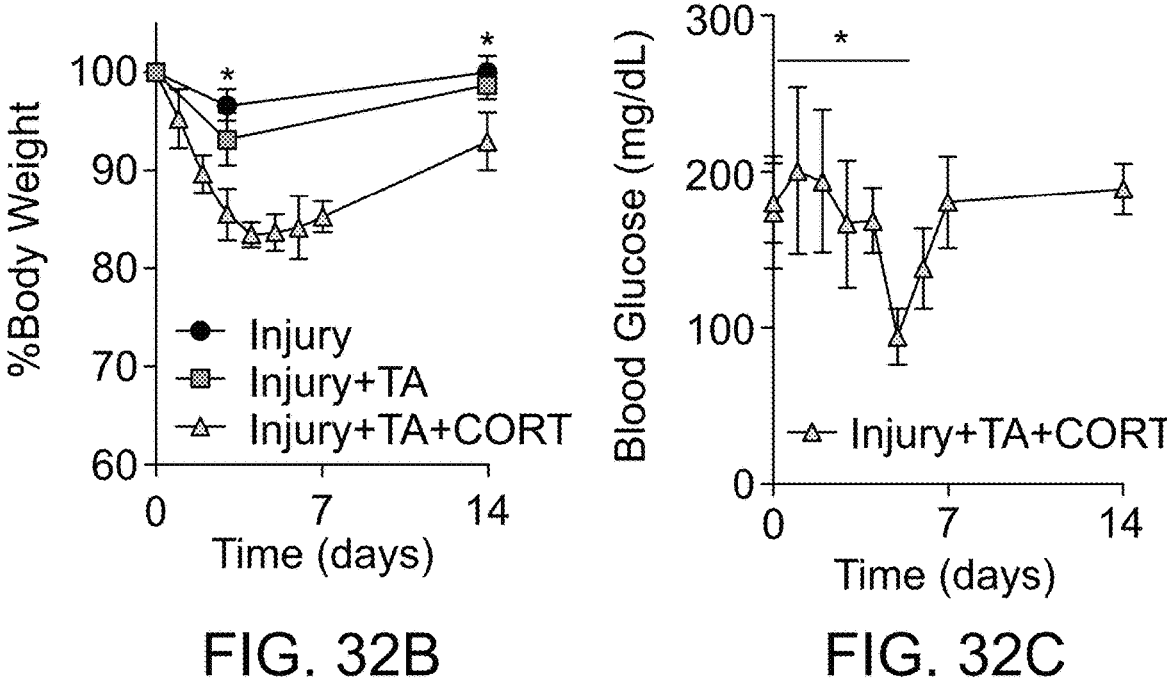
FIG. 32B                    FIG. 32C

Flexor tendons must glide during flexion

TOUGH GEL-BASED DRUG DELIVERY COMPOSITIONS AND METHODS THEREOF

CROSS-REFERENCE TO RELATED APPLICATIONS

The instant application is a 35 U.S.C. § 371 national stage filing of International Application No. PCT/US2020/051427, filed on Sep. 18, 2020, which claims priority to U.S. Provisional Application No. 62/903,315, filed on Sep. 20, 2019. The entire contents of each of the aforementioned applications are incorporated herein by reference.

STATEMENT OF GOVERNMENT SUPPORT

This invention was made with U.S. government support under Grant No. AG057135 awarded by the National Institutes of Health. The government has certain rights in the invention.

BACKGROUND

Ruptures and repetitive strain injuries to tendon are often accompanied by tissue inflammation and degeneration. While current medications delivered orally or intravenously are susceptible to drug denaturation or drug-induced toxicity, hydrogel-based biomaterials may offer advantages by increasing the drug bioavailability locally and allowing for extended release. Traditional hydrogels, however, display deficiencies in mechanical toughness and drug storage instability, resulting in a trade-off between loading capacity and tunable release.

The timing of delivery of therapeutic agents to tendon is extremely crucial. For instance, Blomgran et al. (*Sci Rep.,* 2017, 7(12468): 1-7) reported that dexamethasone, when delivered late, improved tendon healing, but not when the delivery of the drug was early. Muto and colleagues reported that triamcinolone acetonide decreased cell viability and changed cell morphology, but this could be prevented by administering platelet-rich plasma (*J Orthop Res.,* 2013, 31(6):976-982; *Bone Joint Res.,* 2016, 5(12):602-609).

Therefore, there exists an unmet need for strategies for local, tunable, and extended drug delivery to tendon tissue.

SUMMARY

Disclosed herein are tough gel compositions that are capable of tunable and extended drug delivery, which comprise an interpenetrating networks (IPN) hydrogel composition having a first polymer network that is covalently crosslinked and a second polymer network that is ionically or physically crosslinked.

Accordingly, in one aspect, the present invention provides an interpenetrating networks (IPN) hydrogel composition, The IPN hydrogel composition comprises a first polymer network and a second polymer network; and at least one therapeutic agent, wherein the first polymer network comprises a first polymer that is covalently crosslinked and the second polymer network comprises a second polymer that is ionically crosslinked; and wherein the therapeutic agent is released from the IPN hydrogel composition in a sustained manner.

In another aspect, the present invention provides an adhesive composition. The adhesive composition comprises an interpenetrating networks (IPN) hydrogel, comprising a first polymer network and a second polymer network; and at least one therapeutic agent; and an adhesive polymer layer attached to the IPN hydrogel, wherein the first polymer network comprises a first polymer that is covalently crosslinked and the second polymer network comprises a second polymer that is ionically crosslinked; and wherein the therapeutic agent is released from the adhesive composition in a sustained manner.

In still another aspect, the present invention provides an interpenetrating networks (IPN) hydrogel composition. The IPN hydrogel composition comprises a first polymer network and a second polymer network; at least one therapeutic agent; and a clay material; wherein the first polymer network comprises a first polymer that is covalently crosslinked and the second polymer network comprises a second polymer that is ionically crosslinked.

In yet another aspect, the present invention provides an adhesive composition. The adhesive composition comprises an interpenetrating networks (IPN) hydrogel, comprising: a first polymer network and a second polymer network; at least one therapeutic agent; and a clay material; and an adhesive polymer layer attached to the IPN hydrogel; wherein the first polymer network comprises a first polymer that is covalently crosslinked and the second polymer network comprises a second polymer that is ionically crosslinked.

In one embodiment of various aspects of the invention, the therapeutic agent is release over a period of less than 1 day, about 1 day, about 2 days, about 4 days, about 1 week, about 2 weeks, about 1 month, about 2 months, about 4 months, about 6 months, about 1 years, or longer.

In one embodiment of various aspects of the invention, the concentration of the therapeutic agent (the therapeutic agent/hydrogel w/v %) is greater than the solubility limit of the therapeutic agent in water. In another embodiment, the concentration of the therapeutic agent is at least about 2 times, about 4 times, about 8 times, about 16 times, about times, about 50 times, about 100 times, about 200 times, about 500 times, about 1000 times, about 2000 times, about 5000 times, about 10000 times, about 20000 times, about 25000 times greater than the solubility limit of the therapeutic agent.

In yet another embodiment, the therapeutic agent forms an aggregate suspended in the IPN hydrogel. In another embodiment, the aggregate has a cross section area that is between about 1 $\mu m^2$ to about 500 $\mu m^2$. In still another embodiment, the aggregate has a cross section area that is greater than about 1 $\mu m^2$, about 2 $\mu m^2$, about 5 $\mu m^2$, about 10 $\mu m^2$, about 20 $\mu m^2$, about 50 $\mu m^2$, about 100 $\mu m^2$, about 150 $\mu m^2$, about 200 $\mu m^2$, or about 500 $\mu m^2$ In still another embodiment, the therapeutic agent is released from the IPN hydrogel in a substantially constant rate.

In one embodiment of the various aspects of the invention, the therapeutic agent is selected from the group consisting of a biologic, a small molecule, a metal, or a combination thereof.

In one embodiment, the biologic is selected from the group consisting of an antibody, a vaccine, a blood, a blood component, an allergen, a nucleic acid, a protein, a peptide, a cell, a hormone, a growth factor, a cytokine, a chemokine, an immune cell, or a combination thereof.

In another embodiment, the therapeutic agent is a substance that treats inflammation. In still another embodiment, the therapeutic agent is a substance that promotes tissue regeneration. In yet another embodiment, the tissue is selected from skin tissue, muscle tissue, tendon tissue, ligament tissue, bone tissue, nerve tissue, connective tissue, bursa tissue, adipose tissue, or a combination thereof. In one embodiment, the therapeutic agent is a substance that promotes reinnervation. In another embodiment, wherein the therapeutic agent is a substance that relieves or alleviates pain.

In still another embodiment, the therapeutic agent is selected from the group consisting of hepatocyte growth factor (HGF), basic fibroblast growth factor (bFGF), Insulin-like growth factor-1 (IGF-1), nerve growth factor (NGF), leukemia inhibitory factor (LIF), acid fibroblast growth factor (aFGF), platelet-derived growth factor (PDGF-AA), platelet-derived growth factor (PDGF-BB), epidermal growth factor (EGF), transforming growth factor-α (TGF-α), transforming growth factor-β1 (TGF-β1), vascular endothelial growth factor 121 (VEGF$_{121}$), vascular endothelial growth factor 121b (VEGF$_{121}$b), vascular endothelial growth factor 145 (VEGF$_{145}$), vascular endothelial growth factor 165 (VEGF$_{165}$), vascular endothelial growth factor 165b (VEGF$_{165}$b), vascular endothelial growth factor 189 (VEGF$_{189}$), and vascular endothelial growth factor 206 (VEGF$_{206}$).

In yet another embodiment, the composition of any one of claims 1-14, wherein the therapeutic agent is a corticosteroid. In one embodiment, the corticosteroid is selected from betamethasone, prednisone, clobetasol, prednisolone, triamcinolone, methylprednisolone, dexamethasone, or a pharmaceutically acceptable salt thereof. In another embodiment, the corticosteroid is triamcinolone or a pharmaceutically acceptable salt thereof.

In yet another embodiment, the therapeutic agent is a nonsteroidal anti-inflammatory drug (NSAID). In one embodiment, the NSAID is selected from the group consisting of aspirin salsalate (Amigesic), diflunisal (Dolobid), ibuprofen (Motrin), ketoprofen (Orudis), nabumetone (Relafen), piroxicam (Feldene), naproxen (Aleve, Naprosyn,) diclofenac (Voltaren), indomethacin (Indocin), sulindac (Clinoril), tolmetin (Tolectin), etodolac (Lodine), ketorolac (Toradol), oxaprozin (Daypro), celecoxib (Celebrex).

In one embodiment of various aspects of the invention, the composition comprises about 0.1 mg/ml to about 500 mg/ml of the therapeutic agent. In another embodiment, the composition comprises about 0.5 mg/ml to about 100 mg/ml of the therapeutic agent. In still another embodiment, wherein the composition comprises about 1 mg/ml, about 10 mg/ml, or about 100 mg/ml of the therapeutic agent.

In one embodiment of various aspects of the invention, the clay material comprises a plurality of clay particles that aggregate in the second polymer network. In one embodiment, the therapeutic agent is encapsulated in the hydrophobic interlayer spaces of the aggregated clay particles. In another embodiment, the therapeutic agent is adsorbed onto the aggregated clay particles.

In one embodiment of various aspects of the invention, the clay material is selected from the group consisting of kaolinite, illite, chlorite, vermiculite, smectite, bentonite, sodium smectite, attapulgite, sepiolite, dicite, halloysite, nacrite, and laponite. In another embodiment, the clay material is laponite.

In one embodiment of various aspects of the invention, the composition of the invention comprises about 1 mg/ml to about 200 mg/ml of the clay material. In another embodiment, the composition of the invention comprises about 1 mg/ml to about 120 mg/ml of the clay material. In still another embodiment, the composition of the invention comprises about 20 mg/ml, about 40 mg/ml, about 80 mg/ml, or about 120 mg/ml of the clay material.

In one embodiment of various aspects of the invention, the weight ratio of the clay material to the therapeutic agent is from about 100:1 to about 2:5. In another embodiment, the weight ratio of the clay material to the therapeutic is from about 50:1 to about 2:5.

In one embodiment of various aspects of the invention, the first polymer is selected from the group consisting of polyacrylamide, poly(hydroxyethylmethacrylate) (PHEMA), poly(vinyl alcohol) (PVA), polyethylene glycol (PEG), polyphosphazene, collagen, gelatin, poly(acrylate), poly(methacrylate), poly(methacrylamide), poly(acrylic acid), poly(N-isopropylacrylamide) (PNIPAM), poly(N,N-dimentylacrylamide), poly(allylamine) and copolymers thereof. In some embodiment, the first polymer is polyacrylamide.

In one embodiment of various aspects of the invention, the first polymer network comprises a first polymer that is covalently crosslinked with a covalent crosslinking agent selected from the group consisting of N,N-methylenebisacrylamide (MBAA), a methacrylate crosslinker, N,N'-dicyclohexylcarbodiimide (DCC), 1-ethyl-3-(3-dimethyl-aminopropyl)carbodiimide (ECC), N-hydroxysuccinimide, N-hydroxysulfosuccinimide, glutaraldehyde, and a transglutaminase, optionally wherein the covalent crosslinking agent is N,N-methylenebisacrylamide (MBAA). In another embodiment, the covalent crosslinking agent is N,N-methylenebisacrylamide (MBAA).

In still another embodiment, the first polymer network comprises a first polymer that is covalently crosslinked with a biodegradable covalent crosslinking agent selected from the group consisting of a poly(ethylene glycol) acrylate, a gelatin acrylate, a hyaluronic acid acrylate, an alginate acrylate, and poloxamer (PEG-PPG-PEG) diacrylate. In yet another embodiment, the biodegradable covalent crosslinking agent is selected from the group consisting of a poly(ethylene glycol) diacrylate (PEGDA), a gelatin methacrylate (GelMA), a methacrylated alginate (AlgMA), hyaluronic acid methacrylate, and poloxamer (PEG-PPG-PEG) diacrylate. In yet another embodiment, the biodegradable covalent crosslinking agent is a PEGDA having a molecular weight of about 250 to about 20,000 Da.

In one embodiment of various aspects of the invention, the second polymer is selected from the group consisting of alginate, pectate, carboxymethyl cellulose, oxidized carboxymethyl cellulose, hyaluronate, chitosan, κ-carrageenan, ι-carrageenan and λ-carrageenan, wherein the alginate, carboxymethyl cellulose, hyaluronate chitosan, carrageenan, ι-carrageenan and λ-carrageenan are each optionally oxidized, wherein the alginate, carboxymethyl cellulose, hyaluronate chitosan, κ-carrageenan, ι-carrageenan and λ-carrageenan optionally include one or more groups selected from the group consisting of methacrylate, acrylate, acrylamide, methacrylamide, thiol, hydrazine, tetrazine, norbornene, transcyclooctene and cyclooctyne. In another embodiment, the second polymer is alginate. In still another embodiment, the alginate is oxidized alginate. In yet another embodiment, the alginate comprises a mixture of a high molecular weight alginate and a low molecular weight alginate. In one embodiment, the ratio of the high molecular weight alginate to the low molecular weight alginate is about 5:1 to about 1:5. In another embodiment, the ratio of the high molecular weight alginate to the low molecular weight alginate is about 1:1.

In one embodiment of various aspects of the invention, the second polymer network comprises a second polymer that is ionically crosslinked with an ionic crosslinking agent selected from the group consisting of CaCl$_2$, CaSO$_4$, $CaCO_3$, hyaluronic acid, and polylysine. In another embodiment, the ionic crosslinking agent is $CaSO_4$.

In one embodiment of various aspects of the invention, the first polymer network and the second polymer network are covalently coupled.

In one embodiment, the IPN hydrogel hydrogel composition or the adhesive composition is biodegradable. In another embodiment, the IPN hydrogel composition or the adhesive composition is biocompatible.

In one embodiment of various aspects of the invention, the adhesive polymer is a high density primary amine polymer. In another embodiment, the high density primary amine polymer is chitosan.

In one embodiment of various aspects of the invention, the adhesive polymer layer is attached to the IPN via a coupling agent. In another embodiment, the coupling agent comprises a first carboxyl activating agent. In still another embodiment, the first carboxyl activating agent is a carbodiimide. In yet another embodiment, the carbodiimide is selected from the group consisting of 1-ethyl-3-(3-dimethylaminopropyl)carbodiimide (EDC, EDAC or EDCI), dicyclohexylcarbodiimide (DCC) and diisopropylcarbodiimide (DIC). In still another embodiment, the coupling agent further comprises a second carboxyl activating agent. In one embodiment, the second carboxyl activating agent is selected from the group consisting of N-hydroxysuccinimide (NHS), N-hydroxysulfosuccinimide (sulfo-NHS), hydroxybenzotriazole (HOBt), dimethylaminopyridine (DMAP), Hydroxy-3,4-dihydro-4-oxo-1,2,3-benzotriazine (HOOBt/HODhbt), 1-Hydroxy-7-aza-1H-benzotriazole (HOAt), Ethyl 2-cyano-2-(hydroximino)acetate, Benzotriazol-1-yloxy-tris(dimethylamino)-phosphonium hexafluorophosphate (BOP), Benzotriazol-1-yloxy-tripyrrolidino-phosphonium hexafluorophosphate, 7-Aza-benzotriazol-1-yloxy-tripyrrolidinophosphonium hexafluorophosphate), Ethyl cyano(hydroxyimino)acetato-02)-tri-(1-pyrrolidinyl)-phosphonium hexafluorophosphate, 3-(Diethoxy-phosphoryloxy)-1,2,3-benzo[d] triazin-4(3H)-one, 2-(1H-Benzotriazol-1-yl)-N,N,N',N'-tetramethylaminium tetrafluoroborate/hexafluorophosphate, 2-(6-Chloro-1H-benzotriazol-1-yl)-N,N,N',N'-tetramethylaminium hexafluorophosphate), N-[(5-Chloro-1H-benzotriazol-1-yl)-dimethylamino-morpholino]-uronium hexafluorophosphate N-oxide, 2-(7-Aza-1H-benzotriazol-1-yl)-N,N,N',N'-tetramethylaminium hexafluorophosphate, 1-[1-(Cyano-2-ethoxy-2-oxoethylideneaminooxy)-dimethylamino-morpholino]-uronium hexafluorophosphate, 2-(1-Oxy-pyridin-2-yl)-1,1,3,3-tetramethylisothiouronium tetrafluoroborate, Tetramethylfluoroformamidinium hexafluorophosphate, N-Ethoxycarbonyl-2-ethoxy-1,2-dihydroquinoline, 2-Propanephosphonic acid anhydride, 4-(4,6-Dimethoxy-1,3,5-triazin-2-yl)-4-methyl-morpholinium salts, bis-Trichloromethylcarbonate, and 1,1'-Carbonyldiimidazole.

In one embodiment of various aspects of the invention, the IPN hydrogel further comprises a pharmaceutically acceptable excipient. In one embodiment, the pharmaceutically acceptable excipient comprises poloxamer 188 (P188), polyvinylpyrrolidone (PVP), and hydroxypropyl cellulose (HPC), or a combination thereof.

In one aspect, the present invention provides a drug delivery system. The drug delivery system comprises the composition according to any embodiment of various aspects of the invention and an additional drug delivery device. In one embodiment, the additional drug delivery device comprises a controlled delivery formulation. In another embodiment, the additional delivery device comprises a scaffold based delivery device, a microsphere based delivery device, a liposome, a microsphere, a silica microparticle based drug delivery device, a nanoparticle, a polymer-drug conjugate, a polyplex, or a micelle. In yet another embodiment, the additional drug delivery device is encapsulated or embedded in the composition according to any embodiment of various aspects of the invention.

In one aspect, the present invention provides a method of treating a disease, a disorder, or a condition in a subject. The method comprises administering a composition according to any embodiment of various aspects of the invention to the subject, thereby treating the disease, the disorder, or the condition in the subject.

In another aspect, the present invention provides a method of treating tissue, or promoting tissue regeneration, or promoting reinnervation in a subject, comprising administering a composition according to any embodiment of various aspects of the invention to the subject, thereby treating tissue, promoting tissue regeneration, or promoting reinnervation in the subject.

In yet another aspect, the present invention provides a method of inducing immunosuppression in a subject, comprising administering a composition according to any embodiment of various aspects of the invention to the subject, thereby inducing immunosuppression in the subject.

In one embodiment of various aspects of the invention, the composition is administered systemically, intravenously, intraperitoneally, intramuscularly, subcutaneously, transcutaneously, percutaneously, transdermally, intraarterially, subdermally, transmucosally, parentally, or topically. In another embodiment, the composition is administered directly at a treatment site in the body of the subject.

In one embodiment of various aspects of the invention, the method comprises subjecting the composition to ultrasound agitation, thermal treatment, enzyme treatment, radiation treatment, or a combination thereof, in order to trigger an on-demand release of the therapeutic agent.

In one embodiment of various aspects of the invention, the disease, disorder, or condition is inflammation. In another embodiment, the disease, disorder, or condition is tissue degeneration. In still another embodiment, the disease, disorder, or condition is muscle or tendon degeneration. In yet another embodiment, the disease, disorder, or condition is an autoimmune disease. In one embodiment, the autoimmune disease is selected from the group consisting of gout, systemic lupus erythematosus, rheumatoid arthritis, and psoriasis.

In one embodiment of various aspects of the invention, the tissue is selected from skin tissue, muscle tissue, tendon tissue, ligament tissue, bone tissue, nerve tissue, connective tissue, bursa tissue, adipose tissue, or a combination thereof.

In one aspect, the present invention provides a method of reducing friction between a first side of a first tissue and a second side. The method comprises applying an adhesive composition to the first side, wherein the adhesive composition comprises an interpenetrating networks (IPN) hydrogel, comprising a first polymer network and a second polymer network; and an adhesive polymer layer attached to a first surface of the IPN hydrogel; wherein the first polymer network comprises a first polymer that is covalently cross-linked and the second polymer network comprises a second polymer that is ionically crosslinked; wherein the adhesive polymer layer contacts the first side and a second surface of the IPN hydrogel contacts the second side; thereby reducing the friction between the first side and the second side.

In another aspect, the present invention provides a method of protecting a first side of a first tissue from a second side or promoting the recovery of the first tissue. The method comprises applying an adhesive composition to the first tissue, wherein the adhesive composition comprises an interpenetrating networks (IPN) hydrogel, comprising a first polymer network and a second polymer network; and an adhesive polymer layer attached to a first surface of the IPN hydrogel; wherein the first polymer network comprises a first polymer that is covalently crosslinked and the second polymer network comprises a second polymer that is ionically crosslinked; wherein the adhesive polymer layer contacts the first side of the first tissue and a second surface of the IPN hydrogel contacts the second side; wherein the method reduces the friction between the first side of the first tissue and second side, thereby protecting the first tissue from the second side or promoting the recovery of the first tissue.

In one embodiment of various aspects of the invention, the tissue is selected from the group consisting of skin tissue, muscle tissue, tendon tissue, ligament tissue, bone tissue, nerve tissue, connective tissue, bursa tissue, and adipose tissue. In another embodiment, the second side is a side of a second tissue or a medical device. In still another embodiment, the medical device is selected from a group consisting of an implant, a catheter, a mesh, and a plate. In another embodiment, the adhesive composition is selected from the group consisting of the adhesive composition according to any embodiment of various aspects of the invention.

In one embodiment of various aspects of the invention, the adhesive composition further comprises a lubricant that reduces the friction between the second surface of the IPN hydrogel and the second side. In one embodiment, the lubricant is selected from the group consisting of surface-active phospholipid, lubricin, hyaluronic acid (HA), collagen, proteoglycan, and carboxymethyl cellulose (CMC) fluids.

8

Figure 2A:
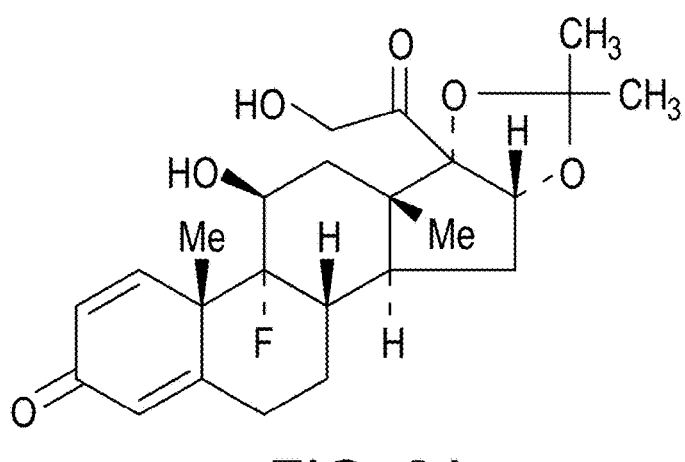
FIG. 2A shows the chemical structure of triamcinolone acetonide (CORT).

FIG. 2K is a graph showing the drug concentration in the Transwell and in the chitosan layer of the CORT-loaded tough gel adhesives (1 mg/ml, 10 mg/ml, or 100 mg/ml CORT in the hydrogel) that are each affixed to the Transwell.

FIG. 2L is a graph showing the percentage of area (of the hydrogel) covered by tough gel adhesives loaded with 1 mg/ml, 10 mg/ml, or 100 mg/ml CORT; FIG. 2M shows the area (of the hydrogel) covered by tough gel adhesives loaded with 1 mg/ml, 10 mg/ml, or 100 mg/ml CORT.

Figure 2B:
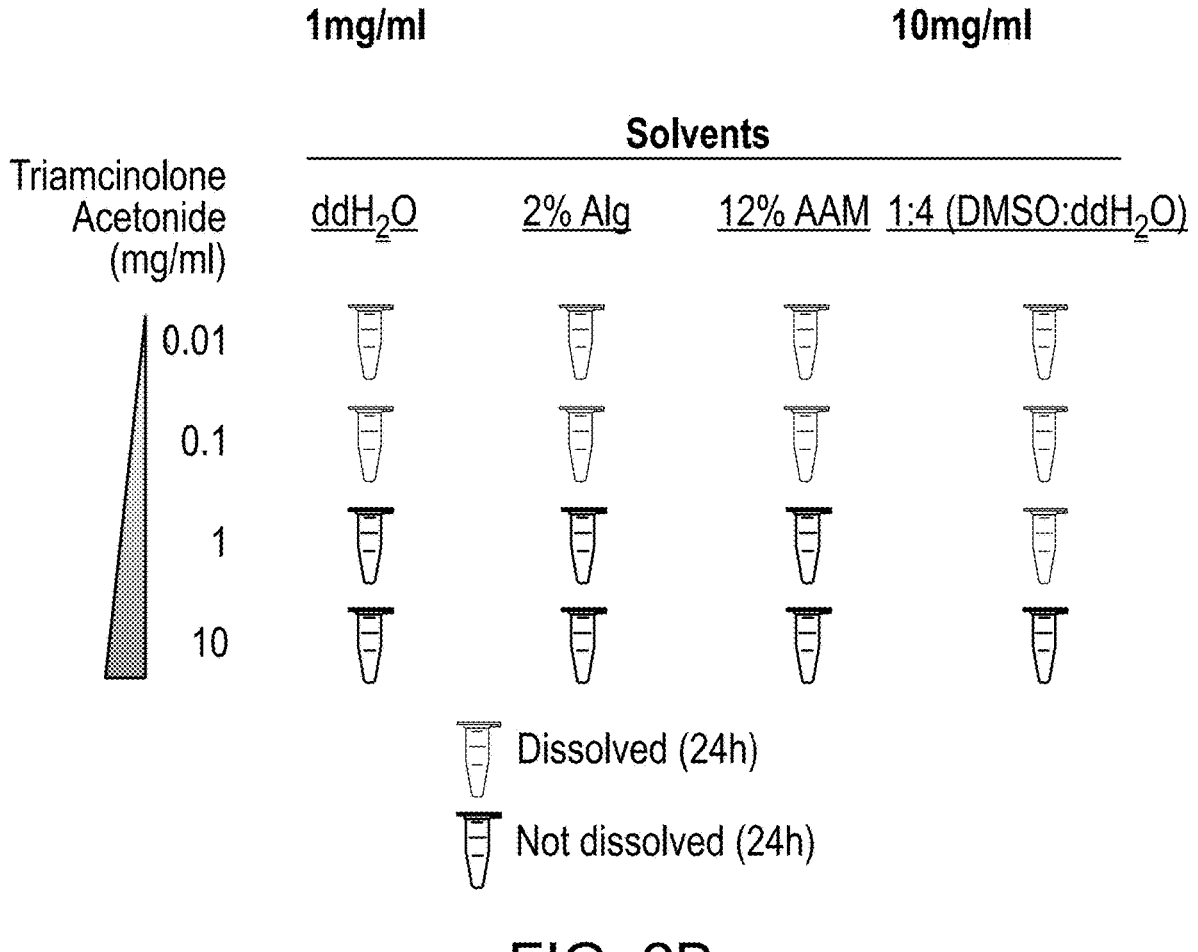
FIG. 2B illustrates the solubility of triamcinolone acetonide in water, 2% alginate, and 12% acrylamide.
Figures 2C, 2D, 2E, 2F:
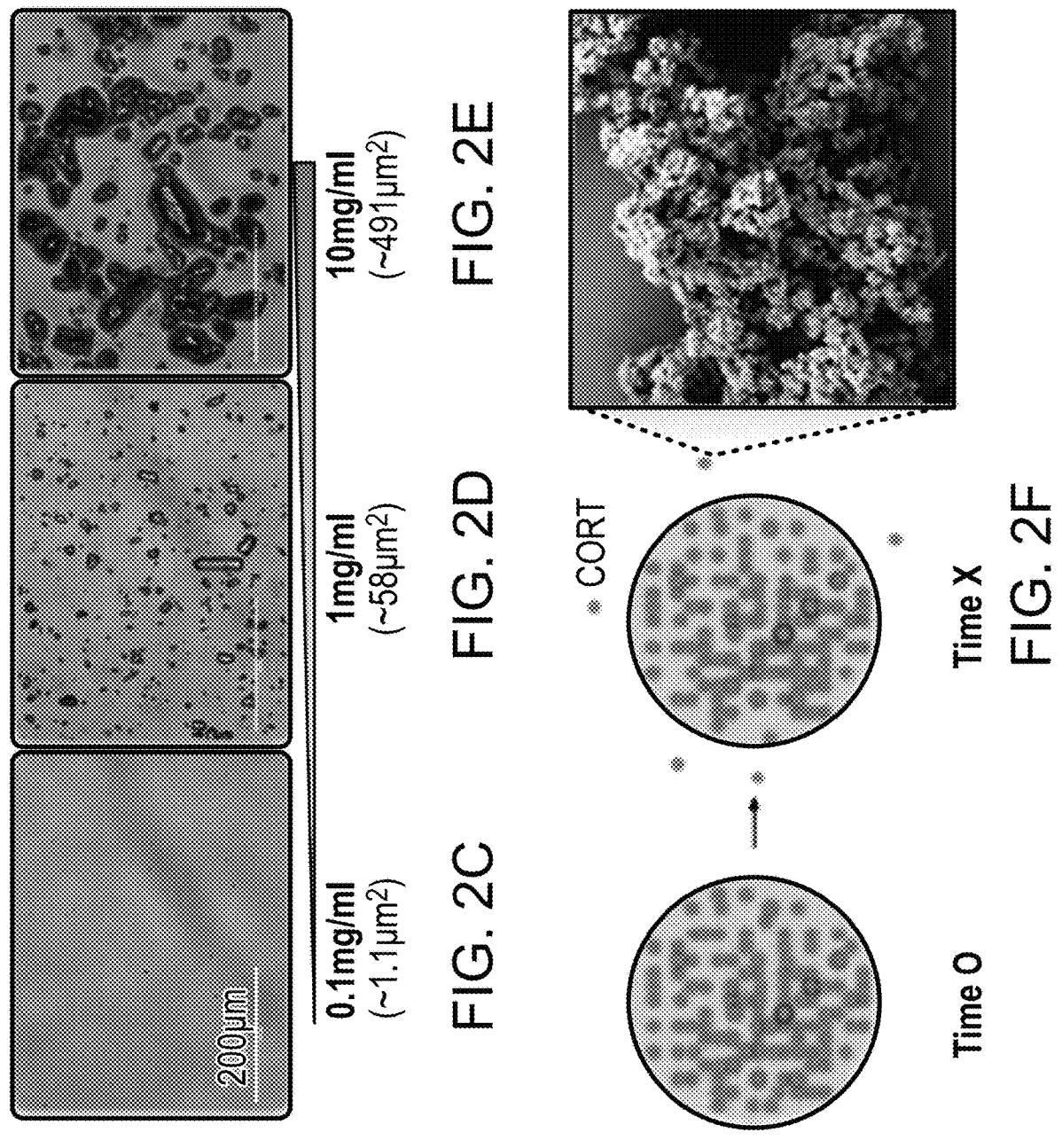
FIGS. 2C, 2D, and 2E are micrographs showing particle aggregation in a solution of 2% alginate and 12% acrylamide at drug loadings above the solubility limit 0.1 mg/ml, 1 mg/ml, and 10 mg/ml triamcinolone acetonide
FIG. 2F illustrates how the dissolution controlled release allows high loading of CORT upon tough gel adhesives.
Figure 2G:
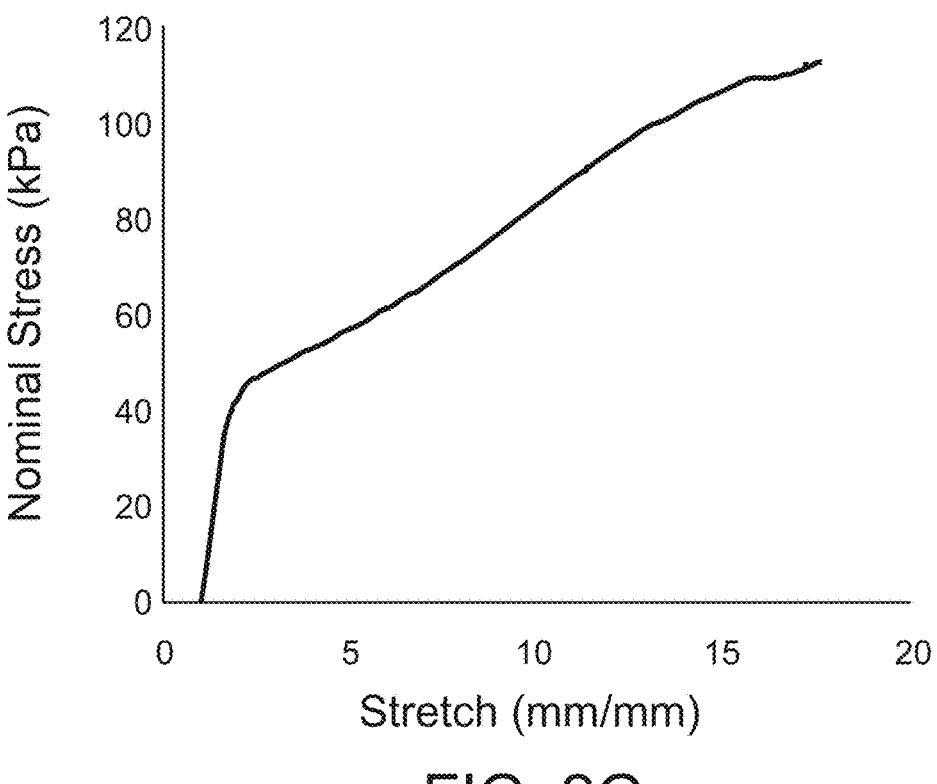
FIG. 2G is a graph showing the nominal stress and maximum stretch for tough gels loaded with 10 mg/ml of CORT, which is not affected by the presence of the drug.
Figure 2H:
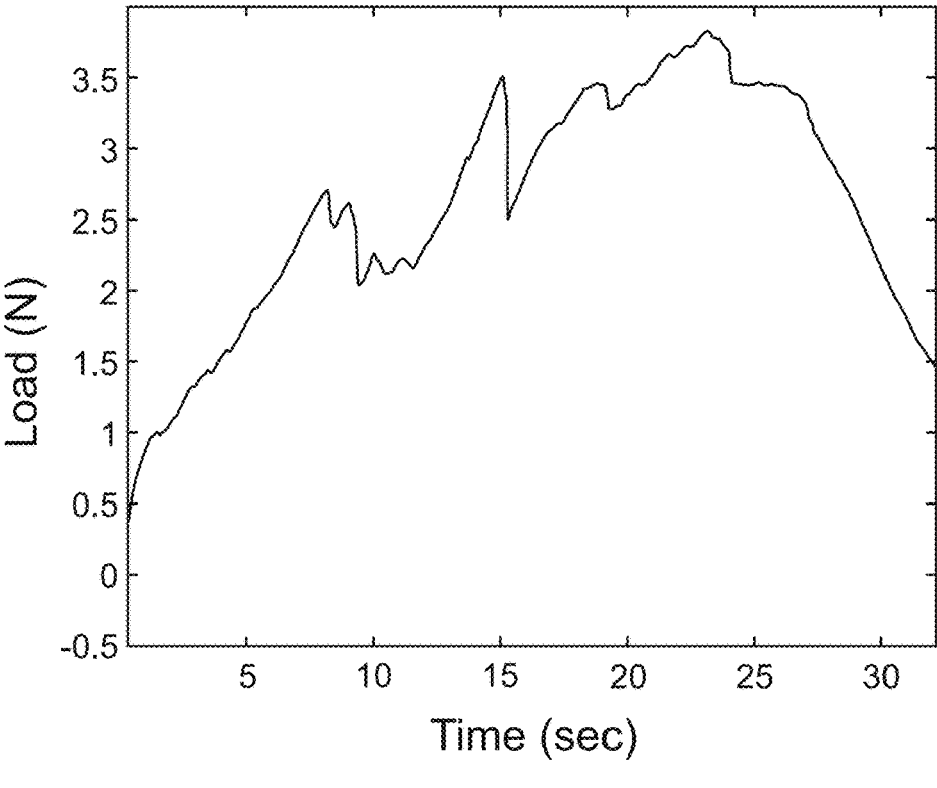
FIG. 2H is a graph showing the load over time for tough gel adhesives loaded with CORT, which is not affected by the presence of the drug.
Figure 2I:
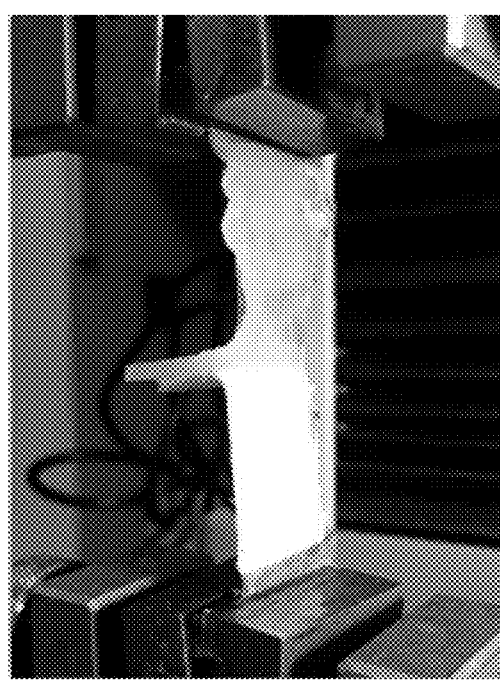
FIG. 2I shows a CORT-loaded tough gel adhesive being tested for adhesiveness.
Figure 2J:
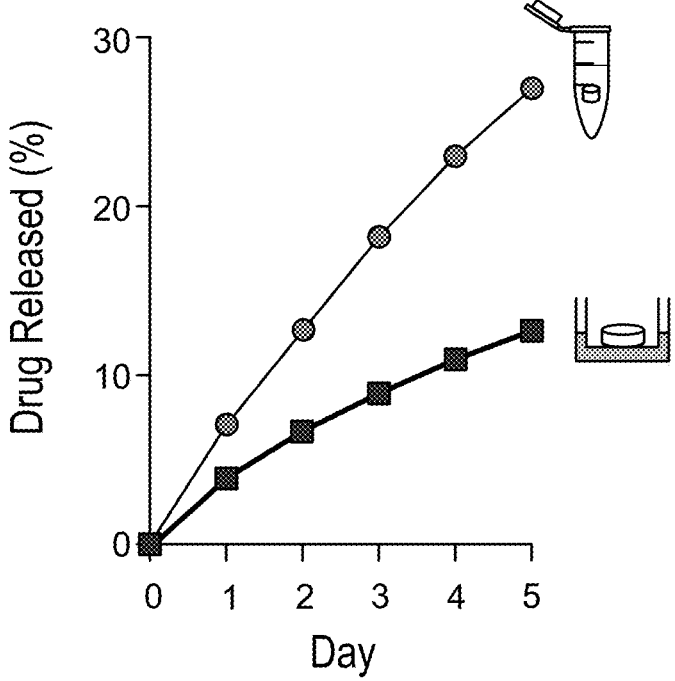
FIG. 2J is a graph showing drug release over time (5 days) for a CORT-loaded tough gel adhesive free floating in an Eppendorf tube and another CORT-loaded tough gel adhesive affixed to a Transwell.
Figure 2N:
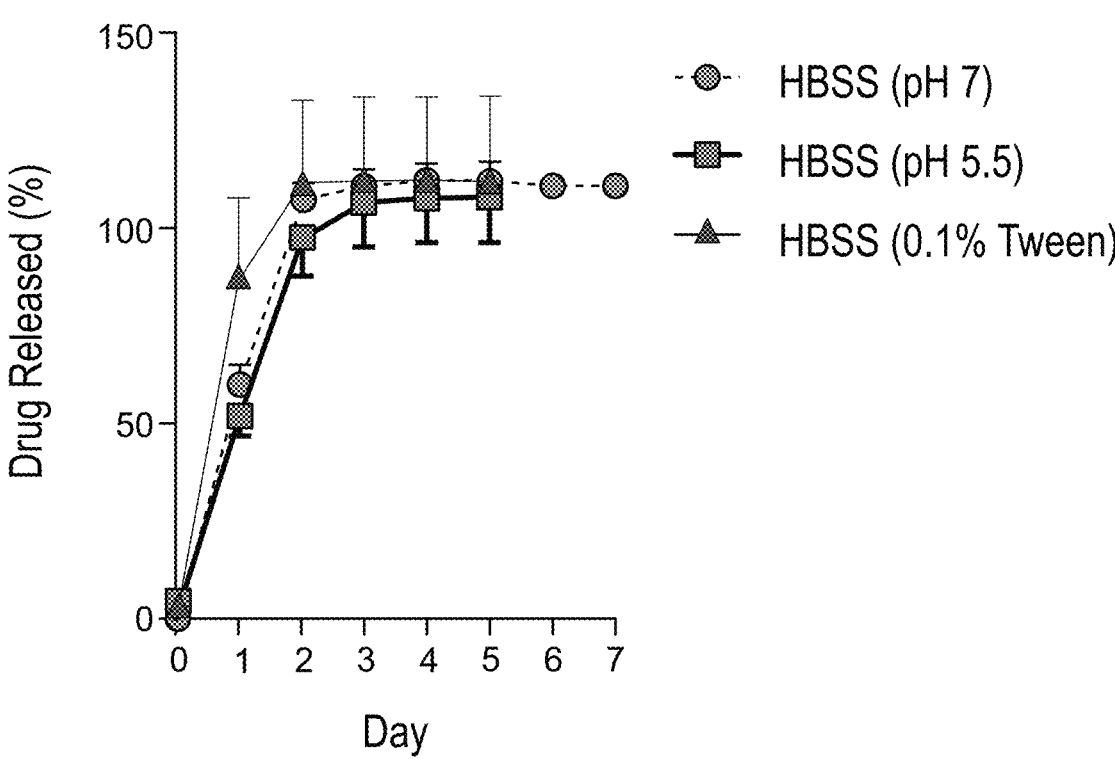

FIG. 2N is a graph showing the drug release over time (7 days) in Hank's balanced salt solution (HBSS) at pH 7.7, at pH 5.5, and with 0.1% Tween.

Figure 2O:
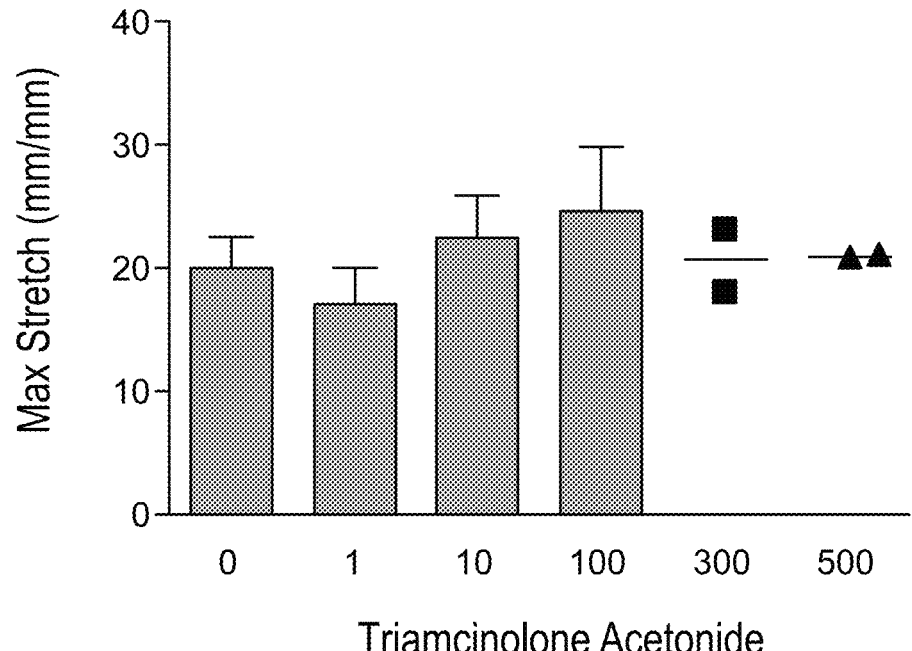

FIG. 2O is a graph showing the maintenance of mechanical properties in CORT-loaded tough gel adhesives with increasing CORT concentrations.

Figure 2P:
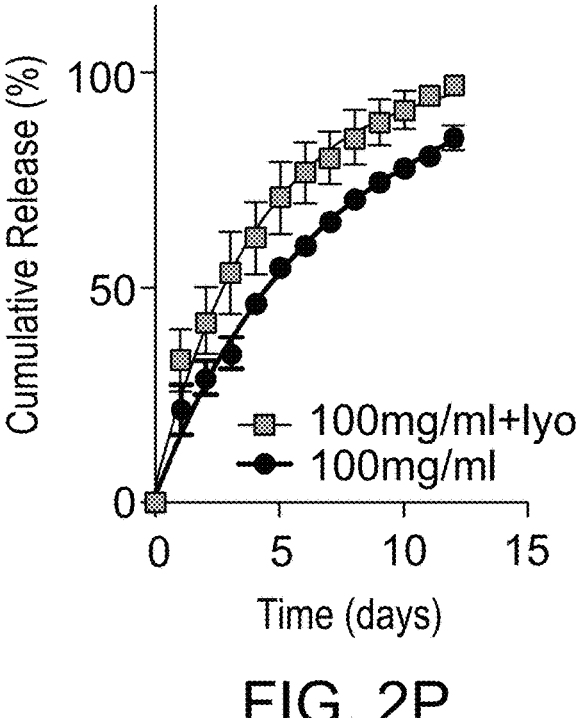

FIG. 2P is a graph showing the cumulative release of 100 mg/ml CORT (lyophilized and un-lyophilized) over time (up to 15 days).

Figures 2Q, 2R, 2S:
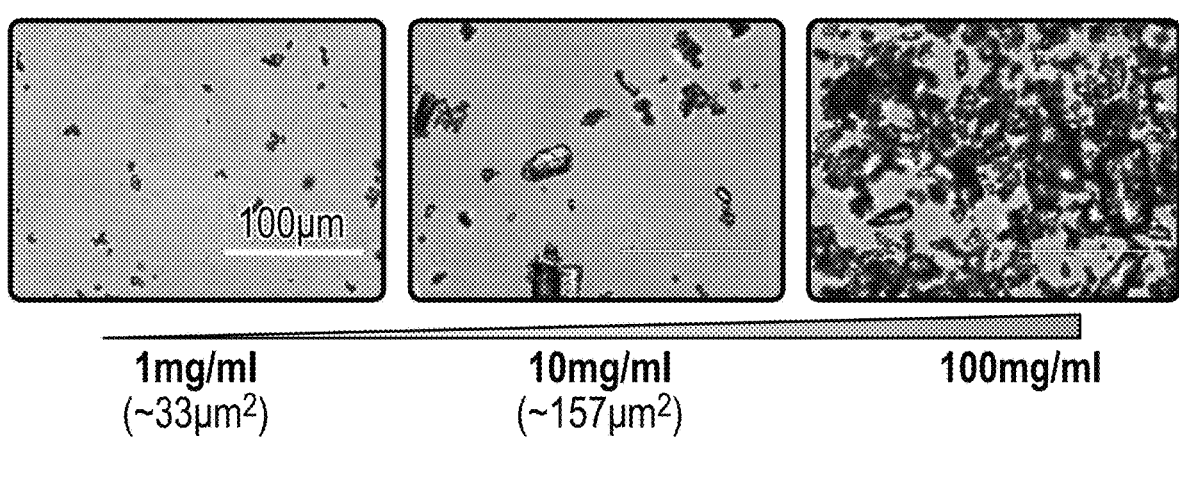

FIGS. 2Q, 2R, and 2S are micrographs of tough gel adhesives loaded with 1 mg/ml, 10 mg/ml, or 100 mg/ml CORT, showing how micronized CORT particles formed aggregates.

Figure 3A:
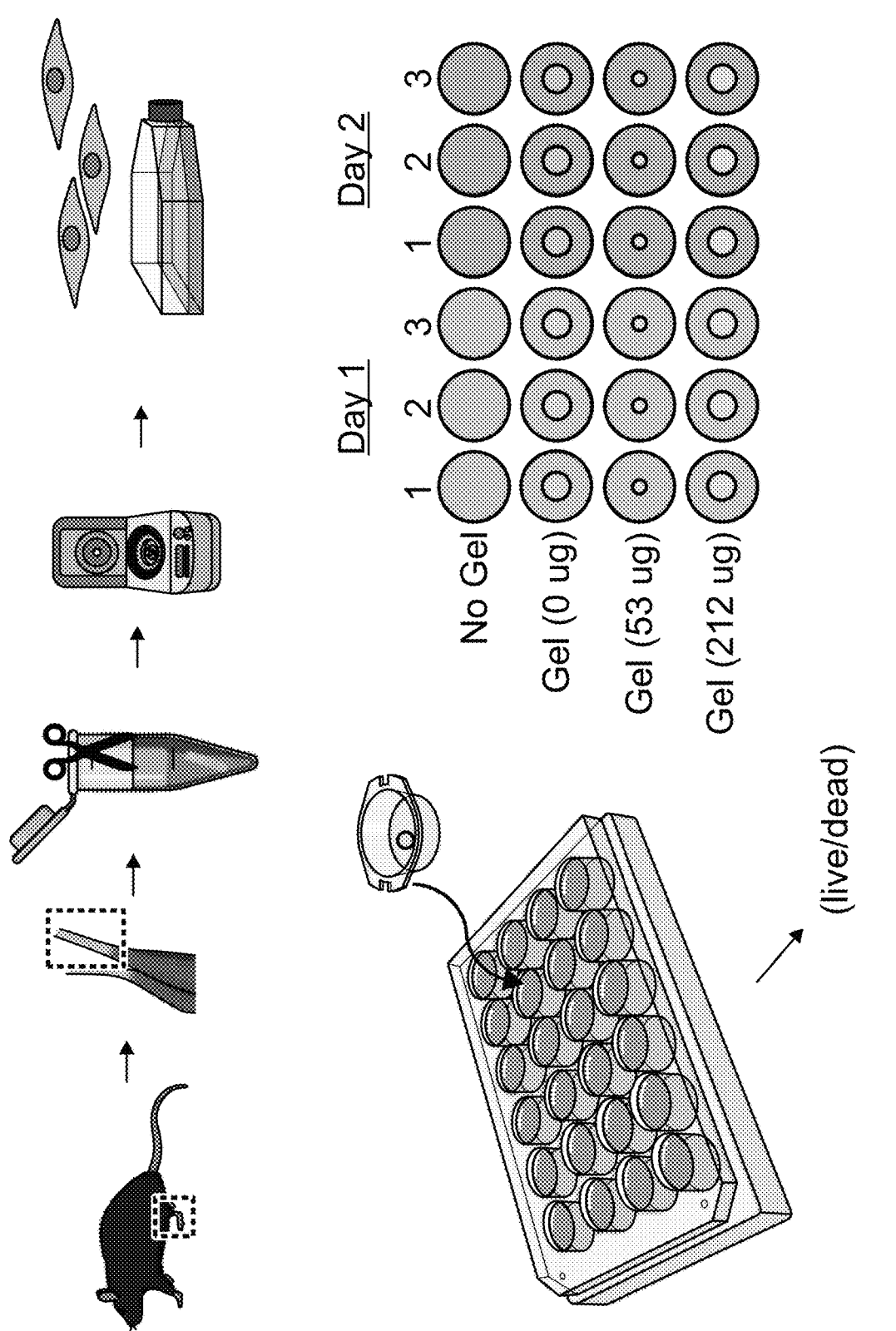
Figure 3B:
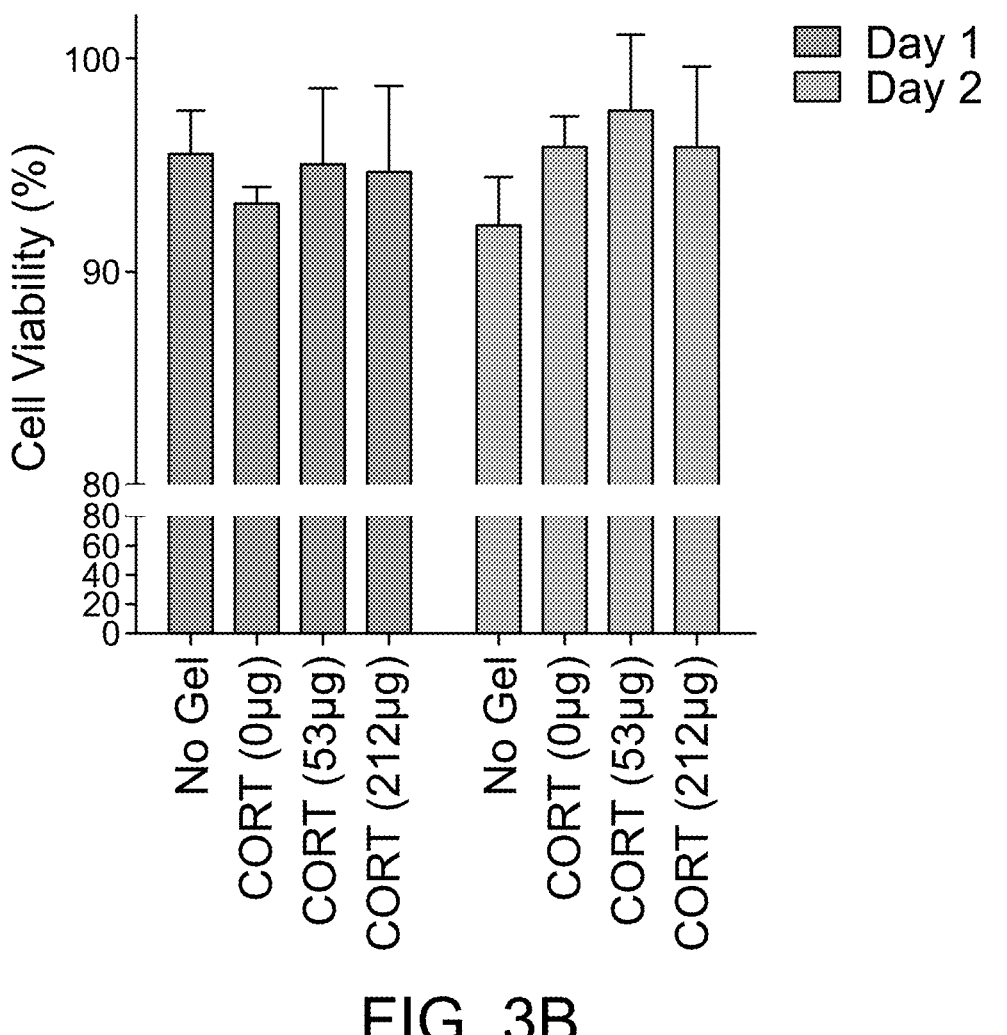

FIGS. 3A and 3B are schematics and a graph depicting cytocompatibility of tendon derived cells with CORT releasing JTAs.

FIG. 3A is schematics depicting that tendon derived cells from the rat Achilles were used. JTAs loaded with CORT were placed in transwells above cultured cells.

FIG. 3B is a graph depicting that cell viability was examined after 1 and 2 days of culture with JTAs releasing CORT.

FIG. 3C shows that tough gel adhesives loaded with 1 mg/ml, 10 mg/ml, or 100 mg/ml CORT, when subcutaneously administered to rats, all allowed controlled release of CORT in vivo.

FIGS. 3D and 3E are graphs showing the compressive modulus of tough gel adhesives loaded with 1 mg/ml, 10 mg/ml, or 100 mg/ml CORT before and after drug release, respectively.

Figures 4A, 4B, 4C, 4D, 4E, 4F, 4G, 4H, 4I, 4J:
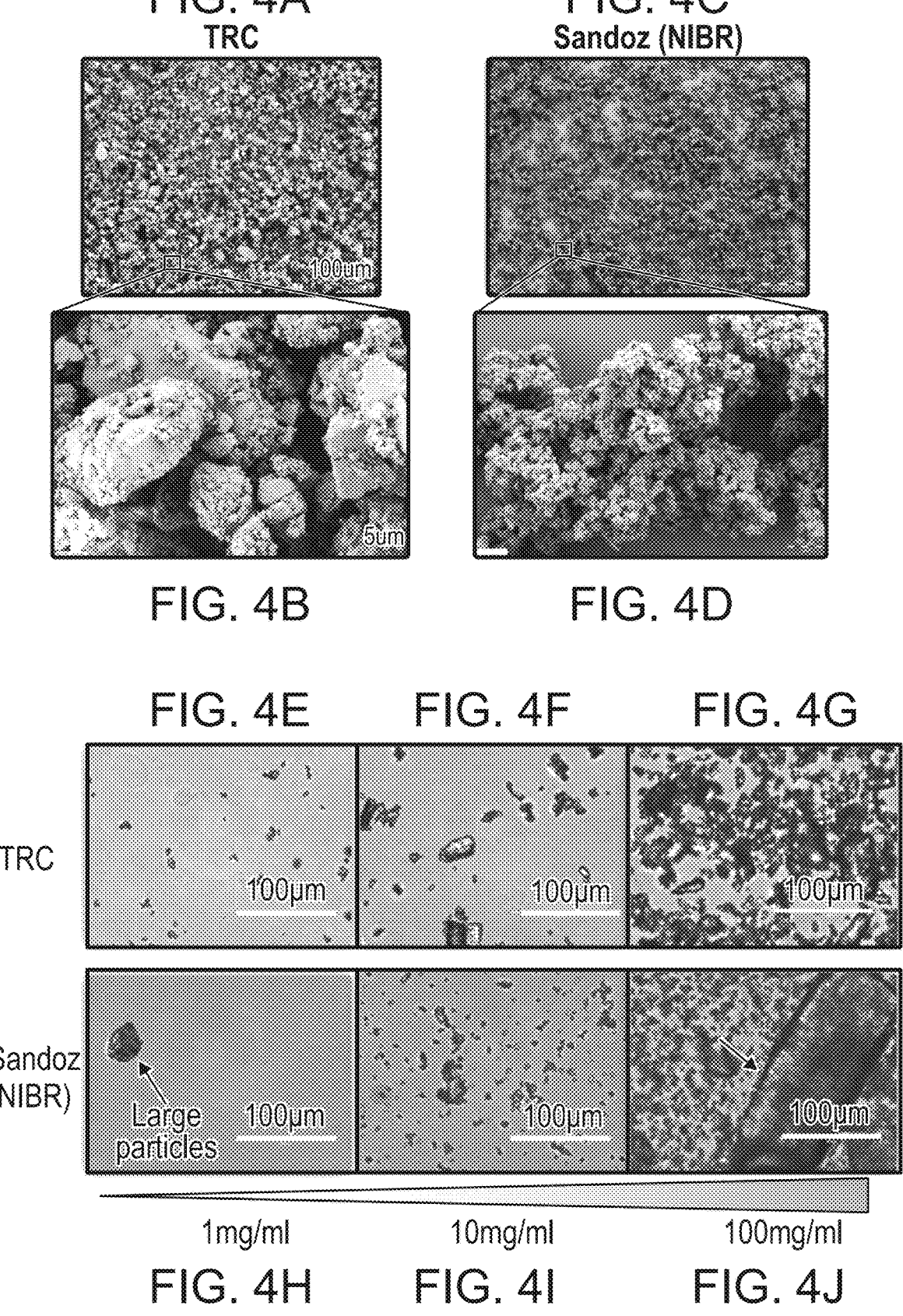

FIG. 4A is an SEM micrograph of the CORT dry powder from supplier Toronto Research Chemicals (TRC).

FIG. 4B is an enlargement of an area of the SEM micrograph of FIG. 4C.

FIG. 4C is an SEM micrograph of the CORT dry powder from another supplier Sandoz (NIBR).

FIG. 4D is an enlargement of an area of the SEM micrograph of FIG. 4E.

FIGS. 4E, 4F, and 4G are micrographs of respectively 1 mg/ml, 10 mg/ml, or 100 mg/ml CORT from TRC in alginate and acrylamide monomer solution.

FIGS. 4H, 4I, and 4J are micrographs of respectively 1 mg/ml, 10 mg/ml, or 100 mg/ml CORT from Sandoz (NIBR) in alginate and acrylamide monomer solution.

FIG. 4K is a graph showing the percentage of area (of the hydrogel) covered by tough gel adhesives loaded with 1 mg/ml, 10 mg/ml, or 100 mg/ml CORT from TRC or Sandoz (NIBR).

FIGS. 4L, 4M, and 4N are micrographs of respectively 1 mg/ml, 10 mg/ml, or 100 mg/ml CORT from TRC in alginate and acrylamide monomer solution, showing the homogeneity of the solutions.

FIGS. 4O, 4P, and 4Q are micrographs of respectively 1 mg/ml, 10 mg/ml, or 100 mg/ml CORT from Sandoz (NIBR) in alginate and acrylamide monomer solution, showing the homogeneity of the solutions.

Figures 4R, 4S:
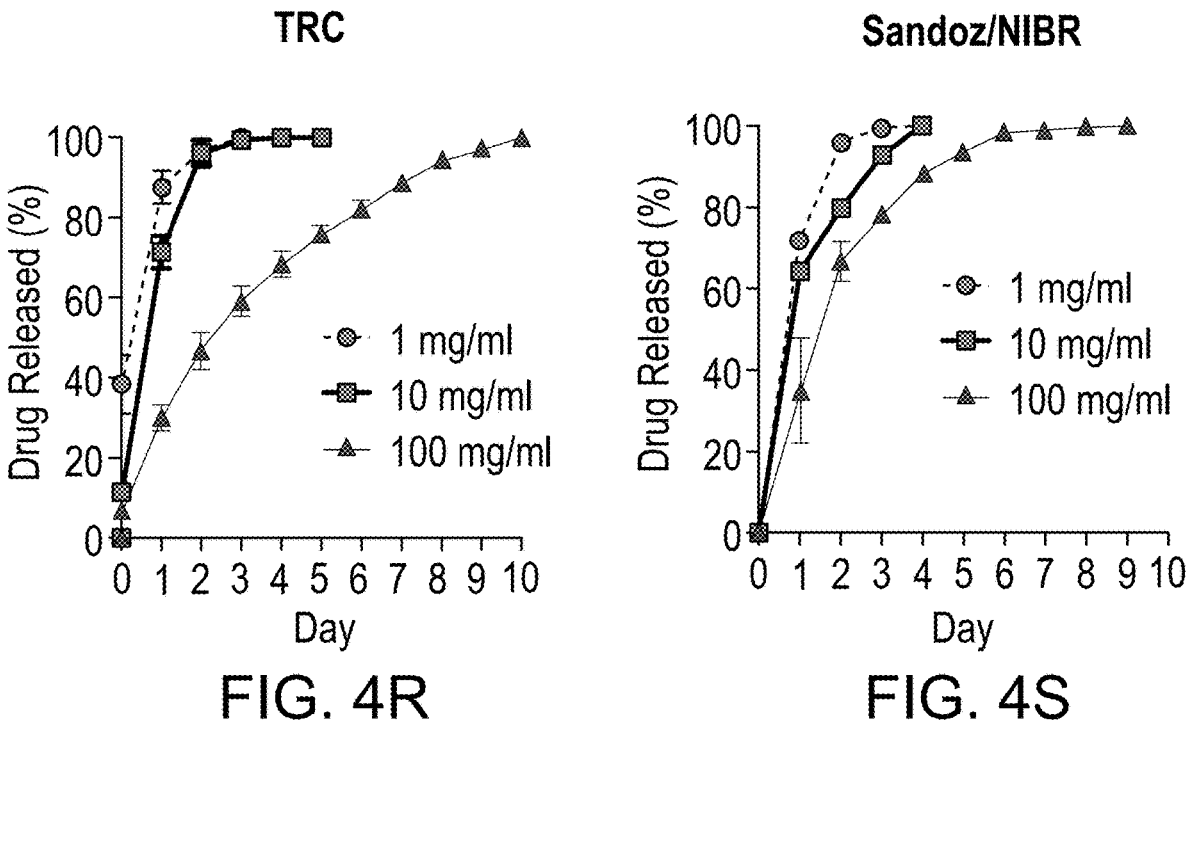

FIGS. 4R and 4S are graphs showing the drug release over time (up to 10 days) from tough gel adhesives loaded with 1 mg/ml, 10 mg/ml, or 100 mg/ml CORT from TRC, or Sandoz (NIBR), respectively.

Figure 4T:
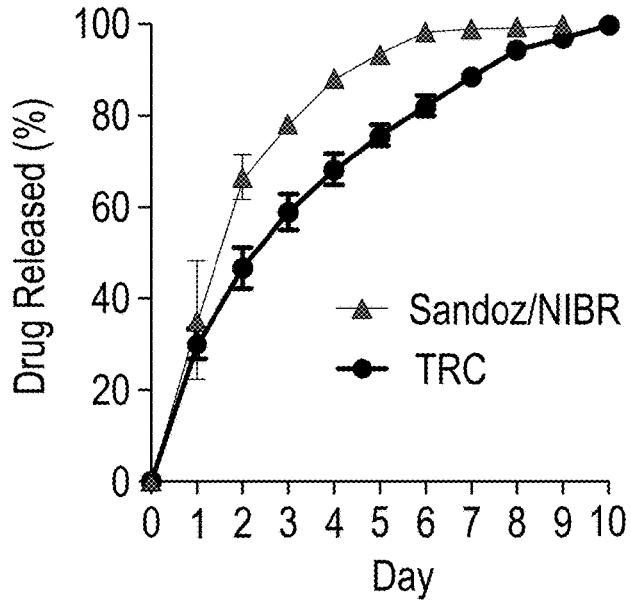

FIG. 4T compares the drug release rate of tough gel adhesives loaded with 100 mg/ml CORT from TRC, or Sandoz (NIBR), respectively.

Figures 4U, 4V, 4W:
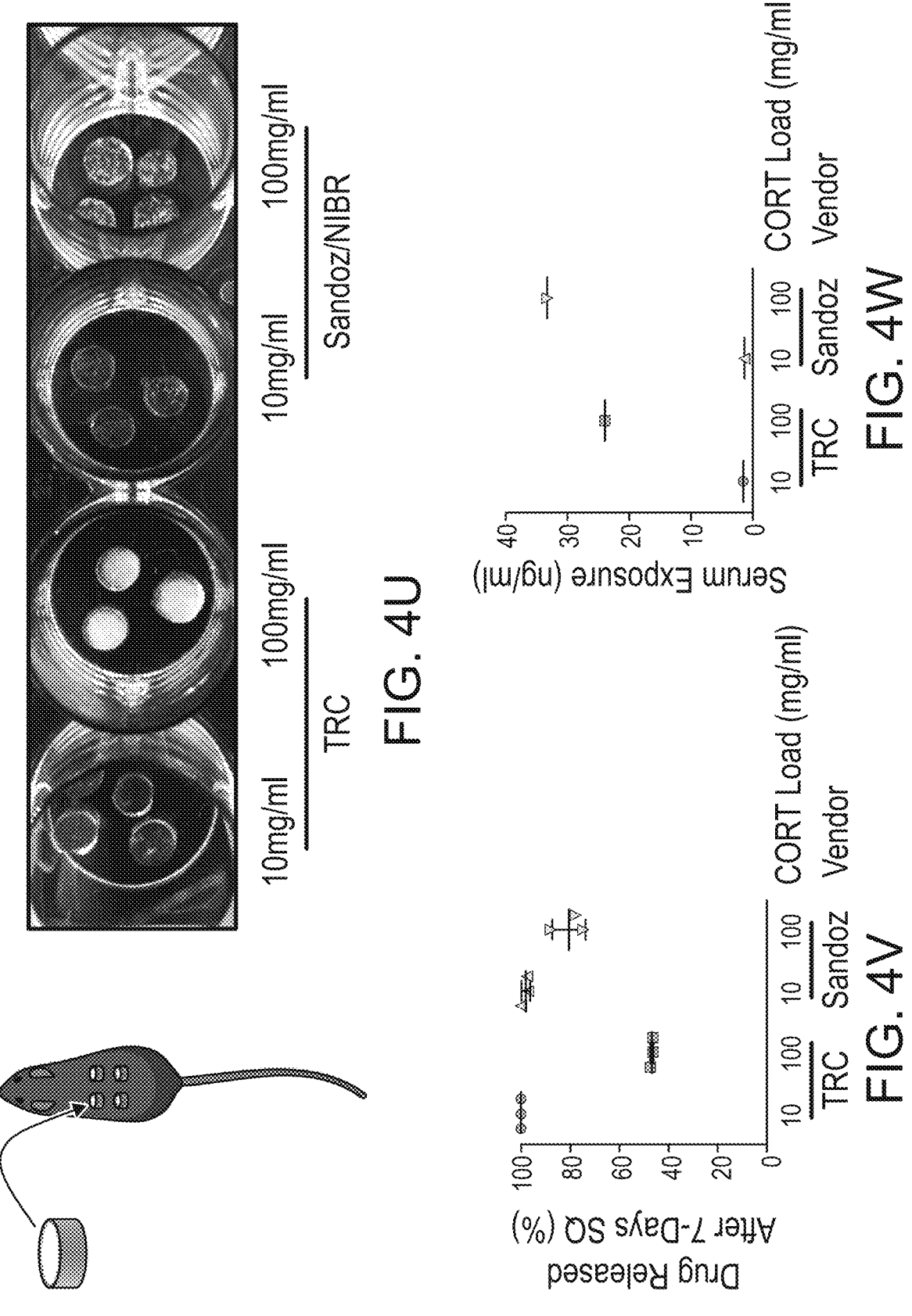

FIG. 4U compares the retention of the drug in tough gel adhesives loaded with 10 mg/ml or 100 mg/ml CORT from TRC, or Sandoz (NIBR), respectively.

FIGS. 4V and 4W are graphs comparing the retention of the drug in tough gel adhesives loaded with 10 mg/ml or 100 mg/ml CORT from TRC, or Sandoz (NIBR), respectively.

FIG. 5A illustrates the effect of increased CORT loading on the stretch of tough gel adhesives. FIG. 5B is a graph depicting the same.

FIG. 5C illustrates the effect of increased CORT loading on the peak stress of tough gel adhesives. FIG. 5D is a graph depicting the same.

FIG. 5E is a graph depicting the effect of increased CORT loading on extended drug release.

FIG. 6A shows the chemical structure of poloxamer 188 (P188). FIGS. 6B and 6C show solutions having 100 mg/ml CORT from Sandoz (NIBR) with increasing amounts of P188, at 1 min and 5 min, respectively. FIGS. 6D and 6E are micrographs of solutions having 100 mg/ml CORT from Sandoz (NIBR) with 0% and 1% P188, respectively.

Figure 7A:
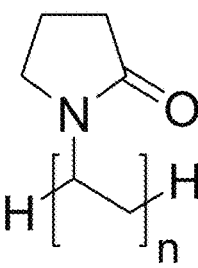
Figure 7B:
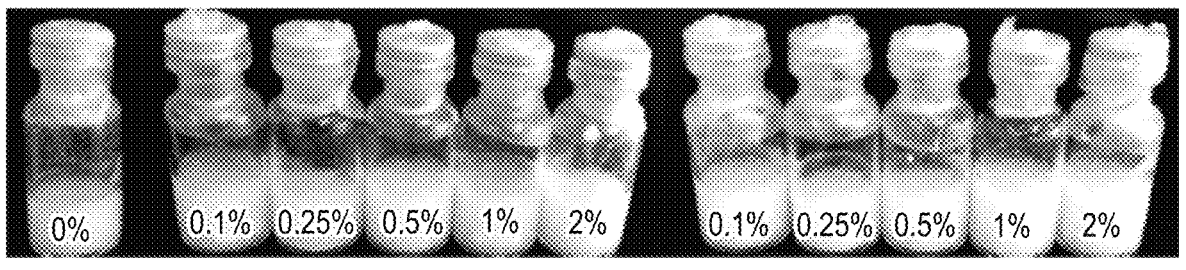
Figures 7C, 7D:
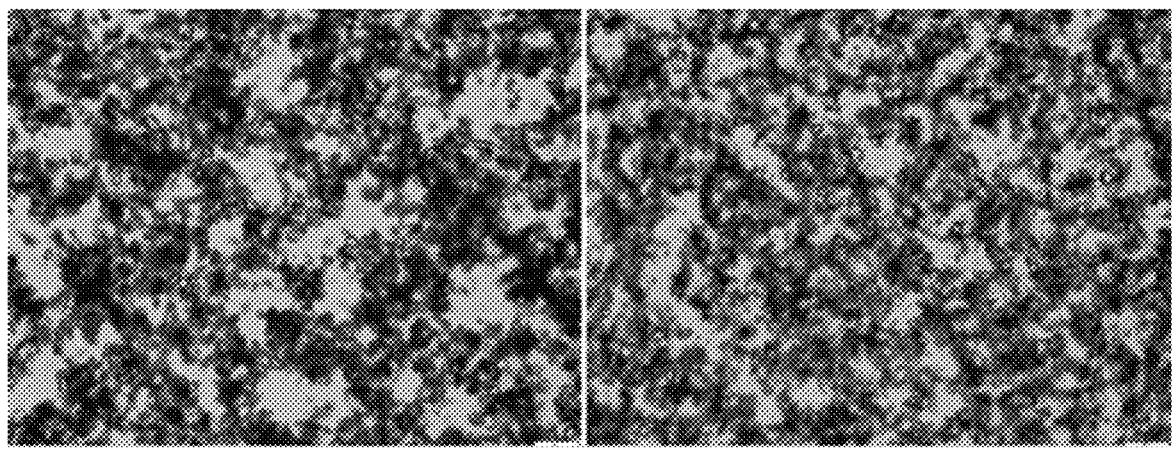

FIG. 7A shows the chemical structure of polyvinylpyrrolidone (PVP). FIG. 7B shows solutions having 100 mg/ml CORT from Sandoz (NIBR) with increasing amounts of PVP, at 1 min and 5 min, respectively. FIGS. 7C and 7D are micrographs of solutions having 100 mg/ml CORT from Sandoz (NIBR) with 0% and 0.2% PVP, respectively.

Figures 8A, 9A, 9B, 9C:
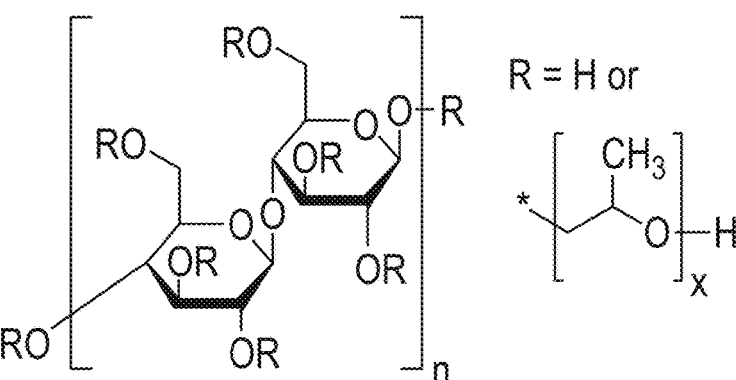

FIG. 8A shows the chemical structure of hydroxypropyl cellulose (HPC). FIGS. 8B, 8C, and 8D are micrographs of solutions having 100 mg/ml CORT from Sandoz (NIBR) with 0%, 0.5%, or 3% HPC, respectively.

FIGS. 9A, 9B, and 9C are graphs showing the effects of 1% P188, 0.2% PVP, or 3% HPC, respectively, on tough gel adhesives loaded with 100 mg/ml CORT from Sandoz (NIBR).

Figures 10A, 10B:
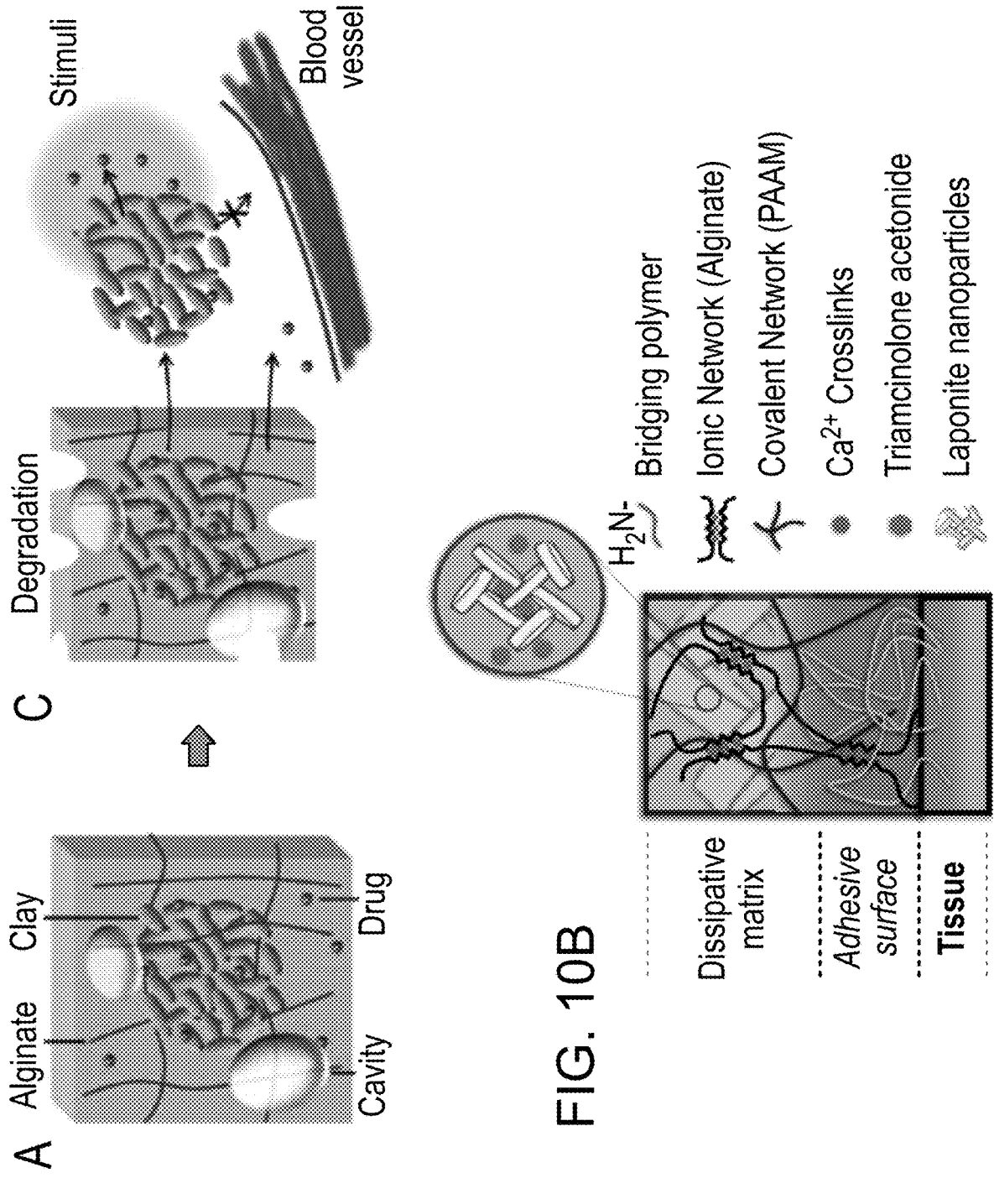

FIGS. 10A and 10B are schematic diagrams illustrating how clay may be incorporated into a tough gel adhesive and how the drug may be released from the material.

FIG. 10C illustrates formation of hydrogen bonds between hydroxyl and carbonyl groups of CORT.

FIGS. 11A, 11B, 11C, 11D, and 11E are micrographs of laponite (LAP) only, mixtures of laponite with 1 mg/ml, 10 mg/ml, or 100 mg/ml CORT, and CORT only, respectively.

Figures 11A, 11B, 11C, 11D, 11E, 12A, 12B:
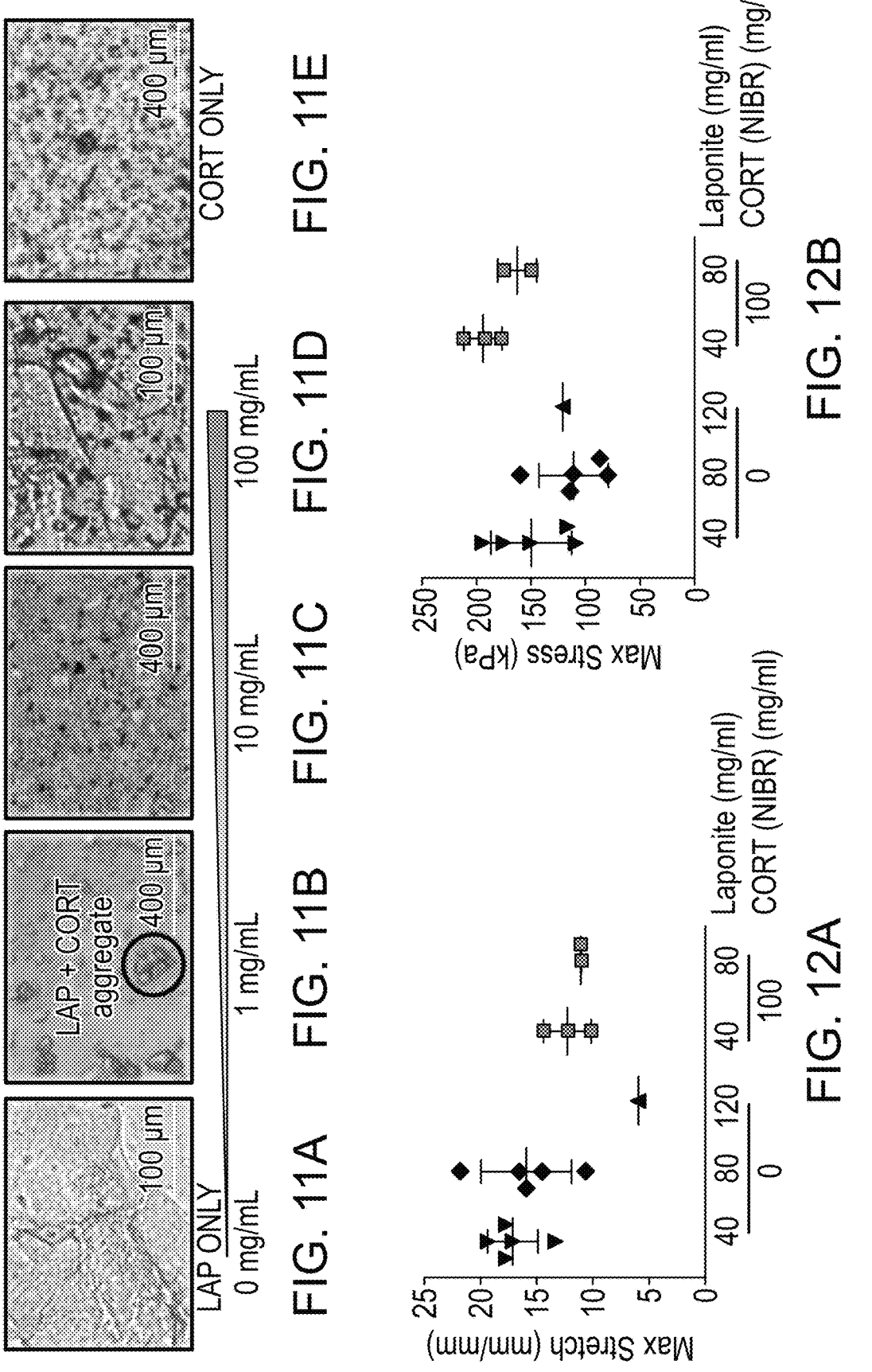

FIGS. 12A and 12B are graphs showing the effects of laponite on maximum stretch and maximum stress, respectively, of tough gel adhesives that are unloaded or loaded with 100 mg/ml CORT from Sandoz (NIBR).

FIG. 13A is a graph showing the electrokinetic potentials (zeta potential) of tough gel adhesives having laponite (LAP) only, CORT only, and different CORT:LAP ratios.

FIGS. 13B and 13C are graphs showing the stretch and stress values of tough gel adhesives having different amounts of laponite.

FIGS. 14A, 14B, and 14C are micrographs of TRC, Sandoz (first batch), and Sandoz (second batch) CORT dry powder, respectively, at 200× magnification.

Figure 14E:
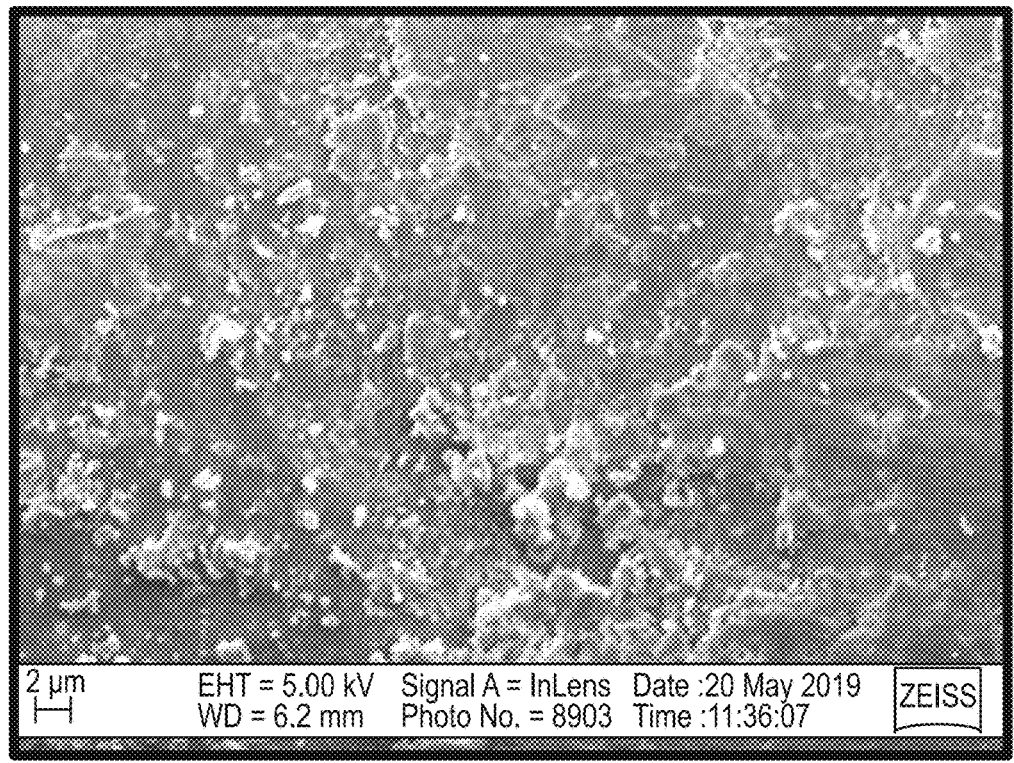
Figure 14F:
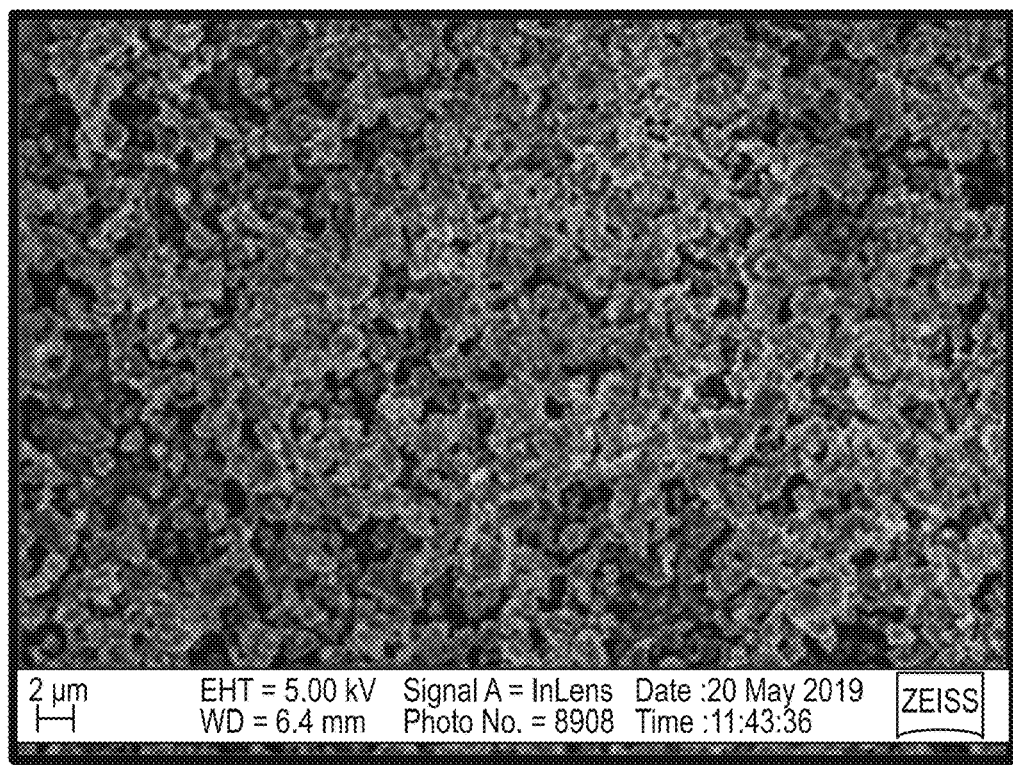

FIGS. 14D, 14E, and 14F are micrographs of TRC, Sandoz (first batch), and Sandoz (second batch) CORT dry powder, respectively, at 200× magnification.

Figures 15A, 15B, 15C, 15D, 15E, 15F:
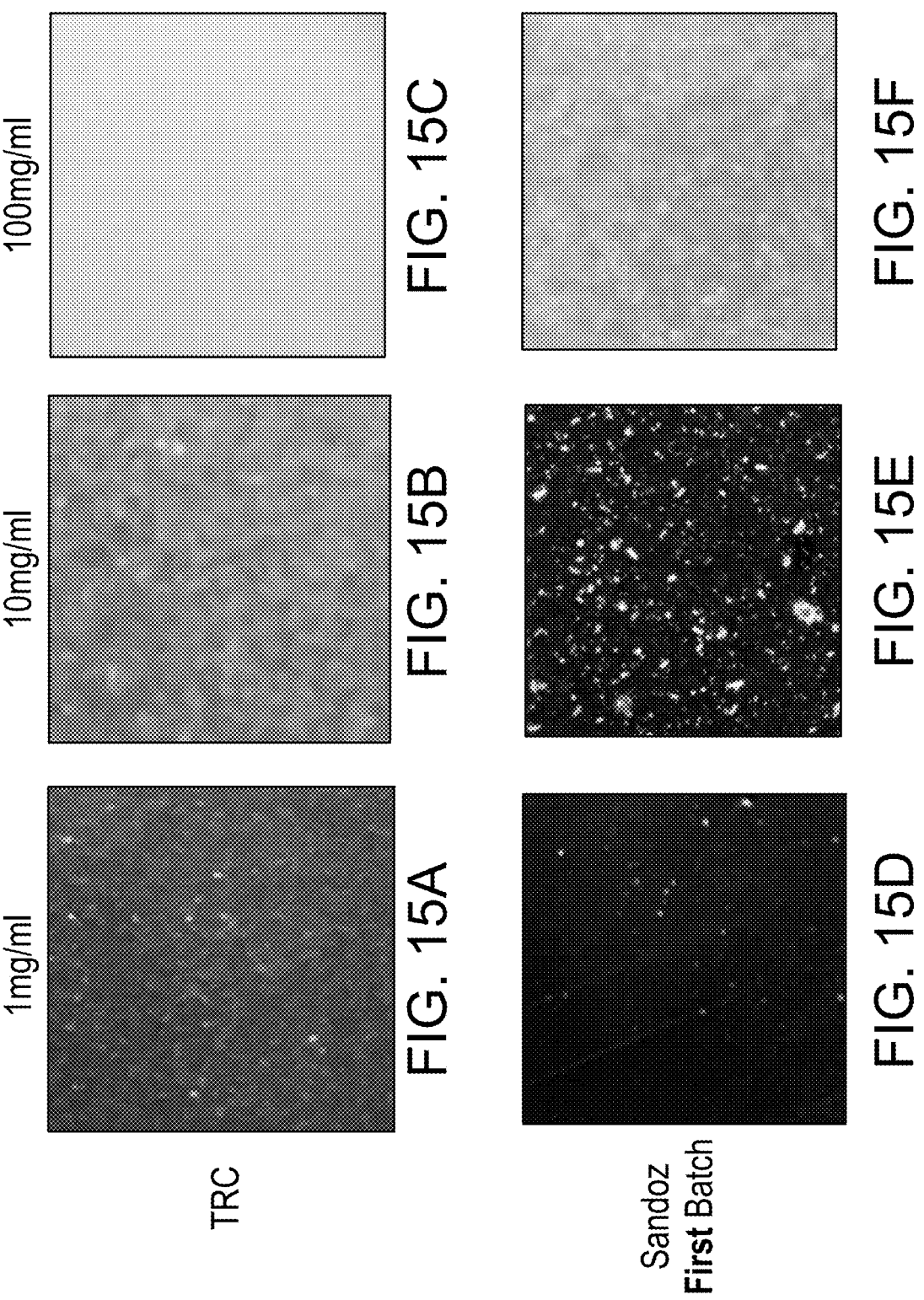

FIGS. 15A, 15B, and 15C are micrographs of tough gel adhesives loaded with 1 mg/ml, 10 mg/ml, or 100 mg/ml CORT from TRC, respectively.

FIGS. 15D, 15E, and 15F are micrographs of tough gel adhesives loaded with 1 mg/ml, 10 mg/ml, or 100 mg/ml CORT from Sandoz (first batch), respectively.

Figures 16A, 16B, 16C, 16D, 16E, 17:
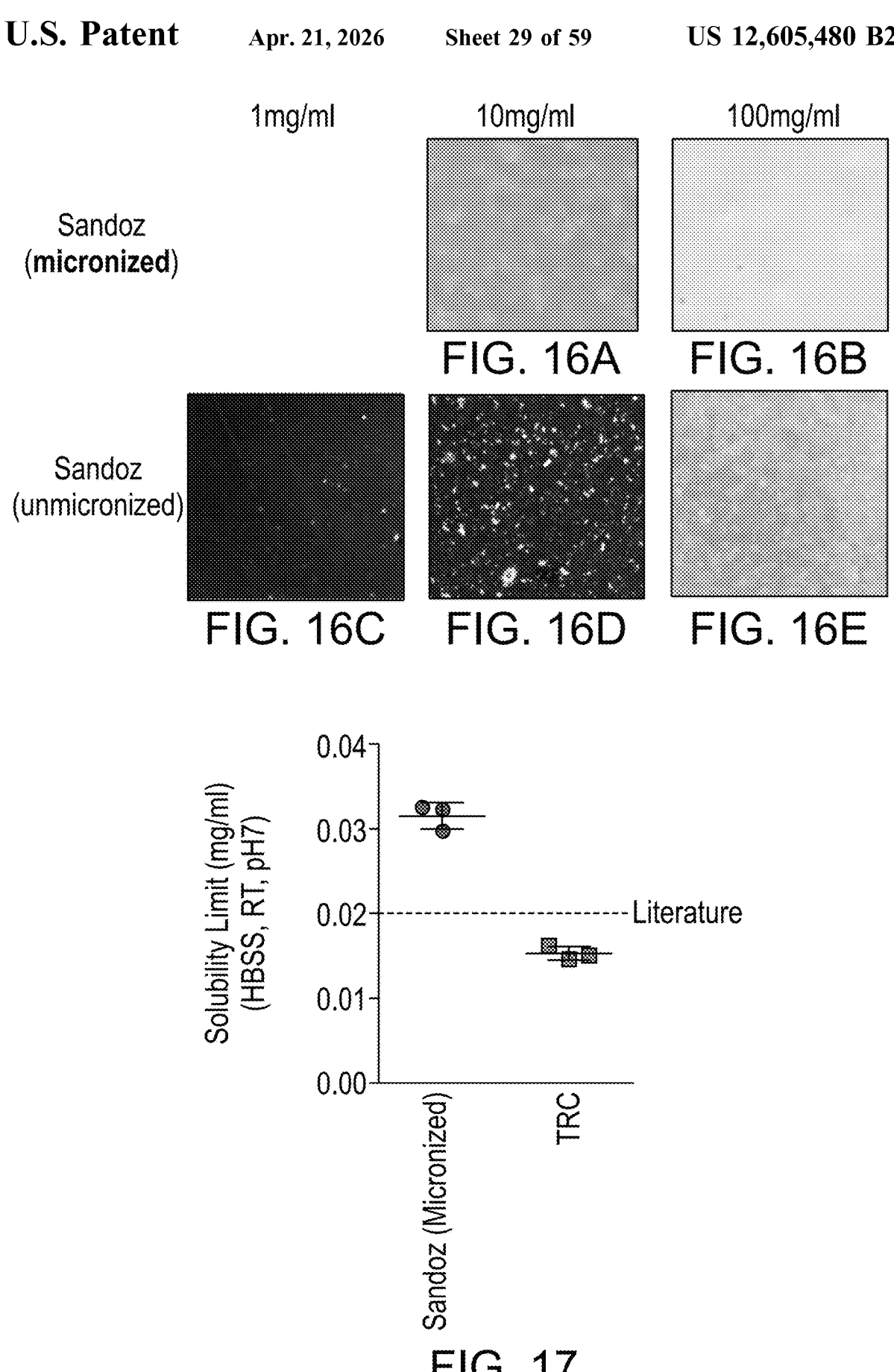

FIGS. 16A and 16B are micrographs of tough gel adhesives loaded with 10 mg/ml or 100 mg/ml micronized CORT from Sandoz, respectively.

FIGS. 16C, 16D, and 16E are micrographs of tough gel adhesives loaded with 1 mg/ml, 10 mg/ml, or 100 mg/ml unmicronized CORT from Sandoz, respectively.

FIG. 17 is a graph comparing the solubility limits of micronized CORT from Sandoz and CORT from TRC.

FIGS. 18A, 18B, and 18C are graphs showing the drug release of tough gel adhesives that are loaded with 1 mg/ml, 10 mg/ml, or 100 mg/ml CORT from Sandoz (NIBR) and either 4% laponite (40 mg/ml laponite).

FIG. 19A is a schematic diagram illustrating the 5-day drug release study design of tough gel adhesives that have been and have not been initially subject to ultrasonication.

FIG. 19B shows the effects of ultrasonication in reducing hydrogel size. FIG. 19C is a graph depicting the same.

FIG. 19D is a graph showing the cumulative release of CORT over 5 days, with or without ultrasonication.

Figure 19E:
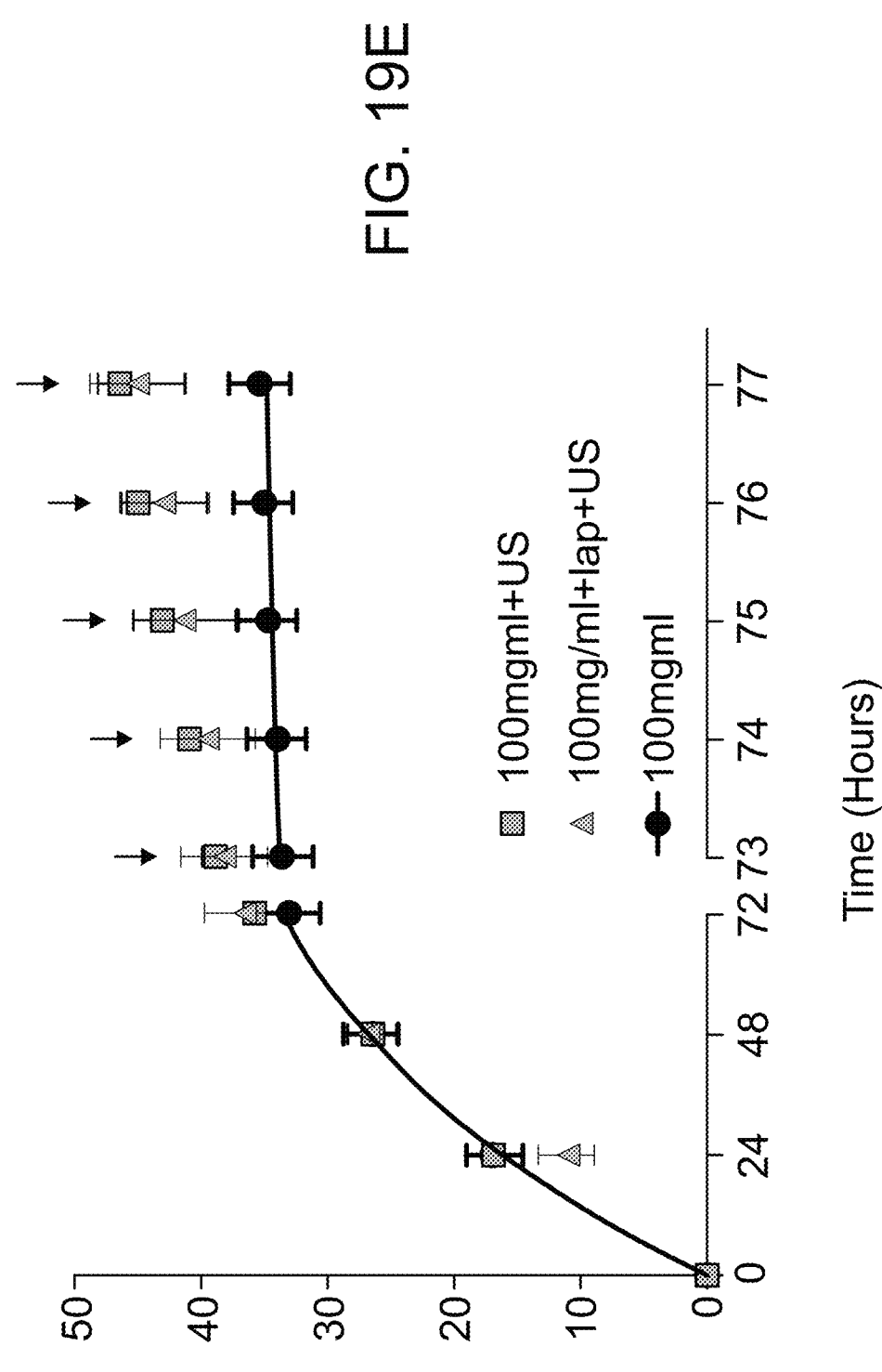

FIG. 19E is a graph showing cumulative CORT release of tough gel adhesives loaded with 100 mg/ml CORT, with laponite and ultrasonication, or with ultrasonication.

Figures 20A, 20B, 20C:
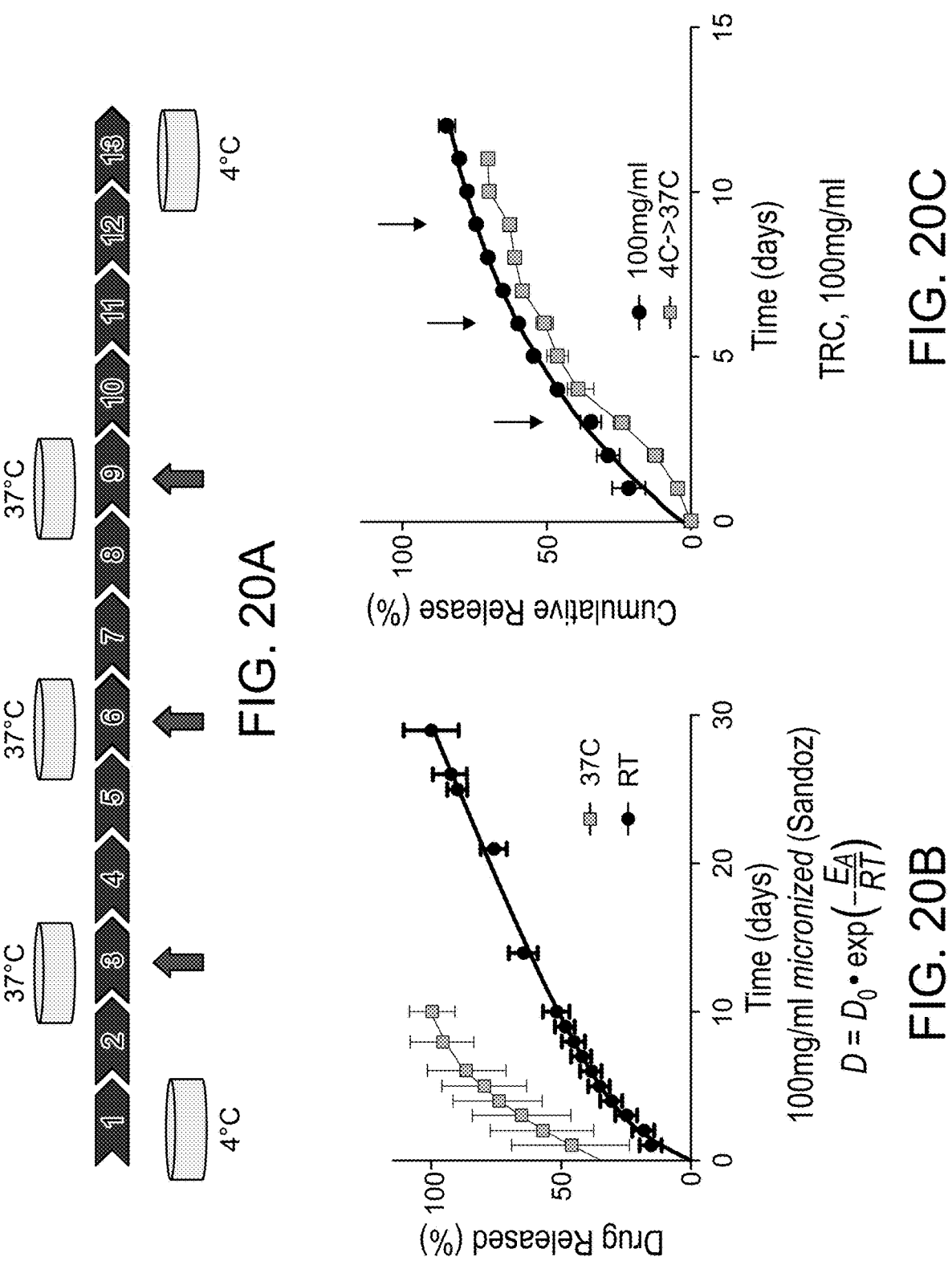

FIGS. 20B and 20C are graphs showing drug released or cumulative release of tough gel adhesives loaded with 100 mg/ml CORT that are incubated at 4° C. but subject to heating at 37° C. on days 3, 6, and 9. FIG. 20A shows the heat studies experimental design.

Figure 21A:
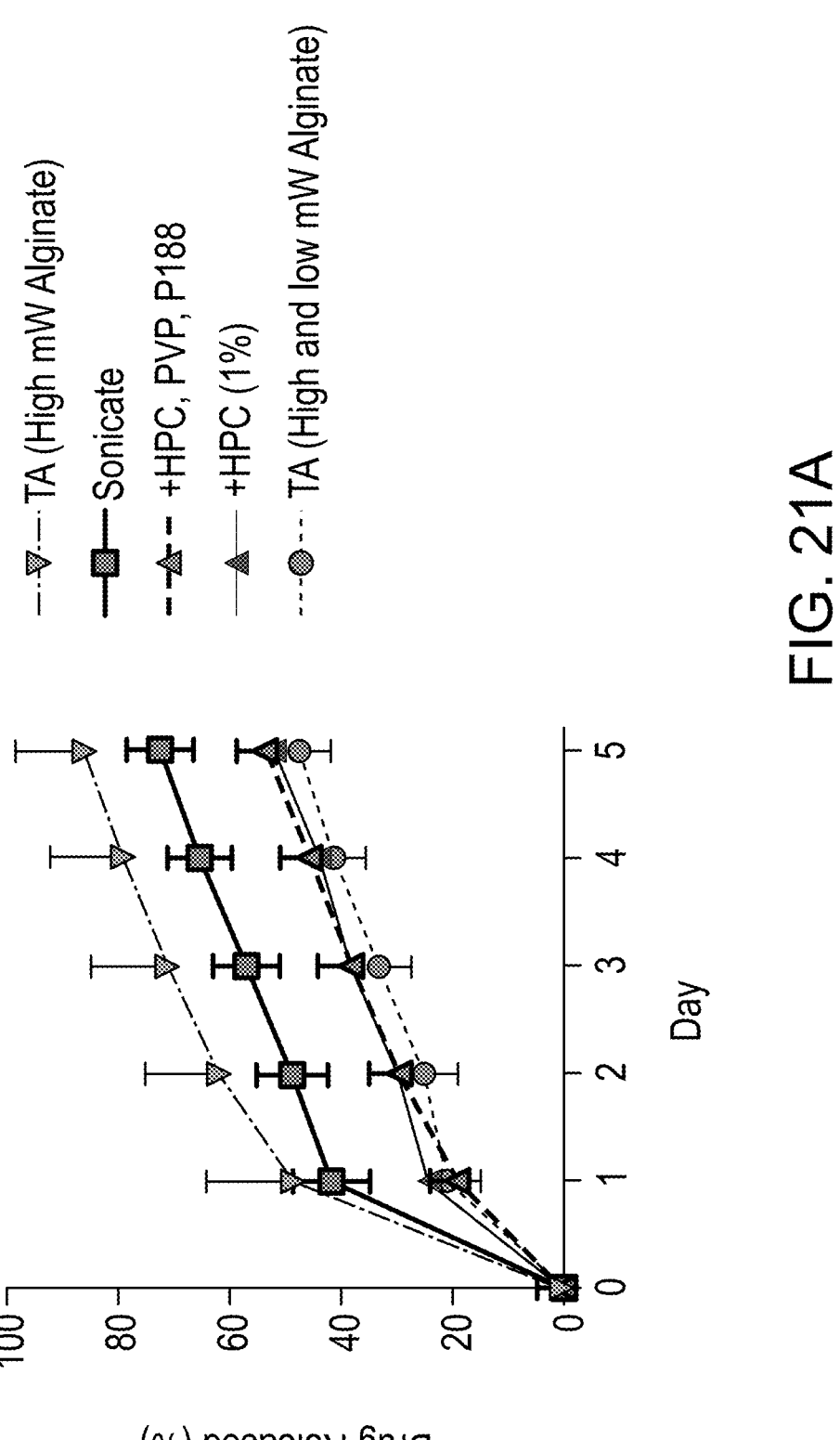

FIG. 21A is a graph showing effects of different conditions (high/low molecular alginate, presence of HPC/PVP/P188, presence of HPC, sonication) on drug release rate.

Figure 21B:
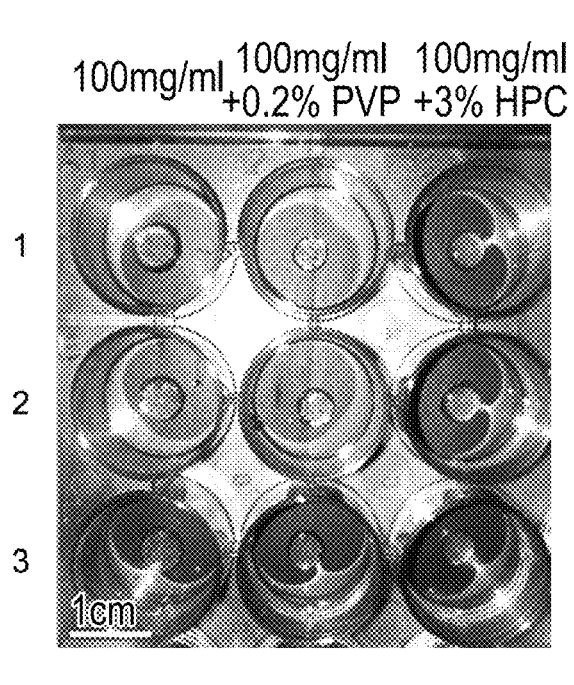
Figure 21C:
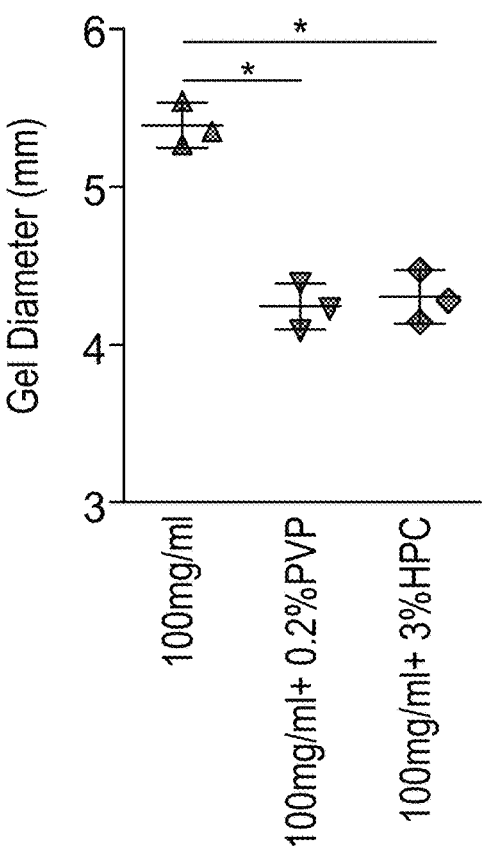

FIG. 21B shows the effects of the presence of 0.2% PVP or 3% HPC on tough gel adhesives loaded with 100 mg/ml CORT. FIG. 21C is a graph depicting the same.

Figure 21D:
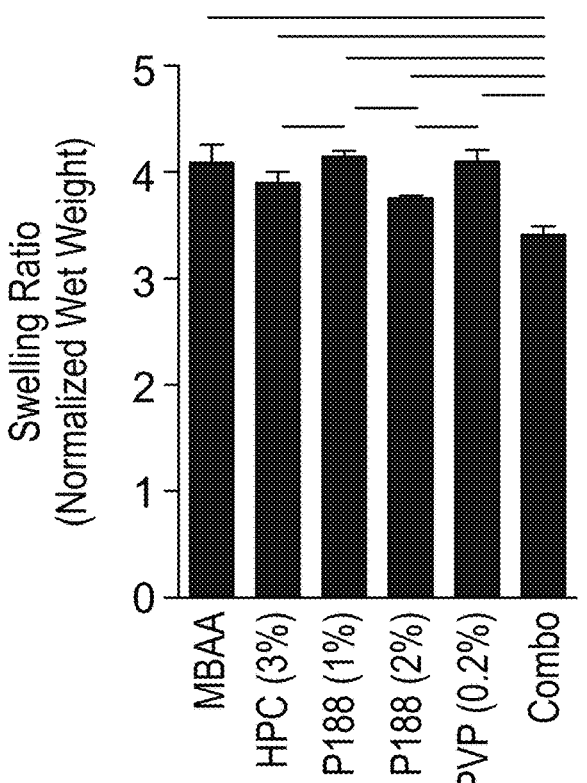

FIG. 21D is a graph showing the effects of the presence of 0.2% PVP, 1% P188, 2% P188, 3% HPC, or a combination of all three refining agents, on gel swelling.

Figure 22A:
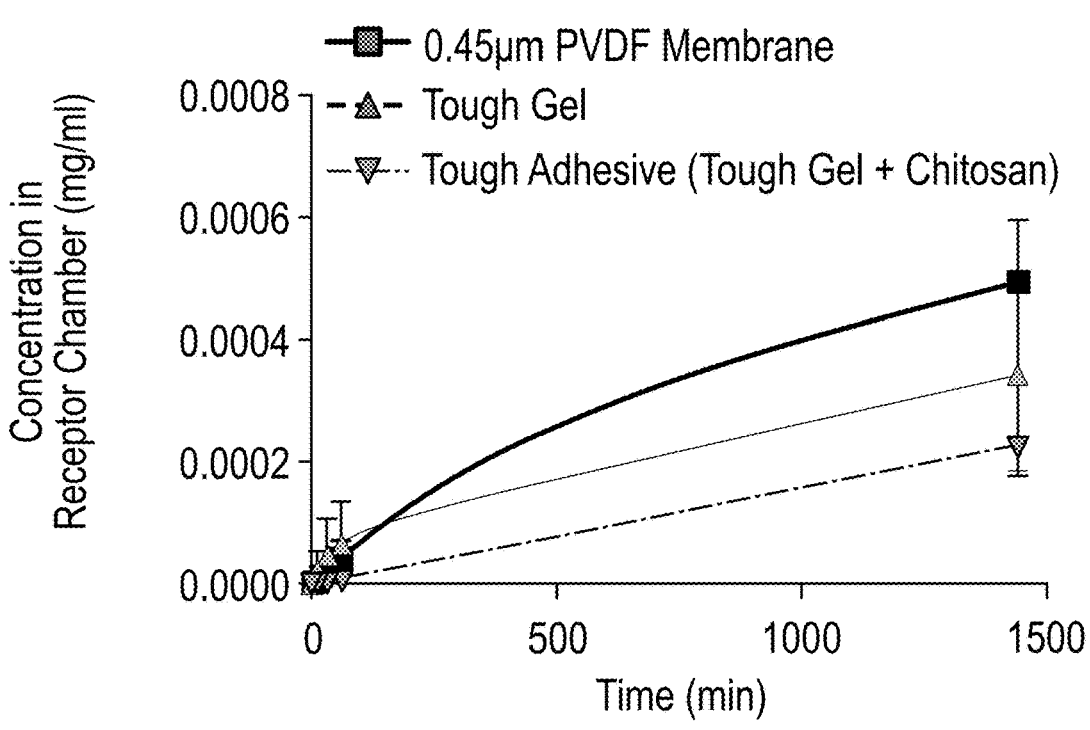
Figure 22B:
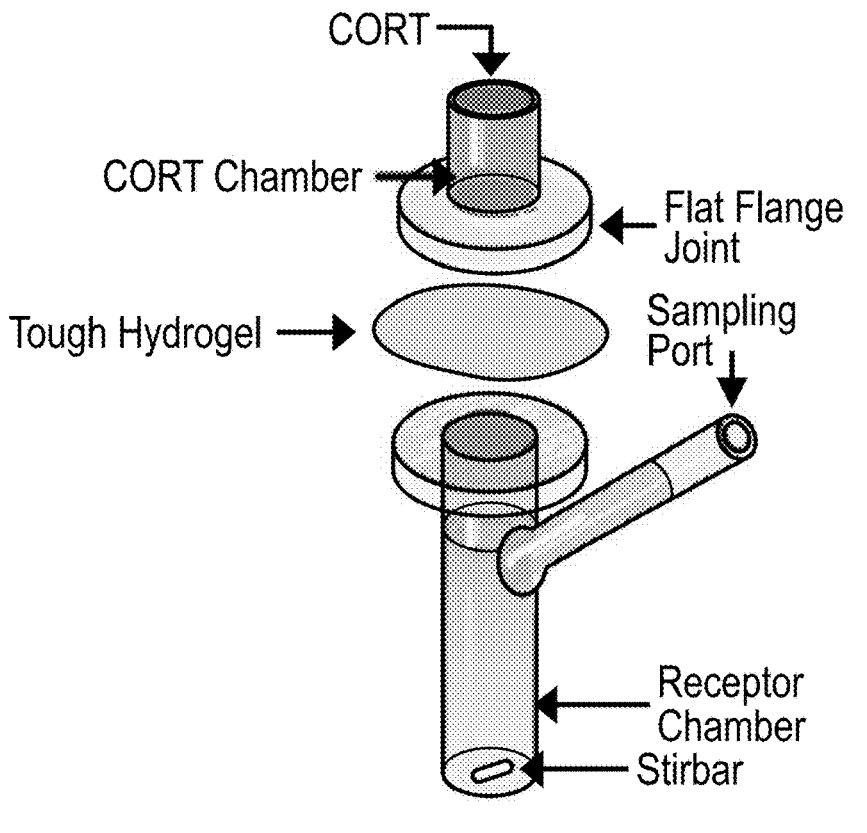

FIG. 22B illustrates the experimental design of studies evaluating the passive diffusion differences of CORT through a polyvinylidene fluoride (PVDF) membrane, a tough gel, and a tough gel adhesive. FIG. 22A is a graph depicting the results of the studies.

Figure 23D:
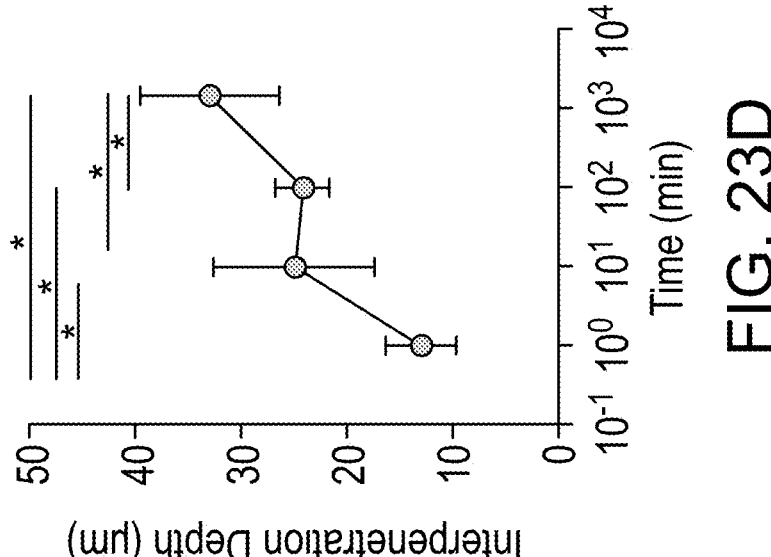

FIGS. 23A-23H depict that the JTA adheres strongly to tendons and supports gliding. FIG. 23A is a schematic depicting that thin tendon planks for adhesion testing were made from bovine tendon samples using a cryotome.

FIG. 23B is a graph depicting that the penetration of the chitosan bridging polymer into tendon in vitro was analyzed via placement of the JTA, using fluorescently labeled chitosan, on tendon plans, and quantifying chitosan depth over time.

Figure 23C:
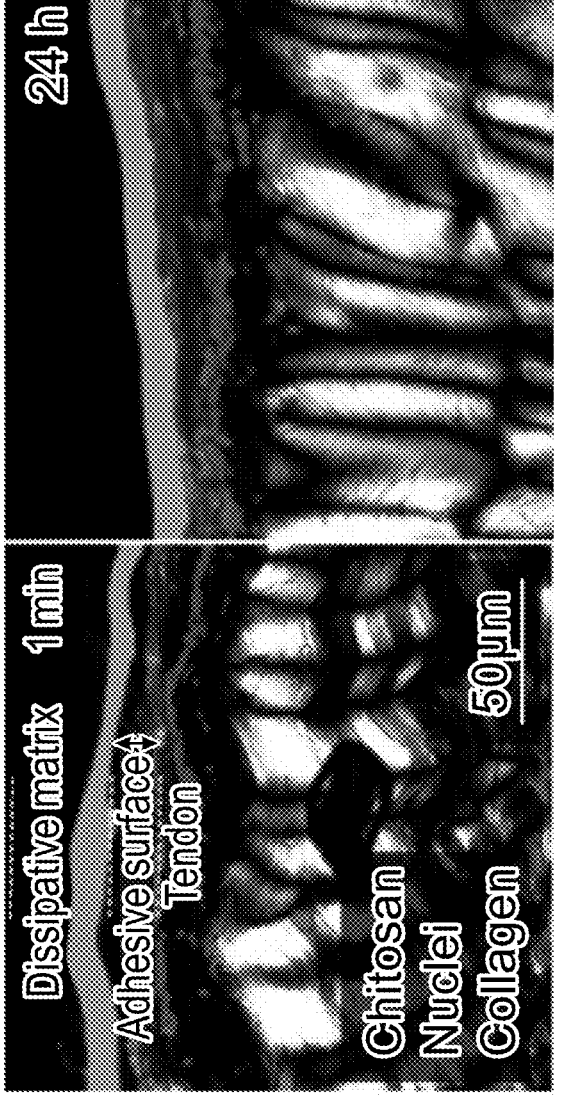

FIGS. 23C and 23D are representative images (FIG. 23C) and quantification of penetration depth of chitosan into tendon over time (FIG. 23D). Mean values are shown and error bars represent ±s.d. (n=3 samples/group). Data were analyzed by a one-way ANOVA with post hoc t-tests with Bonferroni correction (*P<0.008 between time points).

Figures 23E, 23F, 23G, 23H:
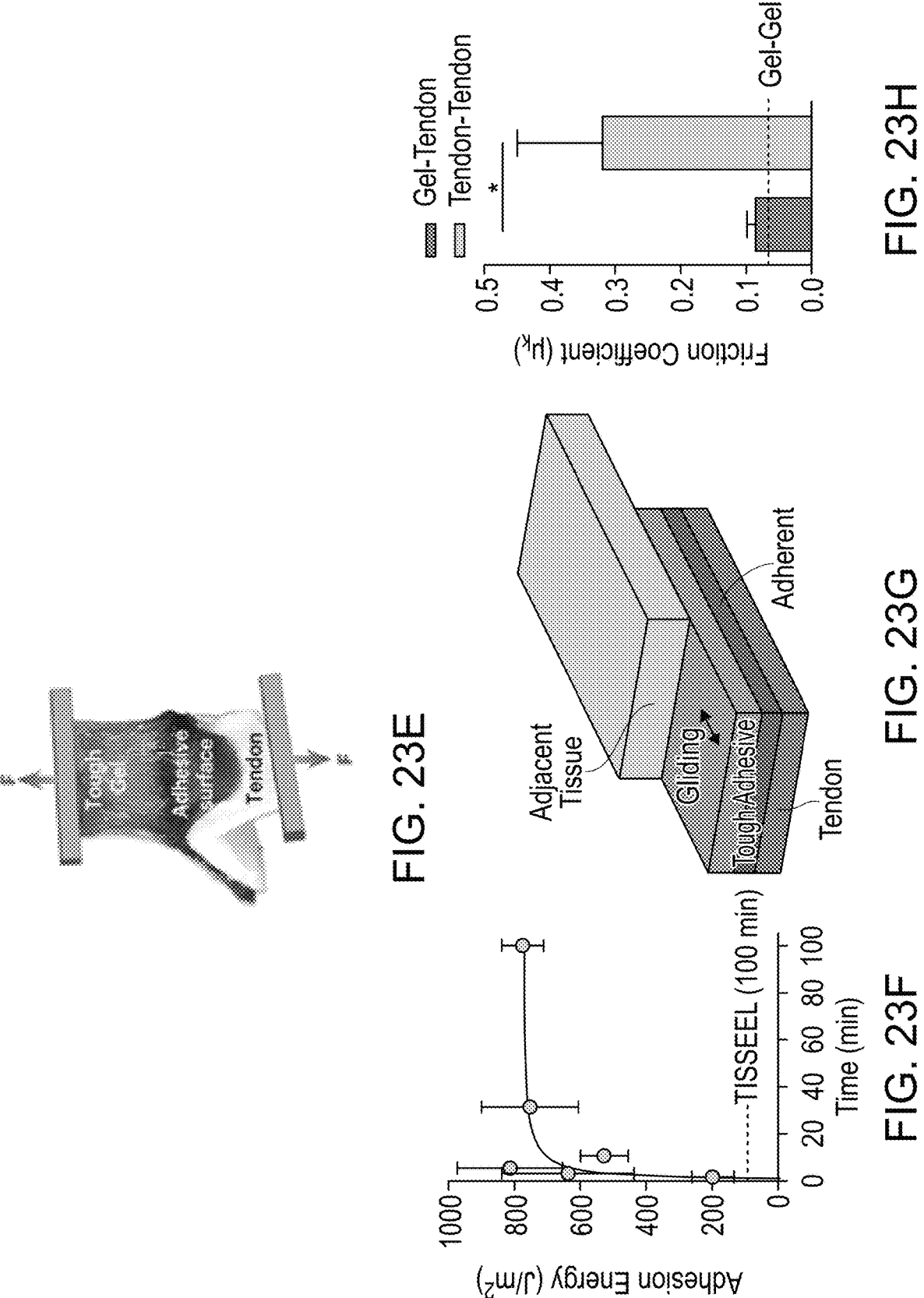

FIG. 23E is a schematic depicting that peel testing was used to evaluate the adhesion energy.

FIG. 23F is a graph depicting quantification of the adhesion energy of JTA to tendon, over time, and comparison to the value achieved with TISSEEL at 100 minutes (dotted line). *P<0.008 between time points. Mean values are shown and error bars represent ±s.d. (n=6-8 samples/group), as analyzed by a one-way ANOVA with post hoc t-tests with Bonferroni correction.

FIG. 23G is a schematic depicting that friction was analyzed between the non-tendon adherent side of the JTA and adjacent (not adherent) tendon.

FIG. 23H is a graph depicting measured coefficient of friction between non-adhered side of the JTA and adjacent tendon tissue (Tendon-Gel), and that for tendon gliding on another tendon (Tendon-Tendon). The coefficient of friction for gliding of one tough adhesive on another tough adhesive (Gel-Gel) is shown as dotted line for comparison. Mean values are shown and error bars represent ±s.d. (n=3 samples/group), as analyzed by a Student's t-test (*P<0.05 between groups).

FIGS. 24A and 24B are images and schematic that depict tendon preparation for adhesion and mechanical testing. As shown in FIG. 24A, bovine tendon samples were cut into thin tendon planks for adhesion energy testing. As shown in FIG. 24B, rat patellar tendons were fine dissected, stamped into a dog bone shape, imaged for their cross sectional area using high frequency ultrasound, and secured in an acrylic pot with liquid metal prior to mechanical testing.

FIGS. 25A-25H depict that the JTA is biocompatible to tendon and supports healing.

Figures 25A, 25B, 25C, 25D, 25E:
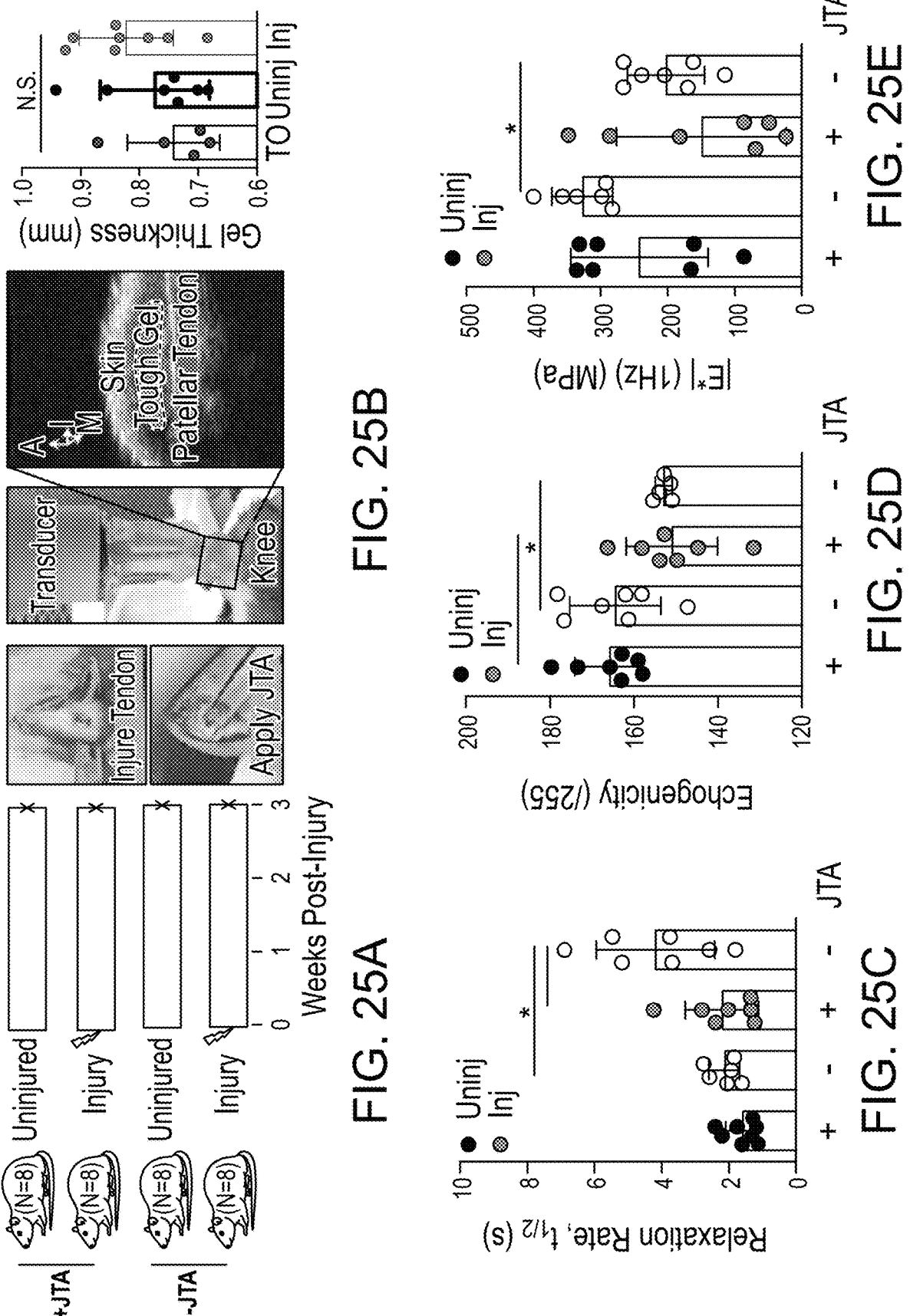

FIG. 25A is a schematic depicting that the effect of patellar tendon injury and JTA implantation on tendon structural and mechanical properties was investigated. Following injury, the JTA was applied on the central midsubstance of the patellar tendon.

FIG. 25B is images and graph depicting that at 3-weeks post implantation, gel thickness was evaluated using high frequency ultrasound. Mean values are shown and error bars are ±s.d. (n=5-8 samples/group), as analyzed by a one-way ANOVA. A—Anterior; I—Inferior; M—Medial.

FIGS. 25C-25E are graphs depicting that the effect of healing and JTA implantation on the relaxation half life and |E*| was evaluated. Mean values are shown and error bars are +s.d. (n=6-8 samples/group), as analyzed by a two-way ANOVA with post hoc t-tests with Bonferroni correction (*P<0.013 is the significant difference between groups).

Figure 25F:
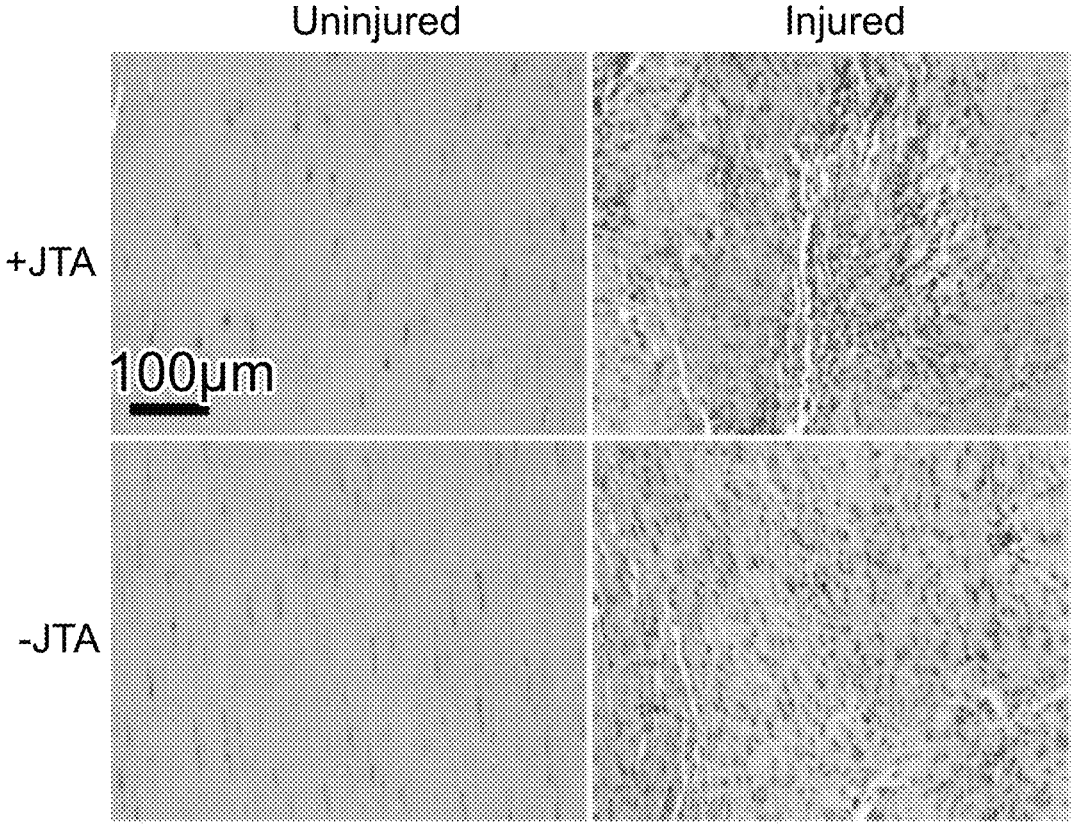

FIG. 25F is immune histology images depicting minimal adjacent tissue inflammation following JTA implantation.

Figure 25H:
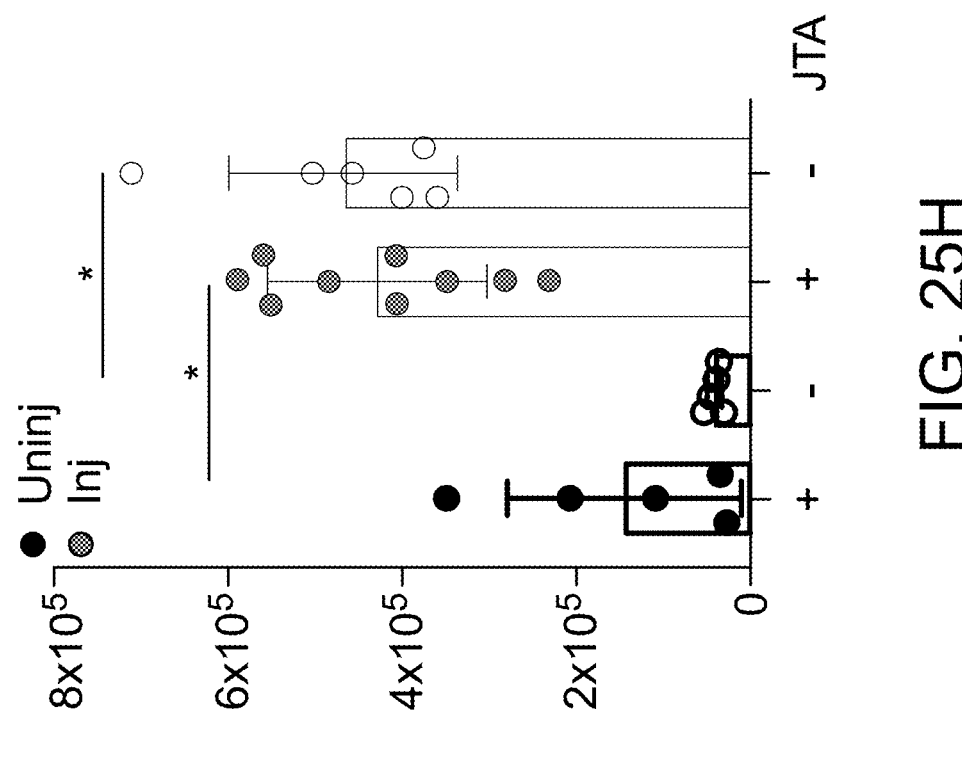
Figure 25G:
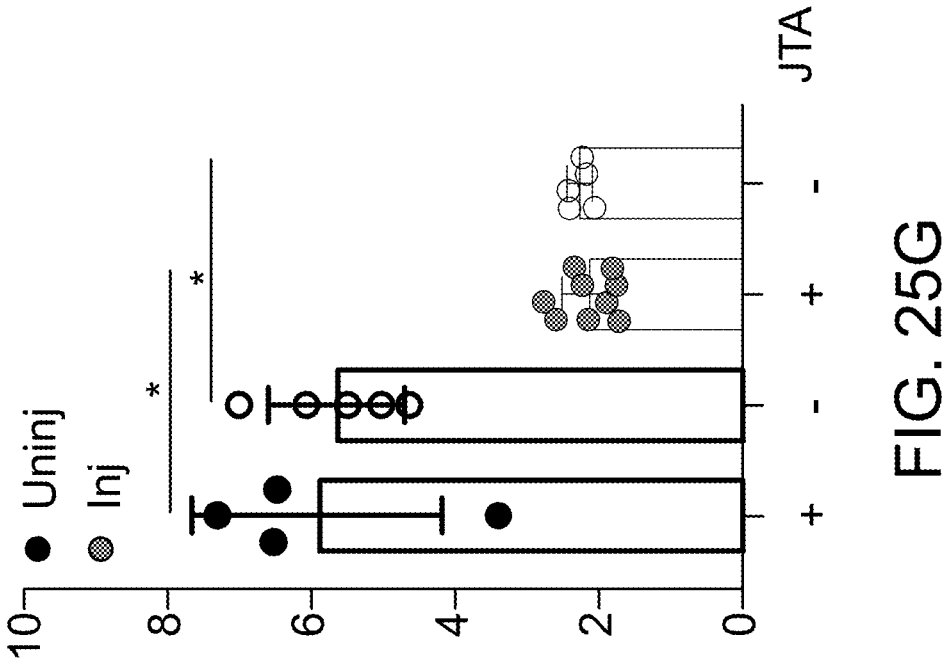

FIGS. 25G and 25H are graphs depicting the effect of healing and JTA implantation on nuclear aspect ratio and cellularity was evaluated. Scale bar=100 μm. Mean values are shown and error bars are ±s.d. (n=4-8 samples/group), as analyzed by a two-way ANOVA with post hoc t-tests with Bonferroni correction (P<0.013 is the significant difference between groups).

Figures 25I, 25J:
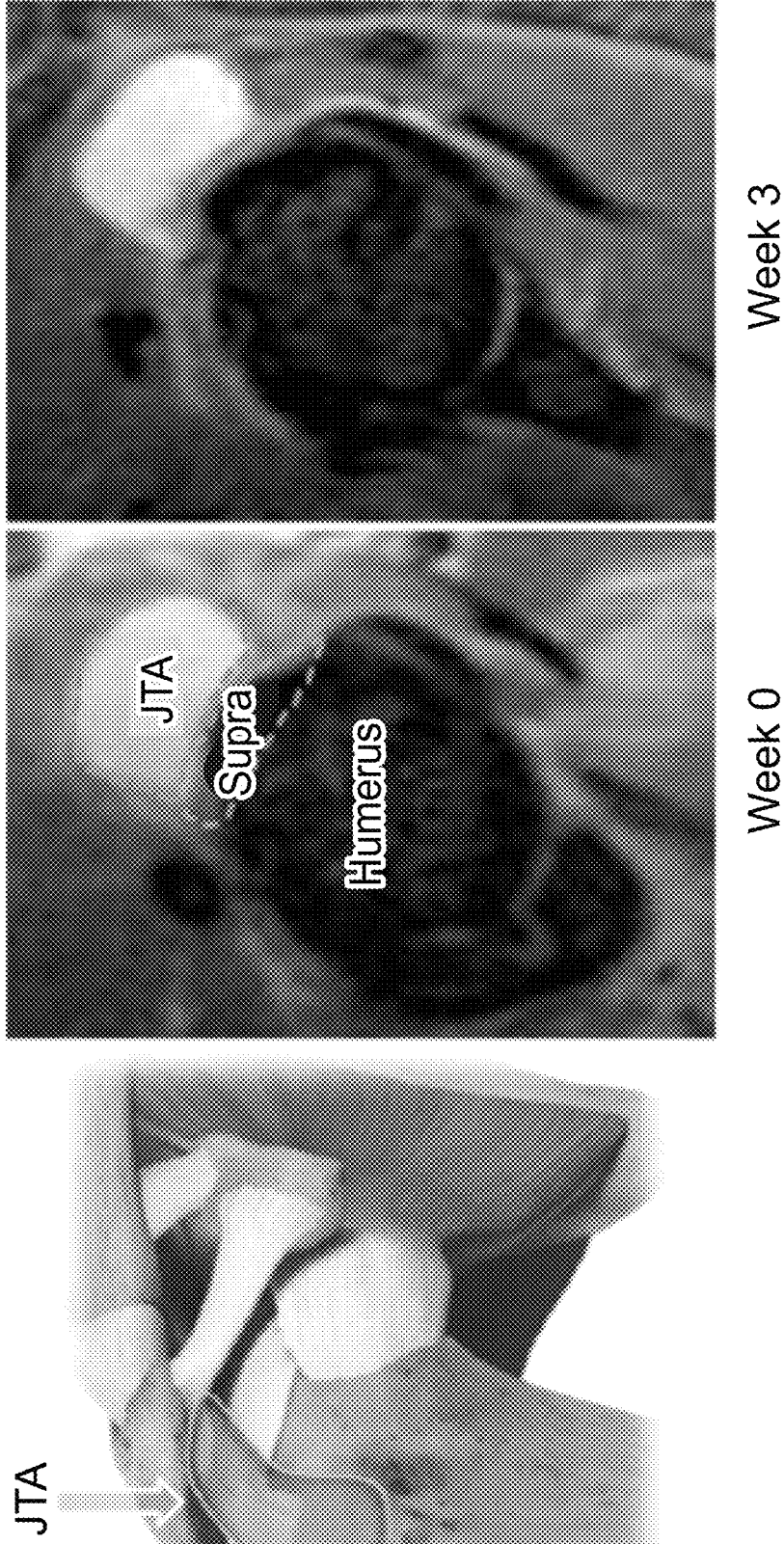

FIGS. 25I and 25J are micrographs showing subacrominal implantation of a tough gel adhesive onto the supraspinatus tendon in rats.

FIGS. 26A-26G are schematic and graphs depicting mechanical testing protocol and effect of healing and JTA implantation on mechanical properties.

Figure 26A:
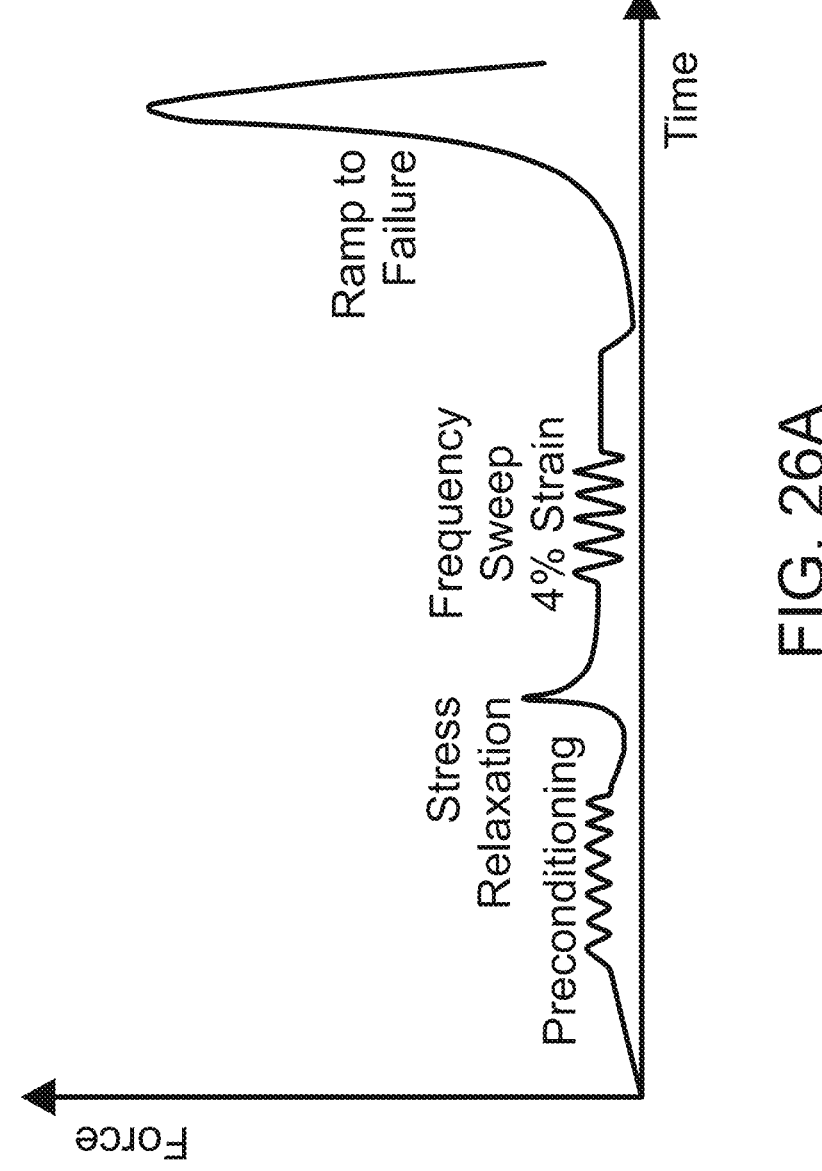

FIG. 26A is a schematic depicting mechanical testing consisted of stress relaxation, dynamic loading, and a ramp to failure.

FIGS. 26B-26G are graphs depicting that the effect of JTA implantation and injury on the toe modulus (FIG. 26B), cross sectional area (FIG. 26C), linear modulus (FIG. 26D), stress relaxation (FIG. 26E), tan δ (FIG. 26F), and cellular grade (FIG. 26G) was evaluated after 3-weeks. Data shown as mean+/−standard deviation. *P<0.013 indicates a significant difference between groups after two-way ANOVAs with post hoc t-tests with Bonferroni corrections. Lines indicate trends as *P<0.025.

FIGS. 27A-27E are schematic, images, and graph depicting that the JTA attaches to the outer periosteal surface of bone and does not cause overt inflammation after implantation in the rat rotator cuff.

Figures 27A, 27B, 27C:
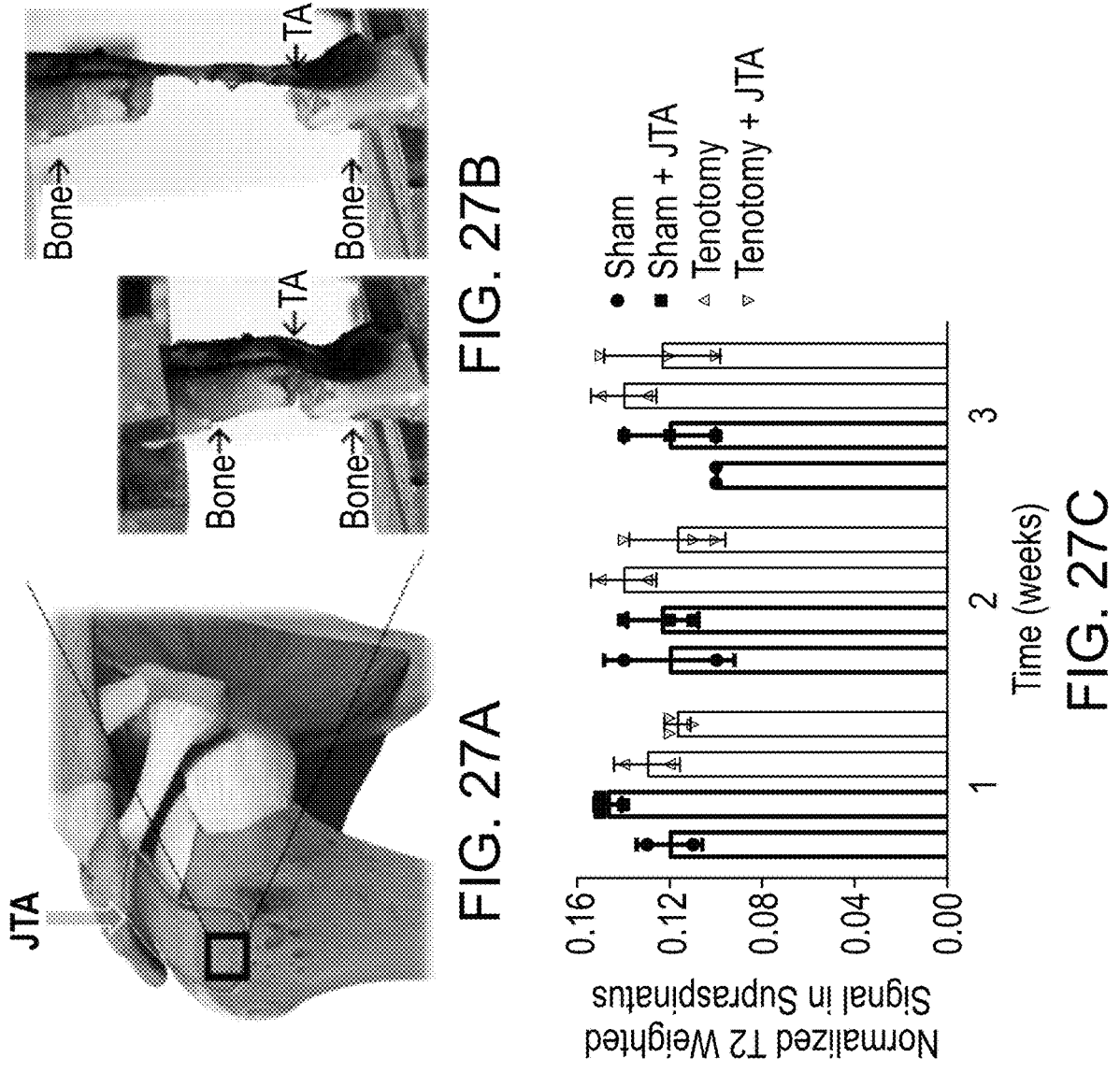

FIG. 27A is a schematic depicting that in the rotator cuff, the JTA was designed to overlap the supraspinatus and enthesis.

FIG. 27B is an image depicting that the JTA attaches to the outer periosteal surface of bone.

FIG. 27C is a graph depicting the effect of healing and JTA implantation on the normalized T2 weighted signal in supraspinatus tendons was evaluated and analyzed by a two-way ANOVA. Data shown as mean+/−standard deviation.

Figure 27D:
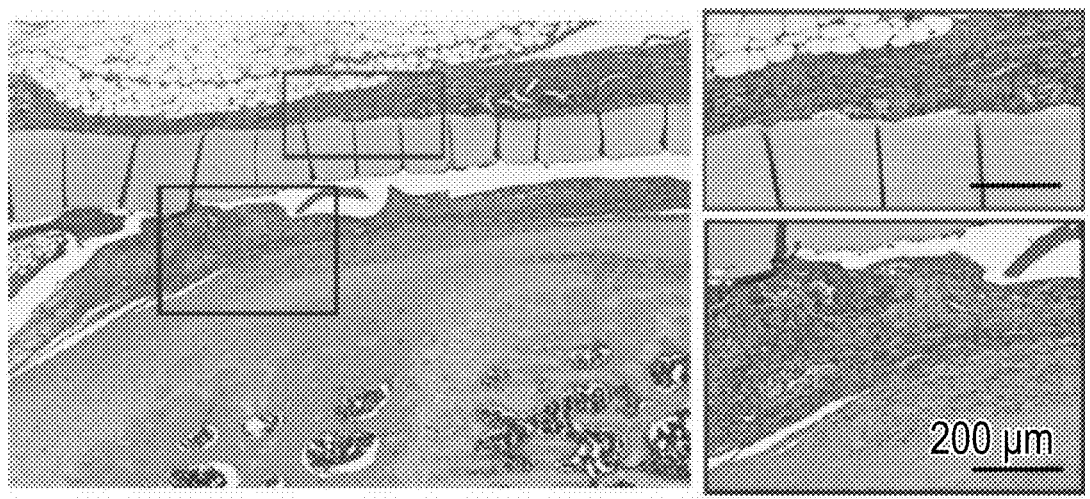

FIG. 27D is immunohistology images depicting JTA biocompatibility 4-weeks post-implantation of JTA to intact rat rotator cuff.

Figure 27E:
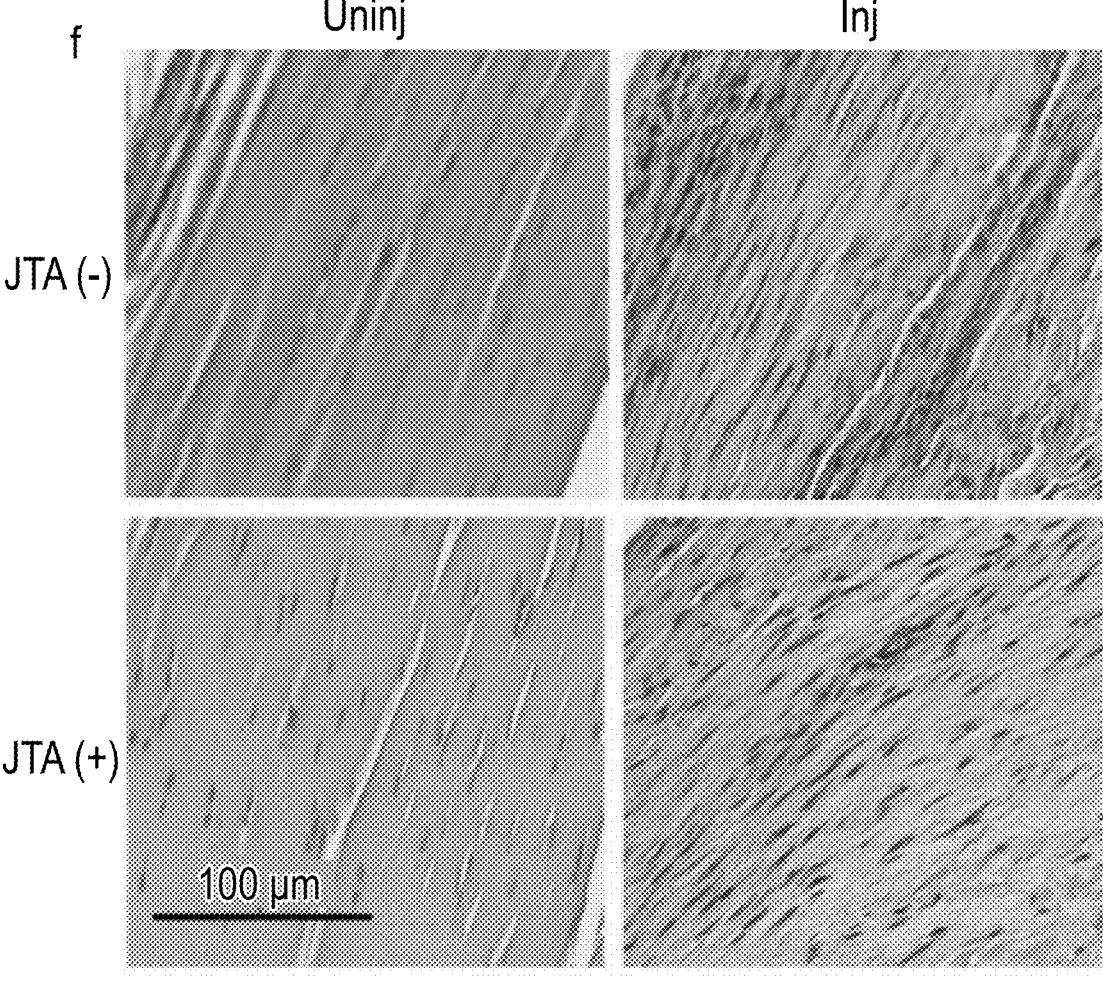

FIG. 27E is immunohistology images depicting supraspinatus tendon 4-weeks post-implantation of JTA to rat rotator cuff.

Figure 28:
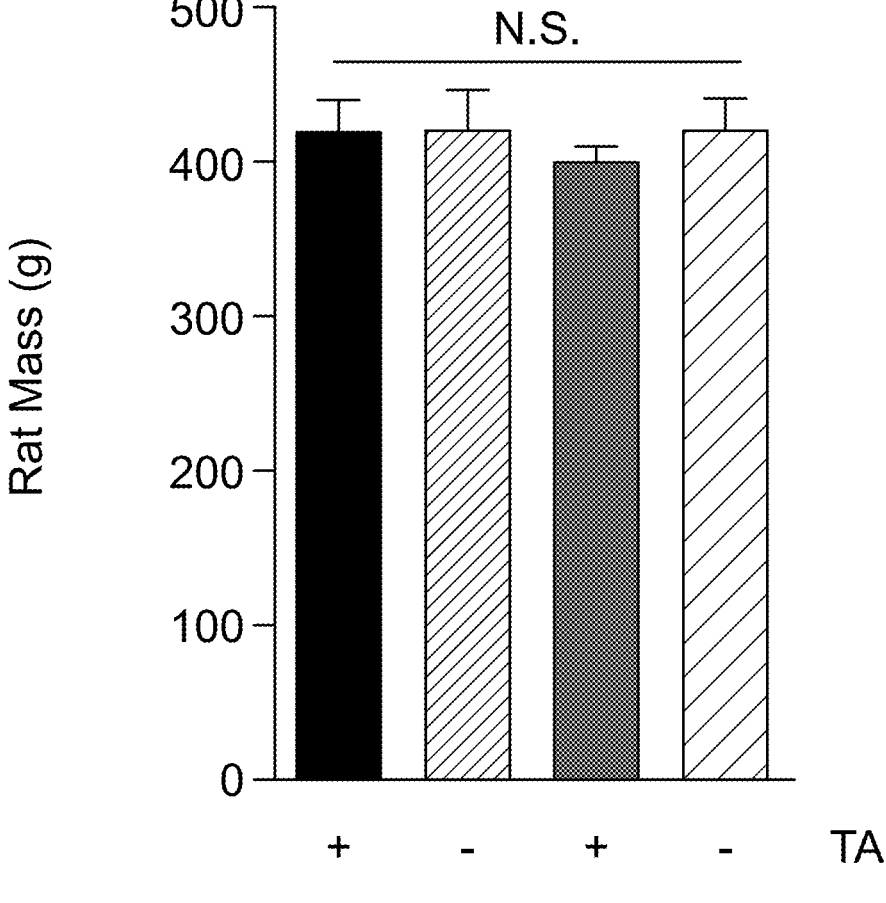

FIG. 28 is a graph depicting effect of JTA and healing on body weight after treatment. Data shown as mean+/−standard deviation.

FIGS. 29A-29I are schematics, graphs, and image depicting that the JTA enables dissolution controlled release at unprecedented drug loadings.

FIG. 29A is a schematic depicting that the effect of the tough hydrogel on CORT diffusion was evaluated using a Franz cell.

FIG. 29B is a graph depicting that computational modeling and experiments evaluated the diffusion constant of the adhesive. Mean values are shown and error bars are ±s.d. (n=4-6 samples/group), as analyzed by a one-way ANOVA with post hoc t-tests with Bonferroni correction (*P<0.017 is the significant difference between groups).

FIG. 29C is a schematic depicting that, in addition to diffusion controlled release, dissolution controlled release was investigated by loading CORT crystals (orange) up 25000× its solubility limit in water within the tough hydrogel.

FIG. 29D is schematic and image depicting CORT aggregation and dissolution within the hydrogel was modeled based on brightfield microscopy images within pre-gel solution.

Figures 29E, 29F:
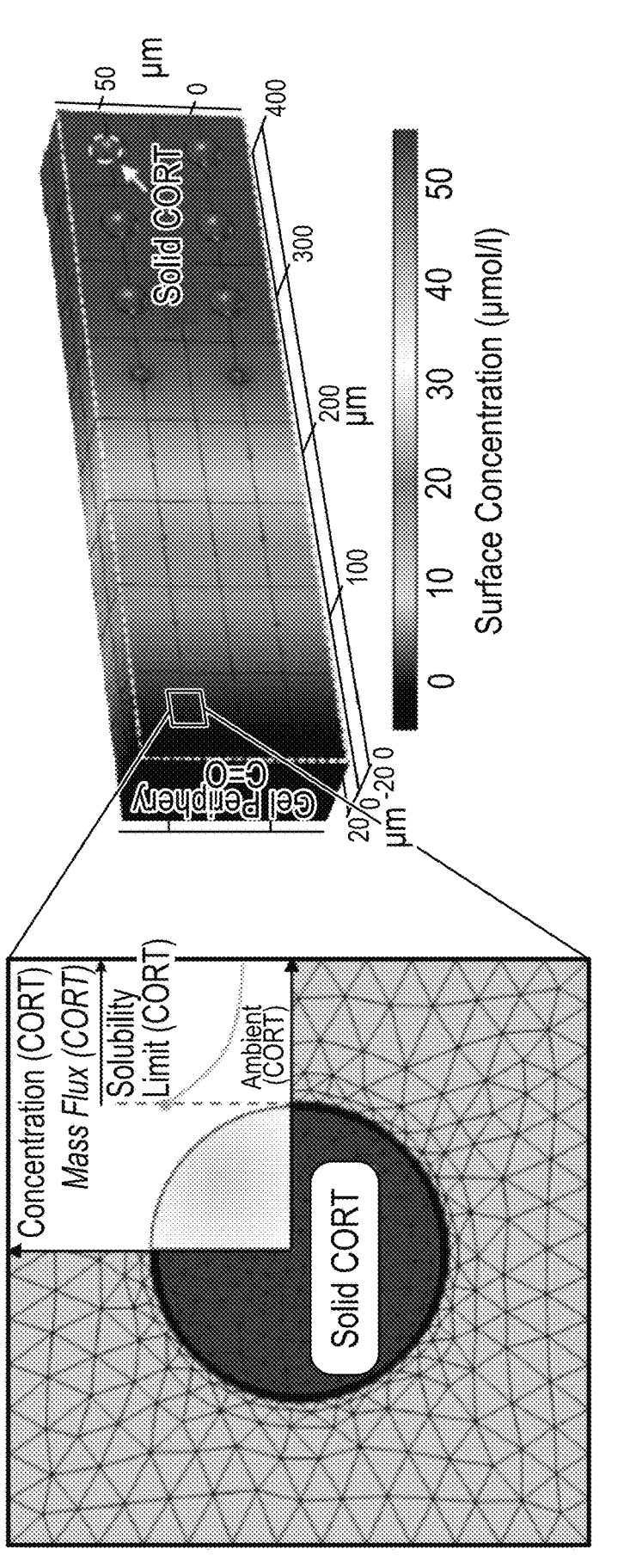

FIGS. 29E and 29F are schematic depicting that dissolution of solid CORT was modeled using FE simulations under well mixed conditions to predict dissolution of particles.

FIG. 29G is a graph depicting dissolution of CORT particles occurred from the outer gel to inner hydrogel.

FIG. 29H is a graph depicting that the effect of CORT loading on drug release was evaluated. Mean values are shown and error bars are ±s.d. (n=3 samples/group), as analyzed by Student's t-tests (*P<0.05 is the significant difference between groups).

FIG. 29I is image depicting that the effect of drug loading on JTA mechanical properties and adhesion were evaluated.

Figure 30:
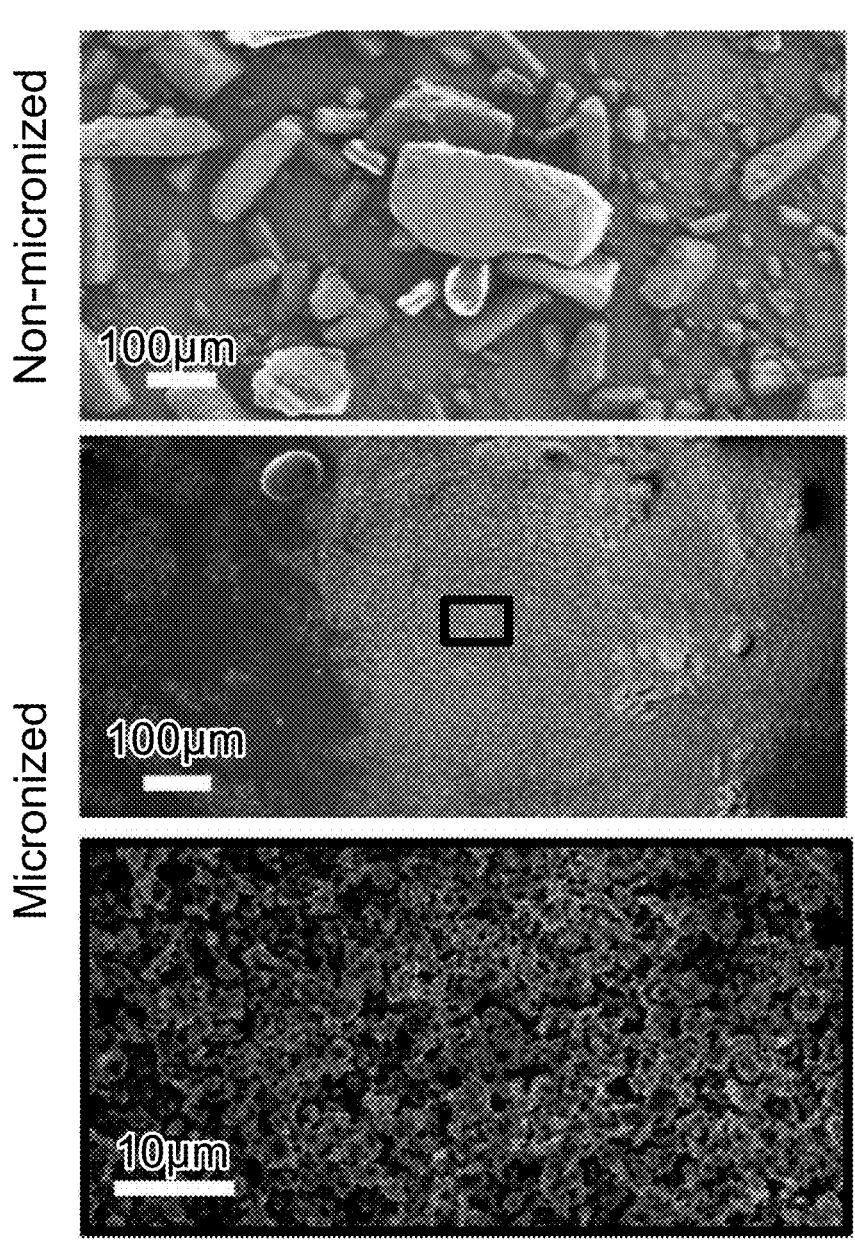

FIG. 30 is mages depicting that micronized CORT particles were used for the incorporation of Triamcinolone acetonide into the JTA.

FIGS. 31A-31E are schematics, images, and graphs depicting that the JTA reduces early inflammation in tendon and promotes improved healing.

Figure 31A:
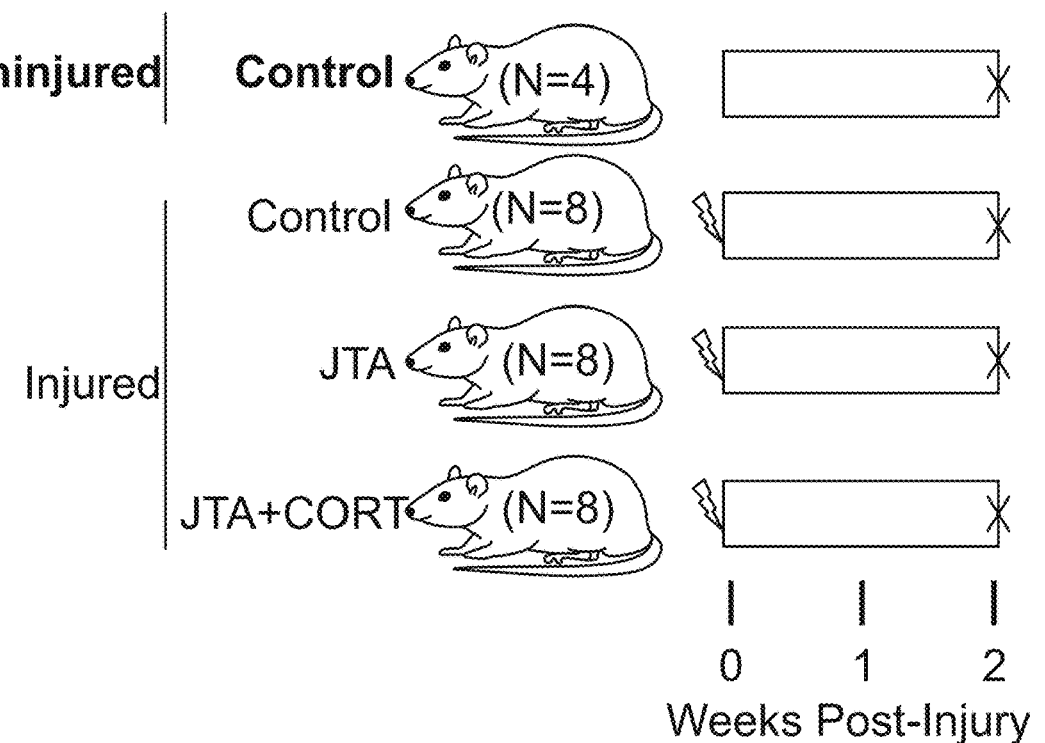

FIG. 31A is a schematic depicting that the effect of the JTA loaded with triamcinolone acetonide (CORT) on patellar tendon vascularity was investigated.

Figure 31B:
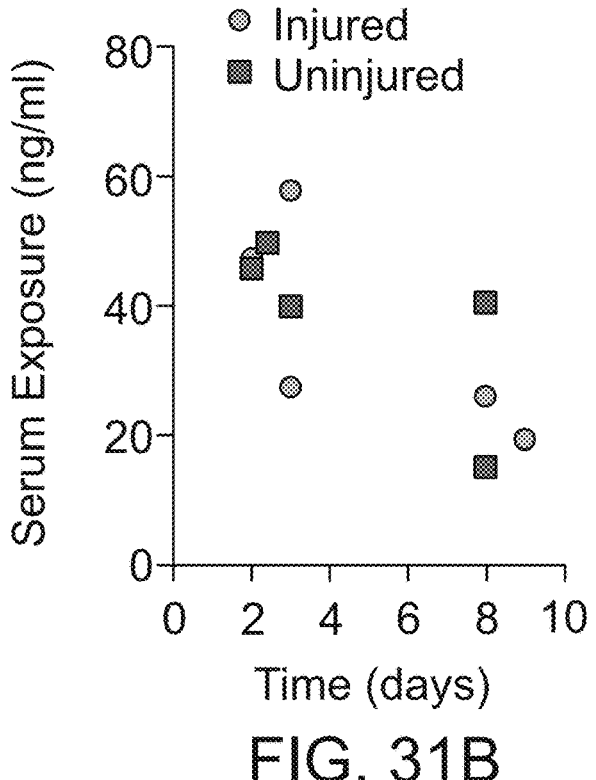

FIG. 31B is a graph depicting that the CORT concentrations in serum were evaluated over time in uninjured and injured groups.

Figure 31C:
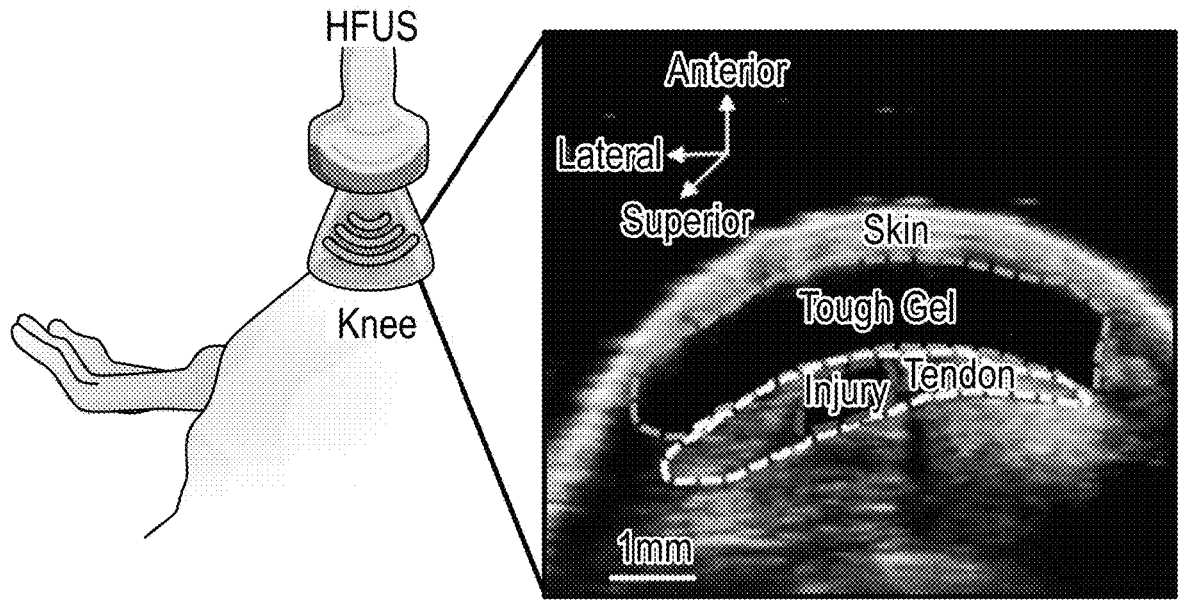
Figure 31D:
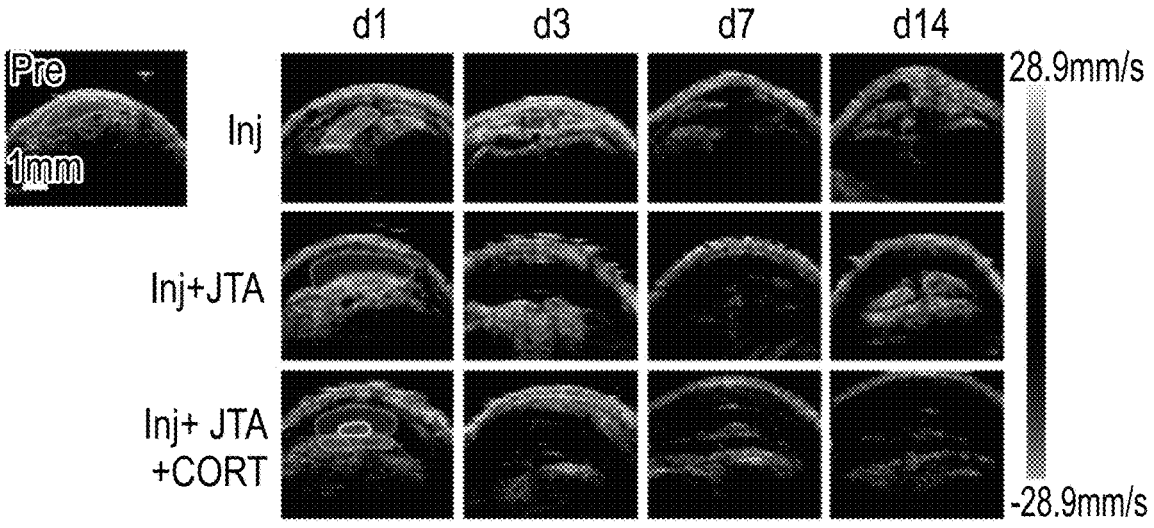

FIGS. 31C and 31D is a schematic and images depicting that HFUS imaging revealed continued adhesion of the JTAs to tendon.

FIGS. 31D and 31E is images and a graph depicting that the effect of treatment and time on total vessel volume after injury was evaluated using HFUS Doppler imaging. Mean values are shown and error bars are ±s.d. (n=4-7 samples/group), as analyzed by a two-way ANOVA with post hoc t-tests with Bonferroni correction (*P<0.017 is the significant difference between groups with lines P<0.034 as trends between groups).

FIGS. 31F-31H are graphs depicting that the effect of treatment on tendon biomechanics after injury was evaluated. Mean values are shown and error bars are ±s.d (n=6-9 samples/group), as analyzed by a one-way ANOVA with post hoc t-tests with Bonferroni correction (*P<0.0083 is the significant difference between groups with lines P<0.017 as trends groups).

FIGS. 32A-32C are an image and graphs depicting the effect of CORT releasing JTAs on animal physiology over time. FIGS. 32A-32C show that dual JTA implantation is well tolerated by rats.

FIG. 32A is an image depicting that The JTA dissolution controlled release system was surrounded by an outer JTA to stabilize it on the rat patellar tendon and also enable a depot-based delivery system.

FIG. 32B is a graph depicting that the rat body weight was examined over time.

FIG. 32C is a graph depicting that the blood glucose levels were evaluated over time.

Figures 33A, 33B:
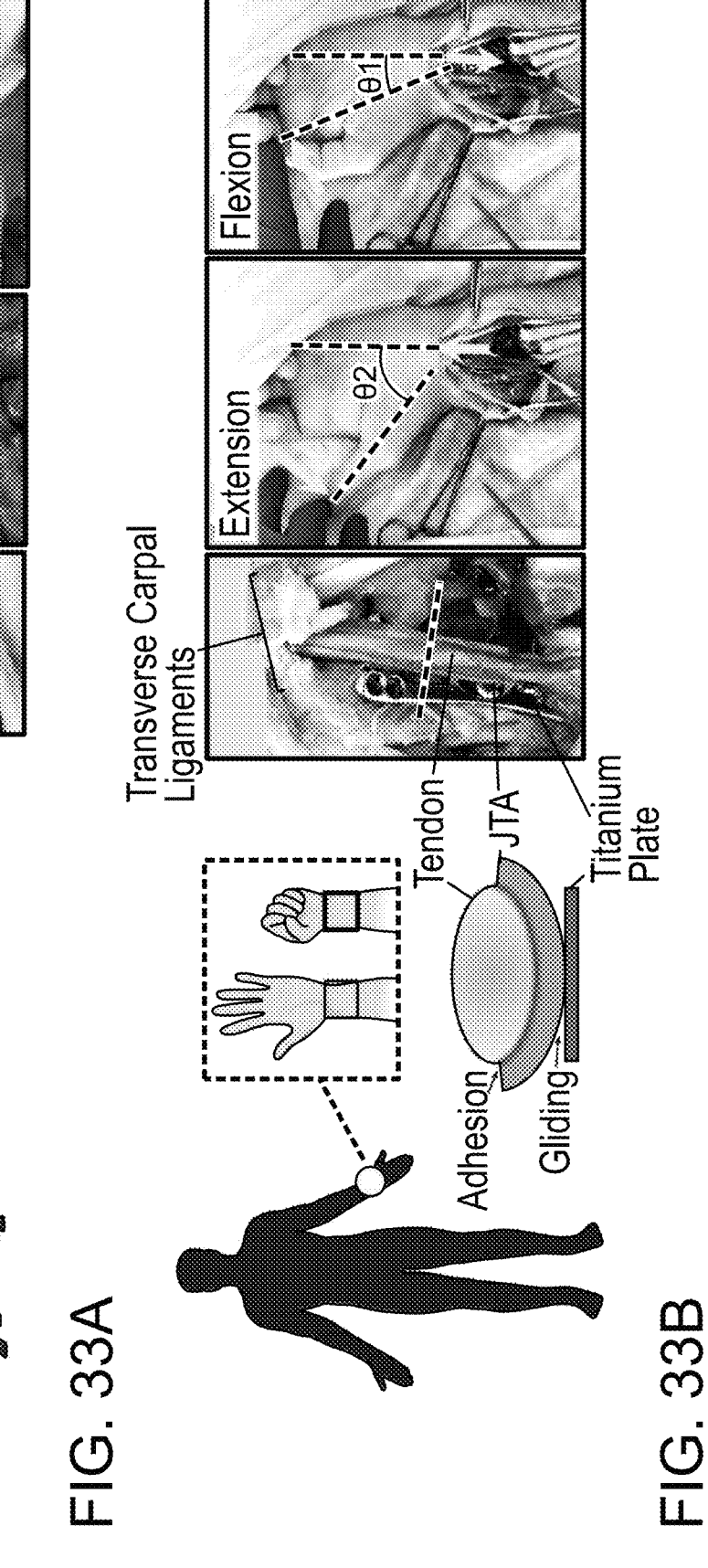

FIGS. 33A and 33B are schematics and images depicting that JTA versatility offers opportunities in large animal and human tendon.

FIG. 33A is a schematic and images depicting that the adhesion of the JTA to wet and bloody porcine patellar, flexor carpi ulnaris, and Achilles tendons was evaluated.

FIG. 33B is a schematic and images depicting that the ability for the JTA to support gliding of the flexor digitorum *profundus* tendon through the transverse carpal ligaments and over volar plates was evaluated in human cadaveric limbs.

Figure 34A:
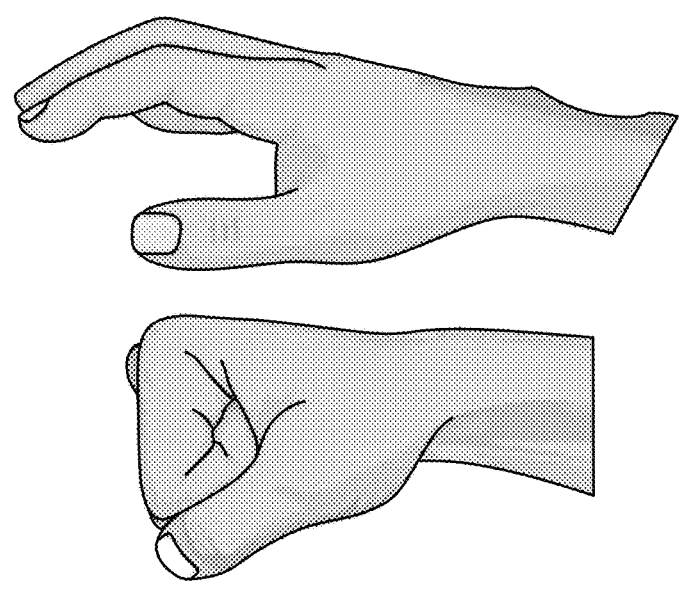
Figure 34B:
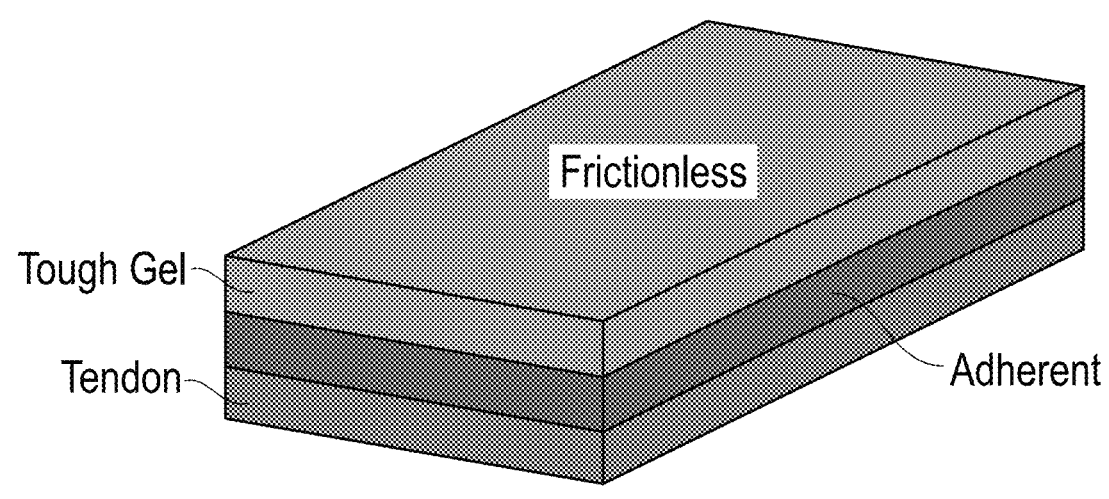

FIGS. 34A and 34B are schematics depicting the effect of JTA implantation on flexor tendon gliding over volar plates in human cadaveric wrists.

FIG. 34A is a schematic depicting that the JTA was investigated to determine if it was compatible with flexor tendon gliding.

FIG. 34B is a schematic depicting that the untreated side of the tough gel exhibits low friction.

DETAILED DESCRIPTION

The present disclosure provides tough gel compositions that are capable of tunable and extended drug delivery, which comprise an interpenetrating networks (IPN) hydrogel, a clay material, and at least one therapeutic agent. It was found that, by incorporating clay into the tough gels, deficiencies associated with drug storage instability of traditional hydrogels and IPN hydrogels can be significantly remedied, therefore enabling the sustained (i.e., extended) and controlled release (i.e., tunable) of the therapeutic agent by the hydrogels.

In a first aspect, the present disclosure is directed to an interpenetrating networks (IPN) hydrogel composition, comprising: a first polymer network and a second polymer network; at least one therapeutic agent; and a clay material. The first polymer network comprises a first polymer that is covalently crosslinked and the second polymer network comprises a second polymer that is ionically crosslinked.

In a second aspect, the present disclosure is directed to an adhesive composition comprising an interpenetrating networks (IPN) hydrogel. The IPN hydrogel comprises: a first polymer network and a second polymer network; at least one therapeutic agent; and a clay material; and an adhesive polymer layer attached to the IPN hydrogel. The first polymer network comprises a first polymer that is covalently crosslinked and the second polymer network comprises a second polymer that is ionically crosslinked.

In some embodiments of the compositions in accordance with first and second aspects as described above, the first polymer network and the second polymer network are covalently coupled.

I. Definition

In order that the present invention may be more readily understood, certain terms are first defined. Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

In addition, it should be noted that whenever a value or range of values of a parameter are recited, it is intended that values and ranges intermediate to the recited values are also part of this invention.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "about" or "approximately" usually means within 5%, or more preferably within 1%, of a given value or range.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof. "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment, symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

Accordingly, as used herein, the term "treatment" or "treating" includes any administration of a composition described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Efficacy of treatment is determined in association with any known method for diagnosing the disorder. Alleviation of one or more symptoms of the disorder indicates that the composition confers a clinical benefit. Any of the therapeutic methods described to above can be applied to any suitable subject including, for example, mammals such as dogs, cats, cows, horses, rabbits, monkeys, and most preferably, humans.

As used herein, the term "subject" includes any subject who may benefit from being administered a hydrogel or an implantable drug delivery device of the invention. The term "subject" includes animals, e.g., vertebrates, amphibians, fish, mammals, non-human animals, including humans and primates, such as chimpanzees, monkeys and the like. In one embodiment of the invention, the subject is a human.

The term "subject" also includes agriculturally productive livestock, for example, cattle, sheep, goats, horses, pigs, donkeys, camels, buffalo, rabbits, chickens, turkeys, ducks, geese and bees; and domestic pets, for example, dogs, cats, caged birds and aquarium fish, and also so-called test animals, for example, hamsters, guinea pigs, rats and mice.

II. Compositions of the Invention

Treatments for tendon injuries remain high unmet medical needs despite many new surgical, rehabilitation, graft, and drug therapies developed. Biomaterial-based therapies may address these unmet needs by providing mechanical support and targeted sustained delivery of drug therapeutics to tendons. However, hydrogels often exhibit poor mechanical toughness and require cell infiltration or suturing to integrate with surrounding tissue, and frequently exhibit burst release of drugs. The present invention provides a novel hydrogel that is mechanical tough, adheres to tissue through an adhesive surface, and releases a therapeutic agent in a sustained manner.

Tough Gel Adhesive or Janus Tough Adhesive

In some embodiment, the present invention provides an adhesive composition comprising an interpenetrating networks (IPN) hydrogel (also termed "tough gel" or "tough hydrogel") as a dissipative matrix and an adhesive composition to solve the aforementioned problem and other problems. The adhesive composition is termed "tough gel adhesive," or "tough hydrogel adhesive." The tough gel adhesive has disparate surface properties and, thus, is also termed janus tough adhesive (JTA), to serve as a high capacity depot for drug delivery to a tissue within a subject, e.g., tendon. It is shown herein that the combination of the dissipative matrix, e.g., tough hydrogel, and an adhesive polymer layer, e.g., chitosan layer, of the JTA promotes unidirectional tissue adhesion with a significant increase (such as about 50%, about 2 fold, about 4 fold, about 8 fold, about 16 fold, about 32 fold, about 50 fold, about 100 fold or more increase) in adhesion energy as compared to currently available commercial adhesive, e.g., fibrin glue (TISSEEL®). Surprisingly and advantageously, the opposite surface of the JTA (the surface of the JTA that is not treated with the adhesive bridging polymer) supports unidirectional gliding of a tissue or a medical device along the opposite surface, such as tendon gliding, as demonstrated in porcine and human tendon preparations in situ. The opposite surface of the JTA has low friction coefficient and, thus, the tissue or medical device gliding does not affect the unidirectional tissue adhesion, or only has minimal effect. Thus, when the JTA adheres to a side of a first tissue, the opposite surface of the JTA that is not treated with the adhesive bridging polymer contacts a second side. The second side can glide along the opposite surface with low friction and the JTA remains adhered to the side of the first tissue. The relative position of the JTA and the side of the first tissue does not change or only change negligibly during the gliding of the second side. The second side may be a side of a second tissue or a medical device. Thus, the JTA can provide protection of a tissue, such as an injured tissue. For example, the surrounding tissue of an injured tendon glide along the surface of the injured tendon during body movement, causing damage, e.g., inflammation, to or delaying recovery of the injured tendon. The injured tendon may be protected by a JTA of the claimed invention by adhering the adhesive polymer layer of the JTA to the injured tendon. The surrounding tissue may glide along the opposite surface of the JTA with low friction, thereby avoiding the gliding along the injured tendon directly and damaging the injured tendon.

The IPN hydrogel or the JTA of the present invention is generally biocompatible. As used herein, the term "biocompatible" is intended to describe any material which upon implantation does not elicit a substantial detrimental response in vivo, e.g., immune response such as inflammation, toxicity, or injury. Biocompatibility of exemplary JTA was confirmed in rat models of patellar tendon and supraspinatus tendon injury models. Longitudinal MRI analysis confirmed sustained anatomical positioning of the exemplary JTA up to 4 weeks post-implantation in the rat rotator cuff and was well tolerated with no signs of overt inflammation. Surprisingly and advantageously, the exemplary JTA allowed for unprecedented drug loading and sustained drug release of the corticosteroid, triamcinolone acetonide in vitro and in vivo. Together, this invention shows utility for JTA to provide mechanical support and to serve as a high capacity depot for drug delivery for the treatment of tissue injury, e.g., tendon injury.

Advantageously, the tough gel or the JTA of the present invention can be loaded with a large amount of undissolved particles and maintain its advantageous properties, such as mechanical, adhesive, and lubricating properties. The weight of the loaded undissolved particles can be up to about 4 times or higher the polymer content of the hydrogel. Accordingly, a large amount of therapeutic agent can be formulated in undissolved aggregates or particles and suspended in the tough gel or JTA.

The tough gel or the JTA can also be used to "package" a therapeutic agent for delivery. For example, a therapeutic agent may be formulated in a "core" formulation and encapsulated within the tough gel or JTA. The core formulation of the therapeutic agent may be in any suitable shape. In certain embodiments, the core formulation is in a cylinder-shape.

Also advantageously, when the JTA serves as a depot for drug delivery, it can be localized at a desirable location in the body of a subject in need thereof. Without wishing to be bound by any theory, the JTA can adhere to a surface inside a body, such as a surface of a tendon. The JTA can remain localized at the desirable location by adhering to the surface of the tissue without the need of suturing because of the high adhesion energy thereof to a surface.

In some embodiments, the present invention provides a drug delivery system comprising the IPN hydrogel composition or the JTA composition of the present invention. The drug delivery system may further comprises an additional drug delivery device. The additional drug delivery device may be any drug delivery device known in the art. Exemplary additional drug delivery devices include, but are not limited to, a scaffold based drug delivery device (e.g., a PLGA scaffold based drug delivery device, a hydrogel based drug delivery device), a liposome, a microsphere, a silica microparticle based drug delivery device, a nanoparticle, a polymer-drug conjugate, a polyplex, or a micelle. In some embodiments, the exemplary drug delivery devices include, but are not limited to, the devices described in U.S. Pat. No. 9,610,328, US Patent Publication US20170119892A1, the contents of each of which are incorporated by reference in its entirety. The additional drug delivery device may be attached to the IPN hydrogel composition or the JTA composition in any suitable manner. For example, the additional drug delivery device may be embedded or encapsulated in the IPN hydrogel composition.

The terms "tough gel composition", "IPN hydrogel composition", "dissipative matrix," and the like are used interchangeably to refer to an interpenetrating networks (IPN) hydrogel composition having a first polymer network that is covalently crosslinked and a second polymer network that is ionically or physically crosslinked. The term "tough gel adhesive," "tough hydrogel adhesive," "Janus tough adhesive (JTA)," and the like are used interchangeably to refer to the IPN hydrogel with an adhesive polymer layer attached to a surface or a side thereof. As used herein, the term "side"

and "surface" are used interchangeably when it refers to a surface of a tissue, a tough gel, a tough gel adhesive, or a medical device.

In certain embodiments, the first polymer in the first polymer network of the composition of the invention is selected from the group consisting of polyacrylamide, poly (hydroxyethylmethacrylate) (PHEMA), poly(vinyl alcohol) (PVA), polyethylene glycol (PEG), polyphosphazene, collagen, gelatin, poly(acrylate), poly(methacrylate), poly (methacrylamide), poly(acrylic acid), poly(N-isopropylacrylamide) (PNIPAM), poly(N,N-dimentylacrylamide), poly(allylamine) and copolymers thereof. In one embodiment, the first polymer is polyacrylamide.

The IPN hydrogel may be biodegradable or non-biodegradable. The covalent crosslinking agent of the first polymer network may be non-biodegradable or biodegradable. In certain embodiments, the first polymer network comprises a first polymer that is covalently crosslinked with a covalent crosslinking agent selected from the group consisting of N,N-methylenebisacrylamide (MBAA), a methacrylate crosslinker, N,N'-dicyclohexylcarbodiimide (DCC), 1-ethyl-3-(3-dimethylaminopropyl)carbodiimide (ECC), N-hydroxysuccinimide, N-hydroxysulfosuccinimide, glutaraldehyde, and a transglutaminase. In one embodiment, the covalent crosslinking agent is N,N-methylenebisacrylamide (MBAA). In other embodiments, the first polymer network comprises a first polymer that is covalently crosslinked with a biodegradable covalent crosslinking agent selected from the group consisting of a poly(ethylene glycol) acrylate, a gelatin acrylate, a hyaluronic acid acrylate, an alginate acrylate, and poloxamer (PEG-PPG-PEG) diacrylate. In one embodiment, the biodegradable covalent crosslinking agent is selected from the group consisting of a poly(ethylene glycol) diacrylate (PEGDA), a gelatin methacrylate (GelMA), a methacrylated alginate (AlgMA), hyaluronic acid methacrylate, and poloxamer (PEG-PPG-PEG) diacrylate. In one embodiment, the biodegradable covalent crosslinking agent is a PEGDA having a molecular weight of about 250 to about 20,000 Da.

In certain embodiments, the first polymer network comprises a first polymer that is covalently crosslinked with a biodegradable covalent crosslinking agent selected from the group consisting of a poly(ethylene glycol) acrylate, a gelatin acrylate, a hyaluronic acid acrylate, an alginate acrylate, and poloxamer. The biodegradable IPN hydrogel has been described in WO 2020/077173, the entire contents of which is incorporated herein by reference.

In some embodiments, the second polymer in the second polymer network of the composition of the invention is selected from the group consisting of alginate, pectate, carboxymethyl cellulose, oxidized carboxymethyl cellulose, hyaluronate, chitosan, carrageenan, ι-carrageenan and λ-carrageenan, wherein the alginate, carboxymethyl cellulose, hyaluronate, chitosan, κ-carrageenan, ι-carrageenan and λ-carrageenan are each optionally oxidized; wherein the alginate, carboxymethyl cellulose, hyaluronate chitosan, κ-carrageenan, ι-carrageenan and λ-carrageenan optionally include one or more groups selected from the group consisting of methacrylate, acrylate, acrylamide, methacrylamide, thiol, hydrazine, tetrazine, norbornene, transcyclooctene and cyclooctyne. In one embodiment, the second polymer is alginate. Modified alginates, such as but not limited to the modified alginates, functionalized alginates, oxidized alginates (including partially oxidized alginates), and oxidized/reduced alginates described in US Publication Nos.

US20170119892A1, US20180326073A1, the disclosures of which are both incorporated herein by reference in their entireties.

In some embodiments, the alginate comprises a mixture of a high molecular weight alginate and a low molecular weight alginate. In one embodiment, the ratio of the high molecular weight alginate to the low molecular weight alginate is about 5:1 to about 1:5, about 4:1 to about 1:4, about 3:1 to about 1:3, about 2:1 to about 1:2, or about 1:1. In a specific embodiment, the ratio of the high molecular weight alginate to the low molecular weight alginate is about 1:1.

In some embodiments, the second polymer network comprises a second polymer that is ionically crosslinked with an ionic crosslinking agent selected from the group consisting of $CaCl_2$, $CaSO_4$, $CaCO_3$, hyaluronic acid, and polylysine. In one embodiment, the ionic crosslinking agent is $CaSO_4$.

As used herein, the term "adhesive," "adhesive polymer layer," and "adhesive surface" are used interchangeably to refer to a layer or a surface that is form by applying an adhesive polymer to a surface of the IPN hydrogel.

In certain embodiments, the adhesive polymer in a composition in accordance with various aspect of the invention and embodiments thereof is a high density primary amine polymer. In one embodiment, the high density primary amine polymer is selected from the group consisting of chitosan, gelatin, collagen, polyallylamine, polylysine, and polyethylenimine. In a specific embodiment, the high density primary amine polymer is chitosan.

In some embodiments, the adhesive polymer layer in a composition in accordance with the various aspects of the invention and embodiments thereof is attached to the IPN via a coupling agent. In some embodiments, the coupling agent comprises a first carboxyl activating agent, such as a carbodiimide. Non-limiting examples of carbodiimide include 1-ethyl-3-(3-dimethylaminopropyl)carbodiimide (EDC, EDAC or EDCI), dicyclohexylcarbodiimide (DCC) and diisopropylcarbodiimide (DIC). In some embodiments, the coupling agent further includes a second carboxyl activating agent. Non-limiting examples of the second carboxyl activating agent is selected from the group consisting of N-hydroxysuccinimide (NHS), N-hydroxysulfosuccinimide (sulfo-NHS), hydroxybenzotriazole (HOBt), dimethylaminopyridine (DMAP), Hydroxy-3,4-dihydro-4-oxo-1,2,3-benzotriazine (HOOBt/HODhbt), 1-Hydroxy-7-aza-1H-benzotriazole (HOAt), Ethyl 2-cyano-2-(hydroximino)acetate, Benzotriazol-1-yloxy-tris(dimethylamino)-phosphonium hexafluorophosphate (BOP), Benzotriazol-1-yloxy-tripyrrolidino-phosphonium hexafluorophosphate, 7-Aza-benzotriazol-1-yloxy-tripyrrolidinophosphonium hexafluorophosphate), Ethyl cyano(hydroxyimino)acetato-02)-tri-(1-pyrrolidinyl)-phosphonium hexafluorophosphate, 3-(Diethoxy-phosphoryloxy)-1,2,3-benzo[d] triazin-4(3H)-one, 2-(1H-Benzotriazol-1-yl)-N,N,N',N'-tetramethylaminium tetrafluoroborate/hexafluorophosphate, 2-(6-Chloro-1H-benzotriazol-1-yl)-N,N,N',N'-tetramethylaminium hexafluorophosphate), N-[(5-Chloro-1H-benzotriazol-1-yl)-dimethylamino-morpholino]-uronium hexafluorophosphate N-oxide, 2-(7-Aza-1H-benzotriazol-1-yl)-N,N,N',N'-tetramethylaminium hexafluorophosphate, 1-[1-(Cyano-2-ethoxy-2-oxoethylideneaminooxy)-dimethylamino-morpholino]-uronium hexafluorophosphate, 2-(1-Oxy-pyridin-2-yl)-1,1,3,3-tetramethylisothiouronium tetrafluoroborate, Tetramethylfluoroformamidinium hexafluorophosphate, N-Ethoxycarbonyl-2-ethoxy-1,2-dihydroquinoline, 2-Propanephosphonic acid anhydride, 4-(4,6-Dimethoxy-1,3,5- triazin-2-yl)-4-methylmorpholinium salts, bis-Trichloromethylcarbonate, and 1,1'-Carbonyldiimidazole.

Further disclosures of IPN hydrogels, including IPN hydrogels with adhesive material, may be found in International Patent Application Publication Nos. WO 2013/103956, WO 2017/165490 and WO 2020/077173 the disclosures of all of which are incorporated herein by reference in their entireties.

The term "composition of the invention" refers to the compositions in accordance with the first and second aspects as described above, and all embodiments thereof as described throughout this disclosure.

Therapeutic Agent

Generally, the tough gel or JTA can serve as a depot for any therapeutic agent. The term "therapeutic agent" as used herein, refers to a substance that is capable of producing a therapeutic effect. In one embodiment, therapeutic agent is selected from the group consisting of a biologic, a small molecule, a metal (e.g., nanoparticles), or a combination thereof.

Non-limiting examples of a biologic (including recombinant biologics) are an antibody, a vaccine, a blood, a blood component, an allergen, a nucleic acid, a protein, a peptide, a cell, a hormone, a growth factor, a cytokine, a chemokine, an immune cell, a lipid, a carbohydrate, a saccharide or a polysaccharide, or a combination thereof.

It has been discovered that, surprisingly and advantageously, the tough gel adhesive of the present invention can be loaded with a large amount of therapeutic agent in an undissolved form and maintain the advantageous properties thereof, such as the mechanical and adhesive properties of the tough gel adhesive. For example, the tough gel or JTA of the present invention may be loaded with a therapeutic agent, e.g., triamcinolone acetonide (CORT), at about 4-times the polymer content (500 mg/ml) and still maintains its other advantageous properties, such as mechanical, adhesive, and/or lubricating property.

Without wishing to be bound by any theory, it was hypothesized that a therapeutic agent may be formulated in an undissolved formulation and suspended in the tough gel or JTA. After the administration of the tough gel or JTA to a subject in need thereof, the therapeutic agent is sequentially dissolved by the body fluid and released from the tough gel or JTA. Because a large amount of therapeutic agent can be loaded in the tough gel or JTA and the therapeutic agent can be sequentially dissolved, a sustained release in a substantially constant rate can be achieved.

The therapeutic agent may be encapsulated within the IPN hydrogel or the adhesive layer or both. The therapeutic agent may also be attached to the surface of the IPN hydrogel or the adhesive layer or both. The encapsulation in and/or the attachment to the IPN hydrogel or the adhesive layer may be via covalent linking or non-covalent interaction.

In some embodiments, a therapeutic agent is released from the tough gel or the JTA in a sustained manner. As used herein, the term "sustained release," "extended release," "release in a sustained manner," "release in an extended manner," and the like, refer to the release of a therapeutic agent from the tough gel or the JTA over a longer period of time as compared a reference release of the therapeutic agent. A "reference release" refers to the release from an otherwise similar or identical formulation of the therapeutic agent but for the association with the tough gel or the JTA from a similar location in the body of a subject. For example, a reference release refers to the release of the therapeutic agent from a bolus administration of the therapeutic agent in a saline buffer to a similar location if the therapeutic agent is dissolved or suspended in the same buffer and is encapsulated in or attached to the tough gel or the JTA. In another example, a reference release refers to the release of the therapeutic agent formulated with a carrier or an excipient if the therapeutic agent is similarly formulated and encapsulated in or attached to the tough gel or JTA.

A sustained release from the tough gel or the JTA may be about 2 times, about 4 times, about 8 times, about 16 times, about 25 times, about 50 times, about 100 times, about 250 times, about 500 times, about 1000 times or more of the time of reference release of the therapeutic agent.

In certain embodiments, the sustained release of a therapeutic agent may be over a period of less than 1 day, longer than about 1 day, about 2 days, about 4 days, about 1 week, about 2 weeks, about 1 month, about 2 months, about 4 months, about 6 months, about 1 years, or longer.

The sustained release of a therapeutic agent may include an initial burst release followed by a slower release over a long period of time. For example, about 80% of the therapeutic agent may be released in a burst release in the first a few days, e.g., two (2) days. The remainder may be released over a longer period of time, e.g., four or more days at a relatively constant rate. In some embodiments, the therapeutic agent may also be released from the time of the administration of the tough gel or JTA in the body of a subject over a long period time that does not include a time period of a "burst" release. For example, as shown in FIG. 29H, the therapeutic agent is released over a period of ten (10) or more days without an apparent "burst."

The sustained release of a therapeutic agent may be achieve through various mechanisms or formulations. In certain embodiments, the therapeutic agent is a compound and may be encapsulated in or attached to the tough gel or the JTA at a concentration (the therapeutic agent/the hydrogel w/v %) that is higher than the solubility limit of the therapeutic agent in water or in a saline buffer, e.g., PBS or HESS. In such a case, the release profile of the therapeutic agent is governed by dissolution and loading. Drug with lower solubility or drug formulated in a slow releasing formulation likely has extended release. The higher loading also can be used to extend release. In some embodiments, the computational modeling as described in Example 1 can be used to model the release of certain therapeutic agents, such as agents with low solubility and to design the drug loading in the tough gel or the JTA for extended release. In some embodiments, the release of a therapeutic agent may be controlled by stimuli responsive release, which can be achieved by altering temperature, applying ultrasound, and changing gel porosity through lyophilization. For lower drug loadings, addition of clay material, such as laponite, can be used to tune release.

The concentration of the therapeutic agent in the tough gel or the JTA may be at least about 50%, about 2 times, about 4 times, about 8 times, about 16 times, about 25 times, about 50 times, about 100 times, about 200 times, about 500 times, about 1000 times, about 2000 times, about 5000 times, about 10000 times, about 20000 times, about 25000 times or more greater than the solubility limit of the therapeutic agent. As used herein, the term "concentration" refers to the ratio of the weight of the therapeutic agent to the volume of the tough gel or the JTA, regardless whether the therapeutic agent is dissolved in the tough gel or the JTA or not.

In some embodiments, the therapeutic agent loaded in an IPN hydrogel or JTA according to the present invention is at least about 10%, about 20%, about 50%, about 1 time, about 2 times, about 4 times, about 8 times, or more polymer content of the IPN hydrogel by weight.

In some embodiments, the therapeutic agent loaded at a concentration much higher than the solubility limit thereof in the tough gel or JTA form undissolved aggregates. The aggregates may have a cross-section area of greater than about 1 $\mu m^2$, about 2 $\mu m^2$, about 4 $\mu m^2$, about 10 $\mu m^2$, about 20 $\mu m^2$, about 50 $\mu m^2$, about 100 $\mu m^2$, about 150 $\mu m^2$, or more. The sequential dissolution of the therapeutic agent from the aggregates leads to sustained release of the therapeutic agent. The aggregate of the therapeutic agent may be formed from crystal form or amorphous structure of a therapeutic agent. For a hydrophobic therapeutic agent, the agent may be suspended in the pre-gel mix prior to cross-linking and form aggregates.

In some embodiments, the sustained release of the therapeutic agent is achieved via formulating the therapeutic agent in a controlled releasing formulation. For example, the therapeutic agent may be formulated in a microsphere, a liposome, a nanoparticle, a micelle, a polymer-drug conjugate, or a polyplex. The therapeutic agent containing formulation, e.g., microsphere or liposome, can be encapsulated in the tough gel or JTA. In certain embodiments, a hydrophilic therapeutic agent is formulated in a controlled releasing formulation and suspended in the IPN hydrogel or JTA and a sustained release of the therapeutic agent can be achieved. The controlled releasing formulations are well known in the art, such as those described Li & Mooney, Designing Hydrogels for Controlled Drug Delivery, Nature Review Materials 1, Article number: 16071 (2016), and Langer & Folkman, supra.

In some embodiments, the sustained release of the therapeutic agent is achieved through stimuli responsive release. Stimuli responsive release was achieved by altering temperature, applying ultrasound, and changing gel porosity through lyophilization. For lower drug loadings, addition of laponite can be used to extend the release.

The therapeutic agent of the invention can be formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN', Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

In certain embodiments, sustained release of the therapeutic agent is achieved via linking the therapeutic agent to the tough gel or JTA with a cleavable covalent bond. The cleavable covalent linking is described in detail in the Patent Application Publication US 2016/0114046, incorporated herein by reference in its entirety.

In some embodiments, sustained release of the therapeutic agent is achieved via attaching the therapeutic agent to a clay as described in detail herein.

In some embodiments, the therapeutic agent is a cell, which produces a second therapeutic agent, e.g., a protein or a small molecule, in situ. The cell may produce the second therapeutic agent over a long period of time and the second therapeutic agent is released in a sustained manner.

In some embodiments, the tough gel is biodegradable and the therapeutic agent may be release in a sustained manner through the degradation of the tough gel.

In certain embodiments, the therapeutic agent comprises an antibody. As used herein, the term "antibody" means an immunoglobulin molecule or a fragment thereof that recognizes and specifically binds to a target, such as a protein, polypeptide, peptide, carbohydrate, polynucleotide, lipid, or combinations of the foregoing through at least one antigen recognition site within the variable region of the immunoglobulin molecule. The term "antibody" encompasses intact polyclonal antibodies, monoclonal antibodies, antibody fragments (e.g., Fab, Fab', F(ab')$_2$, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

In certain embodiments, the therapeutic agent is a small molecule. As used herein, a "small molecule" refers to a compound that has a molecular weight of less than 1000 Da. The small molecule may be an organic compound or an inorganic compound. In certain embodiments, the small molecule is a synthetic organic compound. The small molecule may have a structure that naturally occurs or a structure that is artificially designed.

In some embodiments, the therapeutic agent is a nucleic acid. As used herein, a "nucleic acid" is a biopolymer, including RNA (ribonucleic acid) and DNA (deoxyribonucleic acid) and recombinant nucleic acids, that are composed of single or double strands of nucleotides, which are the monomers of the biopolymer made of three components: a 5-carbon sugar, a phosphate group and a nitrogenous base (e.g., adenine (A), cytosine (C), guanine (G), thymine (T) in DNAs or uracil (U) in RNAs). In some embodiments, the nucleic acid encodes a protein, a peptide or a RNA. In some embodiments, the nucleic acid is a RNA molecule that modulates the expression of a gene, such as an siRNA, an antisense RNA, a ribozyme RNA, an miRNA, an shRNA, and a dicer substrate siRNA (DsiRNA).

In some embodiments, the therapeutic agent is a protein or a peptide. Exemplary proteins include, but are not limited to, an enzyme, a growth factor, a cytokine, or a structural protein.

In some embodiments, the therapeutic agent in the IPN hydrogels of the invention is a substance that treats inflammation. In some embodiments, the therapeutic agent is a substance that treats tissue regeneration. In certain embodiments, the therapeutic agent is a substance that treats tissue regeneration, such as skin tissue, muscle tissue, tendon tissue, ligament tissue, bone tissue, nerve tissue, connective tissue, bursa tissue, adipose tissue, or a combination thereof. In another embodiment, the therapeutic agent is a substance that treats reinnervation. In one embodiment, the therapeutic agent is a substance that relieves or alleviates pain. In some embodiments, the therapeutic agent is any therapeutic agent disclosed in International Patent Application Publication No. WO 2011/109834, the disclosure of which is incorporated herein by reference in its entirety.

In a specific embodiment, the therapeutic agent is selected from the group consisting of hepatocyte growth factor (HGF), basic fibroblast growth factor (bFGF), Insulin-like growth factor-1 (IGF-1), nerve growth factor (NGF), leukemia inhibitory factor (LIF), acid fibroblast growth factor (aFGF), platelet-derived growth factor (PDGF-AA), platelet-derived growth factor (PDGF-BB), epidermal growth factor (EGF), transforming growth factor-α (TGF-α), transforming growth factor-β1 (TGF-β1), vascular endothelial growth factor 121 (VEGF$_{121}$), vascular endothelial growth factor 121b (VEGF$_{121}$b), vascular endothelial growth factor 145 (VEGF$_{145}$), vascular endothelial growth factor 165 (VEGF$_{165}$), vascular endothelial growth factor 165b (VEGF$_{165}$b), vascular endothelial growth factor 189 (VEGF$_{189}$), and vascular endothelial growth factor 206 (VEGF$_{206}$).

In another specific embodiment, the therapeutic agent is a corticosteroid (also called glucocortisteroid or steroid). Non-limiting examples of corticosteroids include betamethasone, prednisone, prednisolone, triamcinolone, methylprednisolone, dexamethasone, or a pharmaceutically acceptable salt thereof. In one embodiment, the corticosteroid is triamcinolone or a pharmaceutically acceptable salt thereof.

In yet another specific embodiment, the therapeutic agent is a nonsteroidal anti-inflammatory drug (NSAID). Non-limiting examples of NSAIDs include aspirin salsalate (Amigesic), diflunisal (Dolobid), ibuprofen (Motrin), ketoprofen (Orudis), nabumetone (Relafen), piroxicam (Feldene), naproxen (Aleve, Naprosyn,) diclofenac (Voltaren), indomethacin (Indocin), sulindac (Clinoril), tolmetin (Tolectin), etodolac (Lodine), ketorolac (Toradol), oxaprozin (Daypro), celecoxib (Celebrex).

In certain embodiments, the amount of the therapeutic agent included in the compositions of the invention range from about 0.1 mg/ml to about 500 mg/ml (i.e., per total volume of the hydrogel or the second polymer network), or about 0.1 mg/ml to about 200 mg/ml, about 0.2 mg to about 150 mg/ml, about 0.2 mg/ml to about 125 mg/ml, about 0.5 mg/ml to about 100 mg/ml, about 1 mg/ml to about 100 mg/ml. In one embodiment, the composition comprises about 1 mg/ml, about 5 mg/ml, about 10 mg/ml, about 20 mg/ml, about 25 mg/ml, about 30 mg/ml, about 40 mg/ml, about 50 mg/ml, about 60 mg/ml, about 70 mg/ml, about 75 mg/ml, about 80 mg/ml, about 90 mg/ml, or about 100 mg/ml of the therapeutic agent. In one embodiment, the composition comprises about 1 mg/ml, about 10 mg/ml, or about 100 mg/ml of the therapeutic agent.

Clay

In some embodiments, in the composition in accordance with the first and second aspects and embodiments thereof as described above, it is hypothesized and verified that the clay material comprises a plurality of clay particles that aggregate in the second polymer network. In one embodiment, the therapeutic agent is encapsulated in the hydrophobic interlayer spaces of the aggregated clay particles. In another embodiment, the therapeutic agent is adsorbed onto the aggregated clay particles. Typically, the interactions between the molecules of a therapeutic agent and the aggregated clay particles are composed of non-covalent interactions, primarily. Types of non-covalent interactions include, for example, electrostatic interactions, van der Waals' interactions, π-effects, hydrophobic interactions, etc. It is further hypothesized that the clay nanoparticles are pH-responsive, where low pH can protonate negative charges on the clay particles, thereby weakening drug-clay interactions and accelerating the drug release. For extended drug release, the mechanism is reversed by applying high pH, which can then deprotonate negative charges on the clay particles, thereby strengthening drug-clay interactions and decelerating the drug release. Furthermore, the tunability of the drug release can be controlled using mechanical agitation (e.g., ultrasonication), heat, and enzymatic reactions. Yet further, there are hydrogen interactions between the hydroxyl and carbonyl groups of the molecules of the therapeutic agent, such as triamcinolone.

Non-limiting examples of suitable clay material is selected from the group consisting of kaolinite, illite, chlorite, vermiculite, smectite, bentonite, sodium smectite, attapulgite, sepiolite, dicite, halloysite, nacrite, and laponite. In one embodiment, the clay material is laponite. In one embodiment, the amount of clay material in a composition of the invention is about 1 mg/ml to about 500 mg/ml of the clay material, or about 1 mg/ml to about 400 mg/ml, about 1 mg/ml to about 300 mg/ml, about 1 mg/ml to about 250 mg/ml, about 2 mg/ml to about 200 mg/ml, about 5 mg/ml to about 200 mg/ml, about 10 mg/ml to about 200 mg/ml, about 10 mg/ml to about 175 mg/ml, or about 10 mg/ml to about 150 mg/ml. In another embodiment, the composition comprises about 1 mg/ml, about 5 mg/ml, about 10 mg/ml, about 20 mg/ml, about 25 mg/ml, about 30 mg/ml, about 40 mg/ml, about 50 mg/ml, about 60 mg/ml, about 70 mg/ml, about 75 mg/ml, about 80 mg/ml, about 90 mg/ml, about 100 mg/ml, about 110 mg/ml, or about 120 mg/ml of the clay material. In another embodiment, the composition comprises about 20 mg/ml, about 40 mg/ml, about 60 mg/ml, about 80 mg/ml, or about 120 mg/ml of the clay material. In yet another embodiment, the composition comprises about 40 mg/ml or about 80 mg/ml of the clay material.

The amounts of the clay material and the therapeutic agent in the compositions of the invention may also expressed in terms of weight ratios of the clay material to the therapeutic agent. In general, a higher ratio of the clay material to the therapeutic agent is shown to lead to improved colloidal stability. In one embodiment, the weight ratio of the clay material to the therapeutic agent is from about 100:1 to about 2:5, such as about 100:1, 95:1, 90:1, 80:1, 75:1, 70:1, 60:1, 50:1, 40:1, 30:1, 25:1, 20:1, 15:1, 10:1, 8:1, 7:1, 6:1, 5:1, 4:1, 3:1, 2:1, 1:1, 1:2, 1:3, 1:4, 1:5, 2:3, 2:5. In one embodiment, the weight ratio of the clay material to the therapeutic is from about 50:1 to about 2:5.

Lubricant

A surprising and advantageous property of the JTA is that the non-adhesive surface of the JTA demonstrated very low coefficients of friction of JTA on adjacent surface, such as a surface of a tissue or a medical device. Accordingly, the JTA can be used as a protective barrier for a tissue, such as injured tendon, in that the JTA allows gliding of other tissue or medical device on the tissue to be protected. Without wishing to be bound by any theory, it is hypothesized that an adjacent tissue or a medical device to a tissue to be protected can glide over the non-adhesive side of the JTA at low friction, thereby protecting the tissue from damaging.

To further reduce the friction between the non-adhesive surface of the JTA and the adjacent surface of a tissue or a medical device, the JTA of the present invention may further comprise a lubricant. Any lubricant that is suitable for in vivo purpose can be used in the present invention. Lubricants for in vivo use are well known in the art, such as those described in Zhao et al., Effects of Lubricant and Autologous Bone Marrow Stromal Cell Augmentation on Immobilized Flexor Tendon Repairs, J. Orthop. Res., 34(1): 154-160 (2016); Sun et al., The Effect of Hyaluronidase, Phospholipase, Lipid Solvent and Trypsin on the Lubrication of Canine Flexor Digitorum Profundus Tendon, J. Orthop. Res., 26(9): 1225-1229 (2008); and Sun et al., Boundary Mode Lubrication of Articular Cartilage with a Biomimetic Diblock Copolymer, Proc. Natl. Acad. Sci., 116(25) 12437-12441 (2019). Exemplary lubricants for in vivo use include, but are not limited to, surface-active phospholipid, lubricin, hyaluronic acid (HA), collagen, proteoglycan, or carboxymethyl cellulose (CMC) fluids.

Pharmaceutical Composition

The present disclosure further contemplates the inclusion of one or more pharmaceutically acceptable excipients in the compositions of the invention. Accordingly, in some embodiments, the IPN hydrogel further comprises a pharmaceutically acceptable excipient.

For administration to a subject, the IPN hydrogels, JTAs, and therapeutic agents described herein can be provided as pharmaceutically acceptable (e.g., sterile) compositions. Accordingly, in one aspect, the invention provides a pharmaceutical composition comprising an IPN hydrogel or JTA. In another aspect, the invention provides a pharmaceutical composition comprising an IPN hydrogel or JTA that a therapeutic agent.

These pharmaceutically acceptable compositions, such as the composition comprising IPN hydrogel, JTA, or therapeutic agent, can be formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) parenteral administration, for example, by subcutaneous, intramuscular, intravenous (e.g., bolus or infusion) or epidural injection as, for example, a sterile solution or suspension, or sustained-release formulation; (2) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., *Ann. Rev. Pharmacol. Toxicol.* 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

III. Methods of the Invention

Furthermore, methods of using the compositions of the invention are also contemplated. In some embodiments, the present invention relates to a method of reducing friction between a first side of a first tissue and a second side. Without wishing to be bound by any theory, it was hypothesized that a JTA of the present invention can be applied to a first side of a first tissue, wherein the adhesive composition comprising an interpenetrating networks (IPN) hydrogel, comprising a first polymer network and a second polymer network; and an adhesive polymer layer attached to a first surface of the IPN hydrogel; wherein the IPN hydrogel has a second surface that is different to the first surface; wherein the first polymer network comprises a first polymer that is covalently crosslinked and the second polymer network comprises a second polymer that is ionically crosslinked; wherein the adhesive polymer layer contacts the first side and a second surface of the IPN hydrogel that is different to the first surface contacts the second surface; thereby reducing the friction between the first side and the second side. The second side is a side of a second tissue or a medical device.

The present invention also relates to a method of protecting a first side of a first tissue or promoting the recovery of the first tissue. Without wishing to be bound by any theory, it was hypothesized that the JTA of the present invention can be applied to the first side of the first tissue to reduce the friction between the first side and a second side, thereby protecting the first side of the first tissue or promoting the recovery of the first tissue.

In some embodiments, the IPN hydrogel or the JTA comprises a lubricant to further reduces the friction between the first side of the first tissue and the second side.

In certain embodiments, the present disclosure relates to a method of treating a disease, a disorder, or a condition in a subject, comprising administering a tough gel composition described herein to the subject. Many disease, disorder or condition can be treated using the IPN hydrogel or JTA loaded with therapeutic agents of the present invention. The present invention relates to a method to treat diseases including, but not limited to, cancer, infectious disease, cardiovascular disease, digestive system disease, hematological disease, reproductive system disease, respiratory system disease, urinary system disease, endocrine system disease, skeletal muscle disease, or lymphatic and immune system disease. Without wishing to be bound by any theory, it was hypothesized that the IPN hydrogel or the JTA can be administered at or close to a tissue and release a suitable therapeutic agent, thereby treating the disease.

In some embodiments, the method of treating a disease comprises administering a JTA loading with one or more therapeutic agents at or close to a tissue. Advantageously, the JTA can be localized in a desired location and maintain at the location. For example, the JTA loaded with an anti-inflammatory agent can be attached to an inflammatory tendon and maintain attached to release the anti-inflammatory agent to treat the inflammation of the tendon.

Non-limiting examples of a treatable disease, a disorder, or a condition include inflammation, muscle or tendon degeneration, or an autoimmune disease. Non-limiting examples of an autoimmune disease include gout, systemic lupus erythematosus, rheumatoid arthritis, and psoriasis.

In some embodiments, the present disclosure relates to a method of treating tissue in a subject, comprising administering a tough gel composition described herein to the subject. In a certain embodiments, the present disclosure relates to a method of treating tissue inflammation in a subject, comprising administering a tough composition described herein to the subject. In some embodiments, the present disclosure relates to a method of treating tissue degeneration in a subject, comprising administering a tough gel composition described herein to the subject. Examples of treatable tissue include skin tissue, muscle tissue, tendon tissue, ligament tissue, bone tissue, nerve tissue, connective tissue, bursa tissue, adipose tissue, or a combination thereof.

In some embodiments, the present disclosure relates to a method of promoting tissue regeneration in a subject, comprising administering a tough gel composition described herein to the subject. Examples of treatable tissue include skin tissue, muscle tissue, tendon tissue, ligament tissue, bone tissue, nerve tissue, connective tissue, bursa tissue, adipose tissue, or a combination thereof. In an eighth aspect, the present disclosure relates to a method of promoting reinnervation in a subject, comprising administering a tough gel composition described herein to the subject. In certain embodiments, the present disclosure relates to a method of inducing immunosuppression in a subject, comprising administering a tough gel composition described herein to the subject.

A composition of the invention may be administered systemically, intravenously, intraperitoneally, intramuscularly, subcutaneously, transcutaneously, percutaneously, transdermally, intraarterially, subdermally, transmucosally, parentally, or topically. In one embodiment, a composition of the invention is administered subcutaneously. In one embodiment, a composition of the invention is administered directly at a treatment site in the body of the subject.

The present disclosure further contemplates tunable or on-demand release of the therapeutic agent from the compositions of the invention. Tunable release can be achieved by any known means in the art including as described in US 2016/0114046, incorporated herein in its entirety, which discloses use of click chemistry based hydrogels that release drugs upon ultrasound stimulation or using temperature sensitive polymer compositions as disclosed in U.S. Pat. No. 6,645,517 or by photothermal energy. In this disclosure, the on-demand release of therapeutic agent is triggered by modifying temperature that can affect drug dissolution. This may be achieved by placing an icepack or heat source adjacent to the scaffold. Release may also be accelerated through, for example, ultrasound stimulation (e.g., using an ultrasound transducer. For example, the ultrasound system may be positioned adjacent to the scaffold. On-demand release may also be achieved by incorporating biodegradable crosslinking agents (i.e., GelMA) into the first polymer network of the hydrogel system. Furthermore, an enzymatic approach (e.g., proteases) and photo-activation that compromise the integrity of the hydrogel, thereby triggering drug release, are also envisioned. Accordingly, in some embodiments, the method in accordance with the third, fourth, fifth, sixth, seventh, eighth, and ninth aspects as described above further comprises subjecting the composition to ultrasound agitation, thermal treatment, enzyme treatment, radiation treatment, or a combination thereof, in order to trigger an on-demand release of the therapeutic agent.

EXEMPLIFICATIONS

Example 1. Materials and Methods

Synthesis of tough gel adhesives: The tough gels were synthesized as previously described in Sun et al. (*Nature*, 2012, 489(7414):133-136), specifically by combining a solution of 2% sodium alginate and 12% acrylamide in Hank's balanced salt solution (HBSS) with N,N'-methylenebis (acrylamide), TEMED, ammonium persulfate, and calcium sulfate dihydrate. Chitosan (2%) and coupling reagents (1-ethyl-3-(3-dimethylaminopropyl) carbodiimide and sulfated N-hydroxy-succinimide) (12 mg/ml) were used to covalently bind the dissipative matrix and tendon.

To prepare tough gel adhesives incorporating corticosteroid and laponite, two types of crosslinked polymer (ionically crosslinked alginate and covalently crosslinked polyacrylamide) were mixed with laponite and corticosteroid particles.

Adhesion Energy Application and Measurement: Thin tendon planks ($15\times1\times40$ mm$^3$) were prepared from bovine flexor tendons using a freezing stage microtome (CM1950, Leica, Wetzlar, Germany). Tough hydrogel strips were synthesized and thin 0.003 mil PET backing layers were placed adjacent to the strips and attached with superglue (Loctite 454). The end of the tough hydrogel-PET composite was secured with thin acrylic pieces ($2\times1$ cm$^2$) and superglue. The tough hydrogel was then adhered to tendon planks as described above while sandwiched under strain control between glass slides (Li, J. et al. Tough adhesives for diverse wet surfaces. Science 357, 378-381, doi:10.1126/science.aah6362 (2017)). Adhesion energy was measured with 180° peeling tests (Instron 3342, Norwood, MA) under uniaxial tension (100 mm/min). Using captured force and displacement data, the adhesion energy was quantified by multiplying the steady state force by two and dividing by the sample width. Commercially available fibrin sealant (TISSEEL, Baxter) was tested in a similar manner as a control.

Interpenetration of Bridging Polymer: Interpenetration of the bridging polymer into the tissue was assessed using FITC-labeled chitosan (Qaqish, R. B. & Amiji, M. M. Synthesis of a fluorescent chitosan derivative and its application for the study of chitosan-mucin interactions. *Carbohydrate Polymers* 38, 8 (1999)) and confocal microscopy (LSM710, Zeiss, Oberkochen, Germany). Thin tendon samples were created using a cryotome and biopsy punched into discs (diameter 8 mm, thickness 1 mm). Tough gel discs (diameter 8 mm, thickness 1 mm) were synthesized. Using a similar application process, the JTA was applied to tendon surfaces with the FITC-labeled chitosan and evaluated for interpenetration into tendon tissue after 1, 10, and 100 minutes. At these timepoints, the tendon-JTA composite was snap frozen in liquid nitrogen, bisected, and cryosectioned (section thickness=40 μm). Sections were then stained with DAPI and mounted (Prolong™ Gold Antifade Mountant with DAPI, ThermoFisher). Samples were imaged using a confocal microscope for cell nuclei (DAPI, excitation laser 405 nm), chitosan (FITC, excitation laser 488 nm), and collagen (polarized light). The interpenetration depth was defined as the distance by which the FITC channel overlapped the collagen channel.

Friction Assessment: Flat tendon samples and tough gels were mounted on a glass slide ($15\times40\times1.5$ mm$^3$). Smaller samples ($10\times10\times1$ mm$^3$) of tendon and tough gel were mounted on a sled containing a 50 g mass. Tendon-tendon, tendon-janus tough gel, and janus tough gel-janus tough gel friction were tested by pulling combinations of samples (n=3/group) horizontally (0.25 mm/min) with a load cell mounted to compute the kinetic friction coefficient ($\mu_k$). The coefficient of kinetic friction was calculated by dividing the steady state force by the normal force.

Patellar Tendon Defect Model: The effect of JTA implantation on uninjured and injured tendons was evaluated in F344XBN rats (age: 8 months; body weight: 400-500 g; National Institute on Aging) (N=8/group) (Harvard University IACUC approved). JTA gel disks (diameter 4 mm, thickness 0.5 mm) were prepared using aseptic techniques and implanted on the central midsubstance of patellar tendons (IACUC approved). To evaluate the effect of the JTA on tendon healing, rats received bilateral full-thickness-partial-width (~50%) excisional injuries to their patellar tendons prior to JTA placement, and were euthanized 3-weeks post injury and JTA placement. Briefly, animals were anesthetized with isoflurane (2-2.5 vol %) while an 8 mm incision through skin superficial to the patellar tendon was made. For tendon injury, the retinaculum on either side of the patellar tendon was cut and a spatula coated with a rubber backing was placed deep to the tendon. A 2 mm biopsy punch was then used to create a full thickness partial width defect in the central patellar tendon midsubstance. In both uninjured and injured animals, the JTA was then implanted in the tendon midsubstance. Gentle pressure on the JTAs was applied for 4 minutes during which adhesion was generated. The skin was then closed with a 4-0 Vicryl suture and animals were returned to cage activity during which post-operative buprenorphine (0.5 mg/kg, Buprenex) was given subcutaneously every 12 hours for three days. For drug delivery experiments, similar procedures were performed on female Sprague Dawley rats (age: 16 weeks; body weight: 300-350 g, Charles River Laboratories) (N=24). Following surgery, a single dose of sustained release buprenorphine (72h release) (0.05 mg/kg, Zoo-Pharms) was given.

Supraspinatus Tenotomy: Adult female Sprague Dawley rats (age: >6 months; body weight: 300 to 400 g) were used. Aseptic surgical procedures were performed under general inhalation anesthesia with isoflurane (1.5-3 vol %). A 15-mm skin incision was made from the acromion towards the humerus bone using a scalpel to expose the deltoid muscle. A 10-mm incision through deltoid muscle was then performed from the humerus towards the acromion to expose the acromion and humeral head. The supraspinatus tendon was then pulled from the subacrominal space with spinal cord hooks and kept under moderate tension. To create the full thickness partial tenotomy, a 23G cannula was positioned along the long axis of the tendon to guide cutting using a scalpel. To implant the JTA (length 6 mm, width 2 mm), the shoulder was abducted and the acromion elevated to allow positioning of the JTA. The JTA was positioned over the supraspinatus enthesis and tendon, and deep to the acromion for additional anchoring. Pressure was applied for 4-minutes using a thin spatula after which the acromion was lowered. The deltoid muscle was then closed by a continuous suture and the skin by a continuous intra-cutaneous suture (Safil 6-0). After recovery from anesthesia, rats were given doses of buprenorphine (2 doses/day for 3 days) and returned to cage activity. Experiments were conducted according to the Swiss laws for animal experimentation and following approval by the veterinarian authorities from the Canton of Basel-Stadt.

High Frequency Ultrasound Imaging (HFUS): HFUS (Vevo 770 Scanner; 35 MHz (RMV712); axial resolution: 50 μm, lateral resolution: 140 μm, depth of view: 15 mm; VisualSonics, Toronto, Canada) was used to evaluate gel swelling in vivo, tendon cross sectional area, and tendon echogenicity in the axial plane. Briefly, after sacrifice, rats were positioned supine on a stage. Knees were shaved and hair was removed using depilatory cream. For imaging of hydrogels, ultrasound images were acquired every 0.5 mm throughout the hydrogel diameter (~4 mm). For analysis, hydrogels were segmented in MATLAB (vR2017a; Mathworks, Natick MA) and the three centermost images were averaged for JTA thickness. For tendon images, tissues were first fine dissected (see fine dissection methods) prior to mounting in a 3D printed device to maintain horizontal orientation of the unloaded patellar tendon. Samples were submerged in a 1×PBS bath during imaging. Axial images were acquired every 0.5 mm throughout the length of the tendon. For analysis of tendon morphology, tendon sections were segmented from each image slice in MATLAB (vR2017a; Mathworks, Natick, MA) and the three center-most images were evaluated for the cross sectional area and echogenicity (Shih, T. Y. et al. Injectable, Tough Alginate Cryogels as Cancer Vaccines. *Adv Healthc Mater* 7, e1701469, doi:10.1002/adhm.201701469 (2018)).

High Frequency Doppler Ultrasound Imaging

High frequency Doppler ultrasound imaging (Vevo 3100 Scanner; 50 MHz transducer; axial resolution: 20 μm, depth of view: 15 mm; VisualSonics, Toronto, Canada) was used to evaluate placement of JTA and vascularity longitudinally in live animals. Briefly, animals were anesthetized with 1.5-2.5% isoflurane and kept supine on a heated platform during imaging. Knees were shaved and hair was removed using depilatory cream. Vital signs were taken to respiratory gate image acquisition during breathing. The knee was bent at approximately 90° while B-mode and Doppler images in the axial plane were taken using a motorized transducer (0.25 mm increments) throughout the length of the patellar tendon (~8 mm). Data were analyzed in VevoLab (Visual-Sonics) using the Doppler ultrasound module to compute total vessel volume in segmented images.

Rotator Cuff Biocompatibility: The effect of tough gel adhesive implantation on intact and injured supraspinatus tendons was evaluated in rats (N=10). Tough gel adhesives (L=6 mm, Th=0.75 mm) were prepared using aseptic techniques and implanted subacrominally, dorsal to the midsubstance of the either intact or injured (sagittal tenotomy) supraspinatus tendon in rats (IACUC approved).

Magnetic Resonance Imaging (MRI): In vivo MRI measurements were performed with a Pharmascan 7 Tesla scanner (Bruker Medical Systems, Etlingen, Germany). Following an induction period with isoflurane 4%, during acquisitions rats were anesthetized with isoflurane 1.5-2% in air, administered via a nose cone. Sagittal and axial images were acquired using a Turbo-RARE sequence (effective echo time 21 ms, repetition time 5600 ms, RARE factor 4, field-of-view 4×3 cm (sagittal) or 3×4 cm (axial), matrix 256×192, slice thickness 0.4 mm, 30 slices) to evaluate the anatomical position of the JTA over time and to assess inflammatory tissue response to the JTA. Maintenance of position of the JTA over time was evaluated by comparing the position of the JTA relative to its location immediately following surgery. Changes in the normalized T2-weighted signal within the supraspinatus was compared over time to determine potential inflammation (higher T2-weighted signal indicates fluid as an indicator for inflammation).

Histology: Shoulders were fixed in 4% PFA, sectioned (5 μm), and stained (H&E).

Patellar Tendon Histology: Following euthanasia, patellar tendons were collected and immersed in 4% PFA for 24 hours before being washed in 1×PBS and transferred to 70% ethanol. Samples were then processed, embedded in paraffin, and sectioned (5 μm) in the sagittal plane. Tissue sections were then stained with hematoxylin and eosin and imaged (Axiozoom Tissue Scanner, Zeiss, Germany). Images were then processed using CellProfiler for cellularity and nuclear shape. Briefly, after cropping the region of interest, a color deconvolution algorithm was applied to separate the histological stains based on absorbance values. Next, the deconvolved hematoxylin image was processed with a two class Otsu thresholding algorithm to identify and segment the cell nuclei. Lastly, a processing module was applied to extract nuclear area, shape, and number.

Supraspinatus Tendon Histology: Following the last MRI imaging, rat shoulders were collected and immersed for 72 hours in 10% neutral buffered formalin (NBF), and then transferred to a decalcification solution (ImmunoCal #1440, Decal Chemical Corp, Suffern, NY) for 5-7 days with daily changes, until decalcification was complete as verified chemically using a procedure previously described (Verdenius, H. H. & Alma, L. A quantitative study of decalcification methods in histology. *Journal of clinical pathology* 11, 229-236 (1958)). After bisection in the coronal anatomic plane to expose the mid-plane of the rotator cuff, samples were dehydrated and paraffin embedded. Then 5-μm thick coronal sections were obtained and stained with hematoxylin (3 minutes) and eosin (30 seconds) (H&E) using a ST5010 Autostainer XL (Leica), and mounted in Pertex®

(#41-4011-00, Medite). HE-stained slides were scanned with an Aperio slide scanner (Leica) for general observations.

Cell Isolation and Viability: Tendon cells were isolated from the Male F344XBN rats at 8 months of age acquired from the National Institute of Aging (Pardes, A. M. et al. Aging leads to inferior Achilles tendon mechanics and altered ankle function in rodents. *In Review* (2016)). Rats were euthanized and flexor digitorum longus tendons with the surrounding paratenon and epitenon were dissected using sterile technique and kept on ice in Dulbecco's Modified Eagle's Medium (DMEM) (Invitrogen). Tendons were then minced and digested in 0.5% type I collagenase (Worthington) and 4 U/ml dispase (Stem Cell Technologies) in HBSS for 4 hours at 37° C. From digests, cells were strained, collected, and resuspended in media (Mienaltowski, M. J., Adams, S. M. & Birk, D. E. Regional differences in stem cell/progenitor cell populations from the mouse achilles tendon. *Tissue Eng Part A* 19, 199-210, doi:10.1089/ten.TEA.2012.0182 (2013)). Tendon cells were cultured in DMEM with 10% Fetal Bovine Serum (Invitrogen) and 1% penicillin/streptomycin (Invitrogen). For cytocompatibility testing in the presence of the tough gel, tendon derived cells were incubated with or without tough hydrogels (diameter 3 mm, thickness 1.5 mm) for 1 and 2 days. For cytocompatibility testing in the presence of CORT releasing gels, tendon derived cells were incubated with tough hydrogels containing 0 µg, 0.53 µg, or 0.212 µg of CORT (diameter 3 mm or 6 mm, thickness 1.5 mm at 10 mg/ml loading) (FIGS. 3A and 3B). Cell viability was assessed by trypan blue staining (Strober, W. Trypan blue exclusion test of cell viability. *Curr Protoc Immunol* Appendix 3, Appendix 3B, doi:10.1002/0471142735.ima03bs21 (2001)) after incubating gels containing CORT in transwells and quantified using an automated counter (Countess II Automated Cell Counter system, ThermoFisher, Waltham, MA).

Dynamic Mechanical Testing

Following rat euthanasia at 3-weeks post injury and/or JTA implantation, patella-patellar tendon-tibia samples were harvested and fine dissected. Briefly, surrounding musculature, adipose tissue, and non-tendon connective tissue were carefully removed using stereomicroscopy while maintaining tissue hydration (1×PBS). Fine dissected tendon samples were then stamped into a dog bone shape to isolate the injury region, leaving a 2 mm width at the center. Tendons were then imaged using HFUS to determine their echogenicity and cross sectional area while being submerged in 1×PBS. For mechanical testing, tendons were secured in custom fixtures submerged in a 1×PBS bath. Briefly, the tibial end was mounted in an acrylic pot using liquid metal and the patellar end was gripped in a custom fixture to secure the patella in a manner which did not stress the tendon. The samples were mounted while submerged in a 1×PBS bath at room temperature in a dynamic mechanical testing frame (Electroforce 3200, TA Instruments, Minnesota). A comprehensive mechanical test was then completed to evaluate tendon viscoelastic, dynamic, and quasi-static mechanical properties (FIG. 26A). Briefly, samples underwent preloading (0.1 N), preconditioning (30 cycles at 0.25-0.5% strain), stress relaxation (4% strain), a dynamic frequency sweep (0.1, 1, 5, and 10 Hz) at a strain amplitude of 0.125%, and a ramp to failure (0.05% strain/s) using a 225 N load cell. Displacement and force data collected during loading were processed using custom MATLAB software (vR017a; Mathworks, Natick, MA) to compute the percent relaxation, relaxation half time, dynamic modulus, tan δ, toe modulus, linear modulus, transition strain, and failure stress (Freedman, B. R. et al., Biomechanical and structural response of healing Achilles tendon to fatigue loading following acute injury. *J Biomech* 47, 2028-2034, doi:10.1016/j.jbiomech.2013.10.054 (2014); Freedman, B. R. et al., Evaluating changes in tendon crimp with fatigue loading as an ex vivo structural assessment of tendon damage. *J Orthop Res* 33, 904-910, doi:10.1002/jor.22875 (2015); Peltz, C. D. et al. The effect of postoperative passive motion on rotator cuff healing in a rat model. *J Bone Joint Surg Am* 91, 2421-2429, doi:10.2106/JBJS.H.01121 (2009); Freedman, B. R. et al. Nonsurgical treatment and early return to activity leads to improved Achilles tendon fatigue mechanics and functional outcomes during early healing in an animal model. *J Orthop Res* 34, 2172-2180, doi:10.1002/jor.23253 (2016)).

Drug Loading and Release: Micronized CORT morphology was assessed using scanning electron microscopy. Tough gel adhesives (Th=0.75 mm, D=3 mm) were loaded with 1, 10, or 100 mg/ml corticosteroid and (also 20, 40, 80 and 120 mg/ml laponite in Example 7) examined for release in sink conditions (HBSS) and following lyophilization. Sink conditions were defined as the required volume of water to solubilize the loaded amount of CORT within the hydrogel. Released drug was sampled daily and evaluated using liquid chromatography-mass spectrometry (Agilent 1290/6140, Gradient method; SIM mode). Chromatographic separation was performed at RT using an HPLC column (Agilant Zorbax Rx-C18; ID: 2.1 mm, L:150 mm). A two-solvent linear gradient method was used (A: 0.02% formic acid; B: methanol). Drug release was quantified by integrating the characteristic peak. For studies that evaluate the effects of temperature on drug release, the incubation temperature of the tough gel adhesives were raised on days 3, 6, and 9 over the course of the studies that spanned 13 days. The released drug was sampled daily. As for studies that evaluate the effects of sonication on drug release, after burst release was accounted for, ultrasound stimulated release at 40% of max intensity. The released drug was sampled daily.

Computational Modeling

Franz Cell Simulations

Diffusion of dissolved triamcinolone acetonide in the unloaded hydrogel was modelled and matched with wetbench diffusion data derived from standard unjacketed Franz diffusion cell experiments performed at room temperature. The volume of the donor compartment was 1 ml (unstirred) and the volume of the acceptor compartments was 5 ml (well-stirred). The starting concentration of triamcinolone acetonide in the donor compartment was 20 µg/ml (Figure C). The donor compartment was separated from the acceptor compartment either by a PVDF membrane [mechanical support of the hydrogel, thickness 125 µm, pore size 0.45 µm, porosity 70%, (Durapore NF-HVLP02500)] or a combination of the PVDF membrane and the hydrogel (thickness 750 µm).

The time transient diffusion equation (Eq 2) was solved in 2D axissymmetric form, using the concentration c and the diffusion constant D. The acceptor compartment was well stirred, thus the diffusion constant was set large enough to enforce instant distribution (Gudnason, K., Sigurdsson, S. & Jonsdottir, F. A Numerical Framework for Diffusive Transport in Rotational Symmetric Systems with Discontinuous Interlayer Conditions. *IFAC=PapersOnLine* 51, 5, doi: https://doi.org/10.1016/j.ifacol.2018.03.109 (2018)). In contrast, the donor compartment was unstirred and the diffusion constant of triamcinolone acetonide in water was approximated to 436 $\mu m^2$/s at 20° C. (Wilke, C. R. & Chang, P. Correlation of Diffusion Coefficients in Dilute Solutions. *AIChE* 1, 7 (1955)).

Wet-bench diffusion data were used to adjust the simulated apparent diffusion constants of dissolved triamcinolone acetonide in the unloaded hydrogel. The simulated apparent diffusion constant of triamcinolone acetonide in the PVDF membrane was 305 $\mu m^2$/s. In a second simulation, the apparent diffusion constant in the PVDF membrane was fixed and the apparent diffusion constant of triamcinolone acetonide in the hydrogel only was 16 $\mu m^2$/s.

Dissolution and Transport Kinetics of Triamcinolone from the JTA

In order to simulate the dissolution and transport kinetics of embedded triamcinolone acetonide crystals from the dissipative hydrogel under sink conditions, a 3D Finite Element Model (FE-model) was developed using the module 'Transport of Diluted Species' of the Finite Element Software COMSOL Multiphysics (Release 5.5). In the 3D FE-model, each spherical triamcinolone acetonide crystal was surrounded by a cubical volume of the hydrogel. The FE-model consisted of 8 cubical units with a side length of 46.8 $\mu m$ resulting in a total length of 375 $\mu m$ of the FE-model probe. The FE-model probe had symmetry conditions on all sides, except at the interface to the acceptor compartment. The acceptor compartment was modelled as a well-stirred water-filled compartment with the total volume replaced every 24 hours. At time point 'zero' of the simulation, the concentration of triamcinolone acetonide was set to 'zero' in the hydrogel and the acceptor compartment. With this modular approach, the dissolution and transport kinetics of triamcinolone acetonide crystal, embedded in the hydrogel was simulated at the two triamcinolone acetonide loadings of 10 mg/ml and 100 mg/ml.

Dissolution of embedded triamcinolone acetonide crystals at the crystal hydrogel phase boundary was modelled in thermodynamically equilibrium using the maximum solubility of triamcinolone acetonide. The mass flux of triamcinolone was calculated by Fick's law, with the main variables diffusion constant and solubility in the hydrogel phase (Eq 1).

$$C_{sol_{(water\ 37°\ C.)}}=33\ \mu g/ml \qquad \text{(Eq 1)}$$

With progressing dissolution, the embedded triamcinolone acetonide spherical crystals were modeled to shrink in diameter. This change in geometry of the spherical crystals and the consequence on dissolution of triamcinolone acetonide crystals at the crystal hydrogel phase boundary was modelled by a moving interface. The outer shape of the hydrogel was fixed.

Dissolution and diffusion of triamcinolone acetonide (10 mg/ml and 100 mg/ml) embedded as spherical crystals in the hydrogel to a well-stirred water-filled acceptor compartment was modelled and matched with wet-bench transport kinetic data at 37° C. The time transient 3D diffusion equation (2) was solved, using the concentration c and the diffusion constant D (Eq 2).

$$\frac{\partial c}{\partial t} - \nabla \cdot (D\nabla c) = 0 \qquad \text{(Eq 2)}$$

Because well-stirring was applied in the acceptor compartment, the diffusion constant in the acceptor compartment was set large enough to enforce instant distribution 70. Wet-bench transport kinetic data were used to adjust the simulated apparent diffusion constants of triamcinolone acetonide in the drug-loaded hydrogel. Following dissolution of triamcinolone acetonide crystals embedded in the hydrogel (Csol=33 $\mu g$/ml), the simulated apparent diffusion constants increased with drug load, from 153 $\mu m^2$/s (10 mg/ml) to 273 $\mu m^2$/s (100 mg/ml). In comparison, the diffusion constant of triamcinolone acetonide in water is reported to be 673 $\mu m^2$/s (Seki, T. et al. Measurement of diffusion coefficients of parabens and steroids in water and 1-octanol. *Chem Pharm Bull (Tokyo)* 51, 734-736, doi: 10.1248/cpb.51.734 (2003)).

Flexor Tendon Testing in Human Cadavers: Human fore limbs were surgically prepared using an LCP Volar Rim Distal Radius (LLP) (DePuy Synthes, West Chester, PA). The distal radius was approached using a volar incision over the flexor carpi radialis tendon. After elevation of the pronator quadratus muscle, the implant was fixed to the distal radius using a single cortical screw in an oblong hole. Plates were positioned at Soong 0 (pVA-LCP) or Soong 2 (dVA-LCP) position relative to the watershed line and the position was confirmed with fluoroscopy. No fractures were created in this model. Distal row locking holes were filled using a fixed angle guide with 2.4 mm diameter screws that were sized appropriately for the specimen. The pronator quadratus was excised to mimic irreparable disruption observed after distal radius fractures. JTAs ($10\times40\times1\ mm^3$) were adhered to the underside of the flexor *digitarum profundus* tendon. Flexion/extension of the thumb was used to test their attachment and ability to glide over the volar plate and transverse carpal ligaments.

Passive Diffusion Studies: To examine the influence of the tough hydrogel and adhesive on corticosteroid diffusion, we conducted diffusion experiments with a Franz cell. Over time, the receptor chamber was sampled to determine the concentration of drug diffusing through a non-gel membrane, tough gel, and tough adhesive.

Statistical Analysis: Data normality was assessed with Shapiro Wilk tests (SPSS). One-way (time) or two-way (healing and JTA implantation) ANOVA tests were used to evaluate the effects of time, injury, or treatment on all properties assessed. Significant factors were evaluated using post hoc Student's t-tests with Bonferroni corrections for multiple comparisons.

Example 2. Tough Gel Adhesives as Local, Tunable, Extended Drug Delivery Systems Tendon injuries are common and often accompanied by tissue inflammation, degeneration, and are also recognized complications following bone fracture fixation (Surgeons, A. A. o. O. Optimizing the Management of Rotator Cuff Problems. (2013); Iannotti, J. P. Full-Thickness Rotator Cuff Tears: Factors Affecting Surgical Outcome. *J Am Acad Orthop Surg* 2, 87-95 (1994); Goutallier, D., Postel, J. M., Gleyze, P., Leguilloux, P. & Van Driessche, S. Influence of cuff muscle fatty degeneration on anatomic and functional outcomes after simple suture of full-thickness tears. *J Shoulder Elbow Surg* 12, 550-554, doi:10.1016/S1058274603002118 (2003); McCarron, J. A. et al. Failure with continuity in rotator cuff repair "healing". *Am J Sports Med* 41, 134-141, doi:10.1177/0363546512459477 (2013); Rodeo, S. A. Biologic augmentation of rotator cuff tendon repair. *J Shoulder Elbow Surg* 16, S191-197, doi:10.1016/ j.jse.2007.03.012 (2007). Although many new surgical, rehabilitation, graft, and drug therapeutics have been proposed (Watts, A. E. et al. MicroRNA29a Treatment Improves Early Tendon Injury. *Mol Ther* 25, 2415-2426, doi:10.1016/j.ymthe.2017.07.015 (2017); Millar, N. L. et al. MicroRNA29a regulates IL-33-mediated tissue remodelling in tendon disease. *Nat Commun* 6, 6774, doi:10.1038/ncomms7774 (2015); Li, J. et al. Tough Composite Hydrogels with High Loading and Local Release of Biological Drugs. *Adv Healthc* Mater 7, e1701393, doi:10.1002/adhm.201701393 (2018); Gelberman, R. H. et al. Combined Administration of ASCs and BMP-12 Promotes an M2 Macrophage Phenotype and Enhances Tendon Healing. *Clin Orthop Relat Res* 475, 2318-2331, doi:10.1007/s11999-017-5369-7 (2017); Freedman, B. R. & Mooney, D. J. Biomaterials to Mimic and Heal Connective Tissues. *Adv Mater* 31, e1806695, doi:10.1002/adma.201806695 (2019)), with some taken to market (Freedman & Mooney, supra; Murray, M. M. et al. The Bridge-Enhanced Anterior Cruciate Ligament Repair (BEAR) Procedure: An Early Feasibility Cohort Study. *Orthop J Sports Med* 4, 2325967116672176, doi:10.1177/2325967116672176 (2016); Shoaib, A. & Mishra, V. Surgical repair of symptomatic chronic achilles tendon rupture using synthetic graft augmentation. *Foot Ankle Surg* 23, 179-182, doi:10.1016/j.fas.2016.04.006 (2017)), failed tendon healing and persistent pain remain significant unmet medical needs. New biomaterial-based therapies may address these unmet needs by providing mechanical support and effective spatial and temporal targeted delivery of drug therapeutics to tendon tissue (Mitragotri, S., Burke, P. A. & Langer, R. Overcoming the challenges in administering biopharmaceuticals: formulation and delivery strategies. *Nat Rev Drug Discov* 13, 655-672, doi:10.1038/nrd4363 (2014); Anselmo, A. C. & Mitragotri, S. Nanoparticles in the clinic: An update. *Bioeng Transl Med* 4, e10143, doi:10.1002/btm2.10143 (2019)). Use of hydrogels may be particularly appealing due to their general biocompatibility with surrounding tissues, the tunability of their physical properties, and their ability to serve as a depot for drug delivery. However, hydrogels typically exhibit poor mechanical toughness and adhesive properties, and rely on cell infiltration or suturing to integrate with surrounding tissue, and frequently exhibit burst release of drugs (Li, J. & Mooney, D. J. Designing hydrogels for controlled drug delivery. *Nat Rev Mater* 1, doi:10.1038/natrevmats.2016.71 (2016)).

To promote tendon healing by providing mechanical support and by local delivery of drug therapeutics, hydrogels should be placed and remain near the relevant anatomical site. If used for spatial and temporal targeted delivery of therapeutics, hydrogels are considered to reduce potential systemic toxicity and side effects (Bjarnason, I., Hayllar, J., MacPherson, A. J. & Russell, A. S. Side effects of nonsteroidal anti-inflammatory drugs on the small and large intestine in humans. *Gastroenterology* 104, 1832-1847, doi:10.1016/0016-5085(93)90667-2 (1993)) commonly associated to orally delivered medications such as NSAIDs (Svanstrom, H., Lund, M., Melbye, M. & Pasternak, B. Concomitant use of low-dose methotrexate and NSAIDs and the risk of serious adverse events among patients with rheumatoid arthritis. *Pharmacoepidemiol Drug Saf,* doi:10.1002/pds.4555 (2018); Blomquist, J., Solheim, E., Liavaag, S., Baste, V. & Havelin, L. I. Do nonsteroidal anti-inflammatory drugs affect the outcome of arthroscopic Bankart repair? Scand *J Med Sci* Sports 24, e510-514, doi:10.1111/sms.12233 (2014); Soreide, E. et al. *The Effect of Limited Perioperative* Nonsteroidal Anti-inflammatory Drugs on Patients Undergoing Anterior Cruciate Ligament Reconstruction. *Am J Sports Med* 44, 3111-3118, doi: 10.1177/0363546516657539 (2016); Oh, J. H. et al. Do Selective COX-2 Inhibitors Affect Pain Control and Healing After Arthroscopic Rotator Cuff Repair? A Preliminary Study. *Am J Sports Med* 46, 679-686, doi:10.1177/0363546517744219 (2018)) and promote local drug retention and extended dosing intervals following injection of drugs such as corticosteroids (Kwon, H. H. et al. Synergistic effect of cumulative corticosteroid dose and immunosuppressants on avascular necrosis in patients with systemic lupus erythematosus. Lupus, 961203318784648, doi:10.1177/0961203318784648 (2018); Wang, J. C., Chang, K. V., Wu, W. T., Han, D. S. & Ozcakar, L. Ultrasound-Guided Standard vs Dual-Target Subacromial Corticosteroid Injections for Shoulder Impingement Syndrome: A Randomized Controlled Trial. *Arch Phys Med Rehabil* 100, 2119-2128, doi: 10.1016/j.apmr.2019.04.016 (2019); Hugate, R., Pennypacker, J., Saunders, M. & Juliano, P. The effects of intratendinous and retrocalcaneal intrabursal injections of corticosteroid on the biomechanical properties of rabbit Achilles tendons. *J Bone Joint Surg Am* 86, 794-801, doi: 10.2106/00004623-200404000-00019 (2004); Zhang, B., Hu, S. T. & Zhang, Y. Z. Spontaneous rupture of multiple extensor tendons following repeated steroid injections: a case report. *Orthop Surg* 4, 118-121, doi:10.1111/j.1757-7861.2012.00170.x (2012)). However, following injection or implantation of hydrogels physical distortion by movement can lead to displacement over time and to mechanical fragmentation of the gels (Freedman & Mooney, supra; Markl, D. & Zeitler, J. A. A Review of Disintegration Mechanisms and Measurement Techniques. *Pharm Res* 34, 890-917, doi:10.1007/s11095-017-2129-z (2017)). Tissue adhesives approved for medical use such as fibrin glues (TISSEL®) and cross-linked polyethylene glycols (DuraSeal®) may be used as adhesive hydrogels, however their adhesive strength is low. Cyanoacrylates (Dermabond®) are tissue adhesives with high mechanical strength (Linderman, S. W. et al. Shear lag sutures: Improved suture repair through the use of adhesives. *Acta Biomater* 23, 229-239, doi: 10.1016/j.actbio.2015.05.002 (2015)), however they are cytotoxic to tendon derived cells (Evans, C. E., Lees, G. C. & Trail, I. A. Cytotoxicity of cyanoacrylate adhesives to cultured tendon cells. *J Hand Surg* Br 24, 658-661, doi: 10.1054/jhsb.1999.0279 (1999)), incompatible with wet tissue surfaces (Li, J. et al. Tough adhesives for diverse wet surfaces. *Science* 357, 378-381, doi:10.1126/science.aah6362 (2017)), may chemically react with encapsulated drugs during its setting, and forms rigid connections upon contact with water (Li, J. et al., supra). Furthermore, to protect tendons from tendon injury following bone fracture fixation (e.g., volar plate fixation of distal radius fractures (Mellstrand-Navarro, C., Pettersson, H. J., Tornqvist, H. & Ponzer, S. The operative treatment of fractures of the distal radius is increasing: results from a nationwide Swedish study. *The bone & joint journal* 96-b, 963-969, doi:10.1302/0301-620x.96b7.33149 (2014); Soong, M., Earp, B. E., Bishop, G., Leung, A. & Blazar, P. Volar locking plate implant prominence and flexor tendon rupture. *The Journal of bone and joint surgery. American volume* 93, 328-335, doi:10.2106/jbjs.J.00193 (2011)), adhesive hydrogels should also support tendon gliding (Tang, J. B. Clinical outcomes associated with flexor tendon repair. *Hand Clin* 21, 199-210, doi:10.1016/j.hcl.2004.11.005 (2005); Strickland, J. W. Development of flexor tendon surgery: twenty-five years of progress. *J Hand Surg Am* 25, 214-235, doi:10.1053/jhsu.2000.Thsu25a0214 (2000); May, E. J. &

Silfverskiold, K. L. Rate of recovery after flexor tendon repair in zone II. A prospective longitudinal study of 145 digits. *Scand J Plast Reconstr Surg Hand Surg* 27, 89-94, doi:10.3109/02844319309079789 (1993)).

Figure 1:
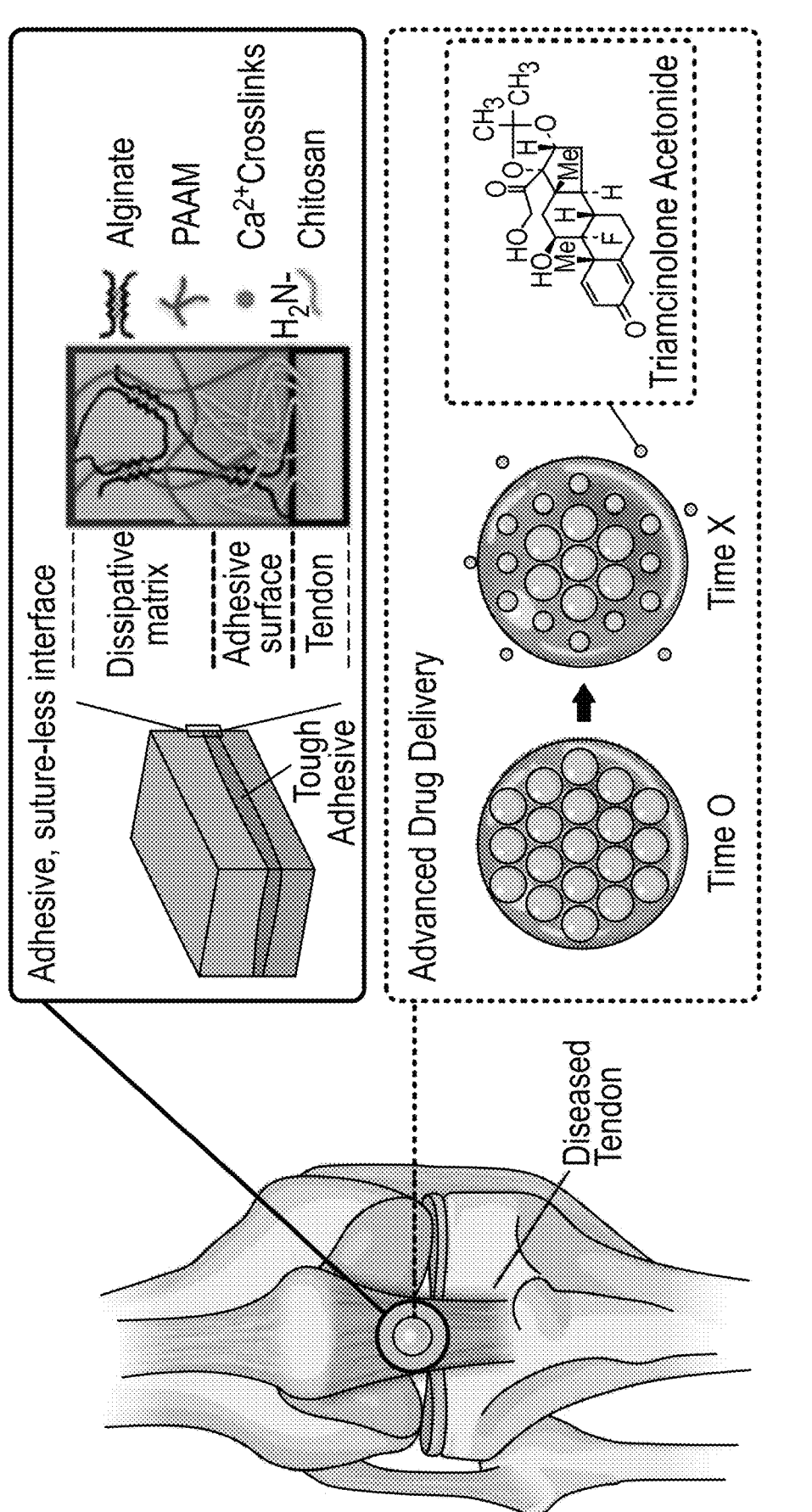
FIG. 1 is a schematic depicting an overview of the vision for the multifunctional performance of the Janus Tough Adhesives (JTAs) for tendon. Exemplary JTA hydrogels were engineered that comprise a tough hydrogel dissipative matrix and adhesive surface, e.g., chitosan surface. Beyond tissue adhesion, the material can serve as a drug delivery system for local release of agents such as triamcinolone acetonide as exemplified in the present disclosure.

In present invention, a novel tough gel adhesive was engineered. The tough gel adhesive with disparate surface properties, termed janus tough adhesive (JTA) with two-directional tissue adherent and tissue gliding properties to serve as a high capacity depot for drug delivery to tendon (FIG. 1). High mechanical toughness of the JTA was achieved through the use of a dual interpenetrating hydrogel network that combines the ability of alginate hydrogels to dissipate energy through dissociation of ionic bonds with a highly elastic covalently cross-linked acrylamide hydrogel that can distribute stresses throughout the network (Zhao, X. Multi-scale multi-mechanism design of tough hydrogels: building dissipation into stretchy networks. *Soft Matter* 10, 672-687, doi:10.1039/c3sm52272e (2014); Sun, J. Y. et al. Highly stretchable and tough hydrogels. *Nature* 489, 133-136, doi:10.1038/nature11409 (2012)). Adhesion to tissue with unprecedented adhesion properties of the JTA, was achieved by unilateral coupling of the amine rich bridging polymer chitosan to the dissipative alginate acrylamide hydrogel (Li, J. et al., supra). It is hypothesized that the JTA will offer new avenues to promote simultaneously mechanical tissue integrity and controlled spatial and temporal drug delivery for the treatment or prevention of tendon injury. The JTA may become a therapeutic platform being widely applicable for various drug therapeutic modalities and many other disease states.

Tough gel adhesive biomaterials inspired by the thick mucus secreted by slugs and that combine an adhesive surface with a dissipative tough gel matrix (see FIG. 1) were prepared to explore these materials to serve as local, tunable, extended drug delivery systems. The application of tough gel adhesive materials in the rotator cuff to augment tendon-bone healing also had not been explored. Therefore, the main objective of this example was to explore implantation and biocompatibility of tough gel adhesives to rat rotator cuff supraspinatus tendon and to determine mechanistically their ability for local drug delivery.

Engineered tough gel adhesives exhibited high mechanical toughness, stretch, and adhesion energies (>800 J m$^{-2}$). After implantation in the rat rotator cuff, the tough gel adhesives remained in place up to 4-weeks regardless of the presence of sagittal tenotomy. The tough gel adhesives were well tolerated and no exaggerated tissue response to the TAs was detected neither in intact nor in rats with sagittal tenotomy, as revealed by MRI T2 contrast-to-noise ratio (CNR) of FIG. 25J. The MRI results were consistent with microscale histological evaluation.

Therefore, the inventors found that the tough gel adhesives adhered strongly to the rat supraspinatus tendon and were well-tolerated.

Example 3. Evaluation of the Physicochemical Properties of Triamcinolone Acetonide (CORT), Effects of CORT on the Mechanical Properties of Tough Gel Adhesives, and Factors Influencing the Release CORT from Tough Gel Adhesives Triamcinolone acetonide (CORT), with the chemical structure shown in FIG. 2A, has a molecular weight of 434.5 g/mol, an acute toxicity in rat of 1451 mg/kg (oral LD50), a white solid appearance, a log P value of 2.5, and a water solubility of 0.02 mg/ml.

The solubility of CORT in various water and other solutions were evaluated over a period of 24 h. As shown in FIG. 2B, the solubility of CORT in ddH$_2$O and also water-based solutions of 2% alginate and 12% acrylamide (i.e., about 0.01-0.1 mg/ml), but could be increased to about 1 mg/ml with the addition of dimethyl sulfoxide (DMSO) at a DMSO:ddH$_2$O ratio of 1:4. FIGS. 2C, 2D, and 2E are micrographs showing the solubility of respectively 0.1 mg/ml, 1 mg/ml, and 10 mg/ml triamcinolone acetonide in a solution of 2% alginate and 12% acrylamide.

When incorporating CORT into the tough gel adhesives, due to the low solubility of CORT in water a release-by-dissolution principle was applied, whereby the hydrogel was loaded with CORT at ~25000×the solubility limit (i.e., 100 mg/ml) (see FIG. 2F).

It was found that CORT did not affect the material toughness. FIG. 2G shows the nominal stress and maximum stretch for tough gels loaded with 10 mg/ml of CORT, which is similar to the curve of an unloaded tough gel (not shown). Similar experiments were repeated and the results are discussed in Example 5 (see FIGS. 5A, 5B, 5C, 5D).

It was also found that CORT does not affect the ability of the tough gel adhesives to adhere to tissue (see FIGS. 2H, 2I). At 0 mg/ml, 1 mg/ml, and 10 mg/ml of CORT, the adhesion of the tough gel adhesives were strong and maintained at least about 700 J/m$^2$.

However, it was found that time and directionality affected CORT release from the tough gel adhesives. As shown in FIG. 2J, the CORT release rate was higher when the tough gel adhesives were immersed freely in an Eppendorf tube, than when they were affixed to the base of a Transwell. FIG. 2K shows minimal release of CORT into the chitosan adhesive layer and the Transwell after about 90 minutes, regardless of the concentration of the drug in the tough gel (1 mg/ml, 10 mg/ml, or 100 mg/ml).

The amount of the area of the hydrogel covered by 1 mg/ml, 10 mg/ml, or 100 mg/ml CORT was also studied (see FIGS. 2L, 2M).

Finally, as shown in FIG. 2N, it was found that buffer conditions did not affect the release kinetics of CORT from the tough gel adhesives.

Accordingly, the inventors found that when CORT was incorporated into the tough gel adhesives, the release rate was primarily governed by drug dissolution due to the low solubility of CORT in water and was modulated by drug loading. It was found that unlike traditional hydrophilic hydrogels that exhibit poor mechanical strength and low drug loading, the tough gel adhesives described herein were capable of drug loading beyond >10% of the weight of the hydrogel, which is unprecedented for hydrogels, as shown in FIG. 2O. Specifically, the tough gel adhesives were loaded up to 100 mg/ml (10% wt), which is a ~10-fold higher loading than achieved with typical hydrogels. The cumulative release of CORT from tough gel adhesives loaded with 100 mg/ml CORT is shown in FIG. 2P. The ability of the tough gel adhesives to maintain their unprecedented mechanical properties up to 100 mg/ml loading, is important for strong adhesion generation. This "over-loading" strategy may also be particularly attractive to other hydrogel systems that lose physical integrity during handling or functioning in dynamic tissue environments (e.g., a beating heart), which can change release. Due to the high drug loading, it was observed that the CORT particles formed aggregates at higher loadings, as shown in FIGS. 2Q, 2R, and 2S.

Example 4. Cell Viability Studies and Extended Release In Vivo ext, the cell viability of tough gel adhesives loaded with CORT were studied. FIG. 3A illustrates the experimental design of the cell viability studies. Briefly, tendon cells that had been treated with unloaded tough gel adhesives or tough gel adhesives loaded with 53 or 212 µg CORT were isolated from the rat flexor digitorum longus tendon, followed by mincing of the isolated tendon cells and addition of collagenase-I and dispase, and seeded in 24-well plates using DMEM, 10% FBS, and 1% penicillin-streptomycin. Cell viability was assessed by trypan blue staining after incubating gels containing corticosteroid (CORT) in Transwells. It was found that the tough gel adhesives loaded with 53 µg or 212 µg CORT were well-tolerated by the rat tendon cells (see FIG. 3B), and the drug could be successfully released in vivo, as evidenced by the drug release and serum exposure curves of FIG. 3C. The mechanical properties of the adhesives before and after release of CORT were also measured, as shown in FIGS. 3D, 3E. The tough gel adhesives were shown to have decreased in their compressive stress after the drug release.

Example 5. Further Studies of CORT and Effects on the Mechanical Properties on Tough Gel Adhesives Different batches of CORT were acquired and experimented with. Specifically, CORT was acquired from two suppliers, namely Toronto Research Chemicals (TRC) and Sandoz (NIBR). Firstly, the morphology of the dry CORT powder from both suppliers was studied using single electron microscopy (SEM) (see FIGS. 4A, 4B, 4C, 4D). Table 1 below shows the Triamcinolone acetonide crystals sizes under SEM.

TABLE 1

| Size of Dry Corticosteroid Particles from Sandoz and TRC | | | | |
| | ×10 (µm) | ×50 (µm) | ×90 (µm) | D(4,3) (µm) |
| --- | --- | --- | --- | --- |
| Sandoz | 1.24 | 2.84 | 5.62 | 3.27 |
| TRC | 2.82 | 15.29 | 47.52 | 21.79 |

Next, the morphology of the dry CORT powder from both suppliers in monomer solutions at 1 mg/ml, 10 mg/ml, or 100 mg/ml CORT was studied (see FIGS. 4E, 4F, 4G, 4H, 4I, 4J). Referring to 4K, as expected, the percentage of area covered by CORT in the monomer solutions increased with increasing CORT concentrations. As shown in FIGS. 4L, 4M, 4N, 4O, 4P, and 4Q, hydrogels made with the CORT obtained from TRC were found to be more homogeneous, which could be attributed to the fact that the TRC CORT was micronized (see more detailed discussion in Example 6). FIGS. 4U, 4V and 4W show that, seven days after subcutaneous injection into rats, CORT (at 10 mg/ml or 100 mg/ml) had not been completely release from the tough gel adhesives in vivo.

FIGS. 4R and 4S show that increased CORT concentrations extend release and reduce the release rate from the tough gel adhesives, and similar experiments were repeated in FIG. 5E and the results were consistent. FIG. 4T shows that the CORT from Sandoz (NIBR) released at a higher rate.

Corroborating with Example 2 and FIG. 2G, it was found that increased CORT loading had no effect on the stretch of the tough gel adhesives (see FIGS. 5A, 5B). However, FIGS. 5C and 5D show that increased CORT increases the peak stress of the tough gel adhesives.

Example 6. Further Additives in Tough Gel Adhesives and Effects on Mechanical Properties of Tough Gel Adhesives Attempts were made to improve the refinement of the particle size of CORT, which thereby improve the homogeneity of the tough gel adhesives loaded with CORT.

Poloxamer 188 (P188), a wetting agent, appeared to effectively improve the homogeneity of the tough gel adhesives loaded with CORT by inclusion of 1% of the substance (see FIGS. 6A, 6B, 6C, 6D, 6E).

Polyvinylpyrrolidone (PVP), an agent capable of altering viscosity, appeared to have minimal effects on the homogeneity of the tough gel adhesives loaded with CORT (see FIGS. 7A, 7B, 7C, 7D).

Hydroxypropyl cellulose (HPC), a solubilizer, appeared to effectively improve the homogeneity of the tough gel adhesives loaded with CORT with increasing concentrations of the substance (see FIGS. 8A, 8B, 8C, 8D).

The effects of each of P188, PVP, and HPC on the compressive modulus, stretch, and stress properties of the tough gel adhesives loaded with CORT were also studied (see FIGS. 9A, 9B, 9C). HPC was found to have a detrimental effect on all three mechanical properties.

Example 7. CORT-Tough Gel Adhesives with Laponite

Tough gel adhesives with laponite and loaded with CORT were developed for improved controlled release of therapeutic agents (e.g., corticosteroids) to, for example, tendon tissue. The inventors hypothesized that corticosteroids (non-ionic) could be encapsulated in the hydrophobic interlayer spaces of laponite clay aggregates or adsorbed onto the laponite aggregates (see FIG. 10A, 10B). Specifically, clay nanoparticles carrying negative charge are hypothesized to self-assemble into nano- and micro-sized particles that provide a large surface area for the adsorption of charged drugs (e.g., positively charged drug molecules), thereby decelerating the release of the drugs from the tough gel compositions. The micrographs of FIGS. 11A, 11B, 11C, 11D, and 11E confirmed the formation of the laponite-clay macroparticles. With higher LAP:CORT ratios, more laponite-CORT aggregates are found consistently throughout the gel, thereby leading to colloidal stability. FIG. 10C shows that hydrogen bonds may also form between the hydroxyl and carbonyl groups of CORT molecules. It is also hypothesized that the clay nanoparticles can be pH-responsive, where low pH can protonate negative charges on the clay particles, thereby weakening drug-clay interactions and accelerating the drug release.

The mechanical properties (FIGS. 12A, 12B, 13B, 13C) and the drug release kinetics (FIGS. 18A-18C) of the tough gel-laponite adhesives loaded with CORT were evaluated. It was found that the hydrogels loaded up to 8% laponite exhibited excellent mechanical toughness (4.06±1.2 kJ/m²), stretch (15.6±2.3 mm/mm), and strong adhesion. Corticosteroids maintained colloidal stability even at high drug loadings (zeta potential=−18.1±3.3 mV) (FIG. 13A). These physical and chemical interactions resulted in extended, low burst accumulative drug release for scaffolds at 1 and 10 mg/ml (but not 100 mg/ml) loadings containing higher laponite (i.e., 8% laponite (80 mg/ml) vs. 4% laponite (40 mg/ml)) to drug concentration as compared to non-laponite gels (p<0.05). Stronger interactions between CORT and laponite when more laponite is present (p<0.05), higher drug loading did not cause any significant effect.

Taken together, this study developed a novel corticosteroid delivery system, possessing high mechanical toughness and adhesion, for controlled drug release.

It was also discovered that the first batch of the CORT dry powder obtained from Sandoz (NIBR) was not micronized, but the second batch was (see FIGS. 15A, 15B, 15C, 15D, 15E, 15F). Micronization was found to significantly improve the homogeneity of the hydrogels, as can be seen in the micrographs of FIGS. 16A, 16B, 16C, 16D, 16E. The solubility limits of the micronized Sandoz (NIBR) CORT and the TRC CORT were also evaluated (see FIG. 17). Furthermore, and consistent with the observations made in Example 5, hydrogels made with the CORT obtained from TRC were found to be more homogeneous (see FIGS. 12A, 12B, 12C, 12D, 12E, 12F).

Example 8. Effects of Ultrasonication on Drug Release

As depicted in FIG. 19A, after 5 days of passive, the tough gel adhesives having CORT only or CORT and laponite were ultrasonicated for 3 min at every hour for 5 hours. FIGS. 19B and 19C indicate that the ultrasonication reduced hydrogel size, and FIG. 19D shows that the ultrasonication accelerated the CORT release. FIG. 19E shows that the ultrasound-stimulated release could be slightly decelerated, which is most likely attributed to the laponite-CORT interactions which would have slowed down the release of the drug molecules from the hydrogels.

Example 9. Effects of Temperature on Drug Release

As shown in FIG. 20A, the heat studies involved incubating the tough gel adhesives loaded with 100 mg/ml CORT for a total of 13 days at 4° C., except for days 3, 6 and 9, where the compositions were exposed to heat treatment at 37° C. FIGS. 20B and 20C show that drug release could be controlled by tuning the temperature, and that higher temperatures lead to accelerated drug release.

Example 10. Other Factors Controlling Drug Release

Finally, the effects of the additives P188, PVP, and HPC on tough gel-laponite adhesives were also studied. FIGS. 21B and 21C indicate that PVP and HPC appeared to increase the drug release rate, but also help in controlling the gel swelling. FIG. 21D indicates that combing all three additives, namely P188, PVP and HPC was helpful in decreasing gel swelling. FIG. 21A indicates other conditions that appeared to accelerate CORT release from the hydrogels (using micronized CORT from Sandoz (MBR) at 100 mg/ml), namely high molecular weight alginate and sonication. A mixture of high and low molecular weight alginate appeared to help reduce the drug release. The combination of P188, PVP and HPC, in addition to the desirable effects in reducing gel swelling as shown in FIG. 14D, also appears to slightly help to reduce CORT release, as shown in FIG. 21A.

Example 11. Comparisons Against a Polyvinylidene Fluoride Membrane

As shown in FIG. 22B, the passive diffusions of CORT through a polyvinylidene fluoride (PVDF) membrane, a tough gel, and a tough gel adhesive were compared, The results shown in FIG. 22A indicate that the tough hydrogel and adhesive system can be used to slow drug diffusion. This principle may further control drug release from the tough adhesives and supports the importance of the hydrogel system to control drug dissolution and release.

Example 12. JTA Adheres Strongly to Tendons and Supports Tissue Gliding Ex Vivo The adhesion strength of the JTA to tendon was first investigated. Bovine tendon samples were prepared by cutting tissues into thin tendon planks using a cryotome (FIG. 23A and FIG. 24A). After applying the positively charged bridging polymer chitosan to the tough dissipative alginate acrylamide hydrogel (FIG. 23B), the chitosan diffused into the tough hydrogel and tendon surfaces rapidly (FIGS. 23C and 23D) and generated strong adhesion (FIG. 23E). The adhesion energy increased over time exceeding the fibrin glue TISSEEL® within one minute (FIG. 23F). Because of the one-sided tissue adherence of the JTA only, it was hypothesized that the opposite non-adherent side of the JTA may even support tendon gliding. Indeed, friction testing revealed that the non-adherent surface demonstrated very low coefficients of friction GO of JTA on adjacent tissue, even below that of tissue on tissue (FIGS. 23G and 23H).

Example 13. JTA is Biocompatible and Promotes Tendon Healing In Vitro and In Vivo Tendon derived cells maintained high viability (>95%) in vitro following incubation with JTA (FIGS. 3A and 3B). To evaluate the performance of the JTA in vivo, rats with full thickness, partial width excisional injuries made to the central midsubstance of their patellar tendons, or left uninjured, were either treated with the JTA or left untreated (FIG. 25A). The physical integrity of the JTA was assessed longitudinally as JTA thickness in vivo to evaluate any potential swelling or degradation using high frequency ultrasound imaging (FIG. 25B). No changes were observed in JTA thickness over the 3-week observation period.

After 3-weeks, the patellar tendons were harvested, imaged axially using ultrasound, and prepared for mechanical testing or used for histology. Tendon injury, but not application of the JTA, increased tendon cross sectional area (FIG. 26C). Also, injury decreased tendon echogenicity, indicative of reduced collagen packing or organization (FIG. 25D) (Riggin, C. N., Sarver, J. J., Freedman, B. R., Thomas, S. J. & Soslowsky, L. J. Analysis of Collagen Organization in Mouse Achilles Tendon Using High-Frequency Ultrasound Imaging. *J Biomech Eng, doi:*10.1115/1.4026285 1793821 [pii] (2013)). The JTA improved impaired relaxation of injured tendons (FIG. 25C), but did not affect the elastic tendon mechanics, dynamic modulus (FIG. 25D) and linear modulus of naive and injured tendons. Tendon injury, as expected, impacted these elastic properties of tendon mechanics (FIG. 26D). The toe modulus, percent relaxation, and tan δ were not affected by JTA or injury (FIGS. 26B, E, and F). In agreement with mechanical data, injury, but not JTA implantation, was found to affect the tendon cellularity or shape (FIGS. 25 G and 25H).

Unlike the patellar tendon, the rotator cuff presents additional adhesive attachment challenges, but remains a primary type of tendon injury requiring surgical intervention (Colvin, A. C., Egorova, N., Harrison, A. K., Moskowitz, A. & Flatow, E. L. National trends in rotator cuff repair. *J Bone Joint Surg Am* 94, 227-233, doi:10.2106/JBJS.J.00739 (2012)). For these reasons, a study was performed to investigate the feasibility and biocompatibility of attaching the JTA to the rotator cuff supraspinatus tendon in rats. Because tendon and bone differ greatly in composition, structure, and mechanics, the periosteal surface of bone was first assessed ex vivo for adhesion of the JTA. Mechanical support of the bone-tendon interface (i.e., enthesis) is considered to be critical to support healing of rotator cuff tendon injury (FIGS. 27A and 27B). An in vivo study was next conducted in a rat rotator cuff (Soslowsky, L. J., Carpenter, J. E., DeBano, C. M., Banerji, I. & Moalli, M. R. Development and use of an animal model for investigations on rotator cuff disease. *J Shoulder Elbow Surg* 5, 383-392, doi:S1058-2746 (96)80070-X [pii] (1996)) to evaluate adhesion of JTA to the enthesis of both naive and injured supraspinatus tendon following partial tenotomy (FIG. 25J and FIG. 27C). Here, the footprint of the JTA was expanded to cover the enthesis and pass under the acromion for additional structural support. Following implantation, animals were followed longitudinally using magnetic resonance imaging (MRI) to evaluate the anatomical position of the JTA over time and to assess inflammatory tissue response to the JTA (T2-weighted images). MRI analysis confirmed that placement of the JTA was maintained throughout the duration of the study as animals resumed cage activity (FIG. 25J and FIG. 27D). MRI and histology also identified minimal adjacent tissue inflammation following JTA implantation (FIGS. 25F and 25I, and FIGS. 27D and 27E). Histological staining identified a minimal fibrotic capsule (FIG. 27E). Surgery and JTA implantation had a minimal, non-significant impact on the animal body weights (FIG. 28).

Example 14. JTA Enables Unprecedented Drug Loading and Sustained Drug Release in Silico and In Vitro The delivery of the corticosteroid, triamcinolone acetonide (CORT) (Kosiyatrakul, A., Loketkrawee, W. & Luenam, S. Different Dosages of Triamcinolone Acetonide Injection for the Treatment of Trigger Finger and Thumb: A Randomized Controlled Trial. *J Hand Surg Asian Pac Vol* 23, 163-169, doi:10.1142/S2424835518500157 (2018)), was used as a model drug therapeutics to examine drug loading and release from the JTA. First, the impact of the JTA on diffusion of CORT was examined using a Franz cell (FIG. 29A). The JTA substantially slowed diffusion of CORT compared to the supporting membrane only (FIG. 29B). Computational modeling was used to compute the diffusion constant of CORT through the JTA (D=16 $\mu m^2$/s), which was lower than that through a PVDF membrane (D=305 $\mu m^2$/s)(Seki, T. et al. Measurement of diffusion coefficients of parabens and steroids in water and 1-octanol. *Chem Pharm Bull (Tokyo)* 51, 734-736, doi:10.1248/cpb.51.734 (2003)). Next, the tough hydrogels were loaded up to 25000× the solubility limit of CORT (Wang, J. R. et al. Polymorphism of Triamcinolone Acetonide Acetate and Its Implication for the Morphology Stability of the Finished Drug Product. Crystal Growth and Design 17, 9, doi: 10.1021/acs.cgd.7b00453 (2017)) (FIG. 29C). Drug loading was accomplished by adding the CORT microcrystal suspension to the high viscosity alginate acrylamide hydrogel prior to crosslinking. Although the CORT microcrystal are micronized (FIG. 30), they form larger aggregates in the JTA at high loading (size >150 $\mu m^2$) (FIG. 29E, FIGS. 2Q-2S). The addition of CORT, turned the color of the JTA from clear to white (FIG. 30C). Finite element (FE) simulations were next performed to model release of CORT from the JTA under well mixed conditions (FIG. 29D). Notably, the model predicted sequential dissolution of drug particles in turn starting from the periphery, leading to a sustained release (FIGS. 29E-29G). This prediction agreed with experimental observation (FIG. 29H). CORT release under sink conditions (HBSS, 37 C, pH 7.4, replaced daily) in vitro extended for two weeks, in a manner dependent on the initial CORT loading (FIG. 29H). Notably, the JTA loaded with CORT at 4-times the polymer content (500 mg/ml) still maintained unprecedented mechanical and adhesive properties (FIGS. 2I, 2O, and 29I). Regardless of CORT loading, the viability of tendon derived cells exposed to CORT-loaded JTA remained high in vitro (FIG. 3B).

Example 15. JTA Adherent to Tendon Provides Sustained CORT Release In Vivo

To investigate whether CORT-loaded JTA could provide sustained release in vivo studies in the rat model of patellar tendon injury were conducted (FIG. 31A). Quantification of CORT in serum confirmed that the sustained release observed in vitro also occurred through one-week in vivo (FIG. 31B). Next, to maintain the high CORT concentration in the JTA (100 mg/ml) with dissolution controlled release kinetics, however at a reduced total dose of CORT delivered per animal, a JTA was designed that contained a cylinder-shaped core with CORT, flanked and topped by a blank alginate acrylamide hydrogel (FIG. 32A). This depot JTA was also well tolerated in the rat patellar tendon model in vivo (FIGS. 32B and 32C) and HFUS imaging confirmed maintained placement of the two-compartment JTA over time above the patellar tendon (FIG. 31C). The depot JTA itself reduced inflammation, as indicated by the level of vascularity, in early healing, and the delivery of CORT further reduced inflammation at day 3 post-implantation (FIGS. 31D and 31E).

Following two-weeks post injury with and without JTA implantation or CORT delivery, patellar tendons were harvested and evaluated for their morphology, echogenicity, and biomechanical properties (viscoelastic, dynamic, and quasi-static). After two-weeks, injured tendons remained had decreased echogenicity and elevated mechanical relaxation compared to uninjured tendons (FIGS. 31F and 31G). In contrast, patellar tendons receiving JTA or JTA+CORT treatments were not statistically different than uninjured (FIGS. 31F and 31G). As expected, injury decreased the dynamic modulus regardless of treatment type (FIG. 31H).

Example 16. Assessment of Opportunities for Putative Veterinary and Clinical Use In Situ and In Vitro As a step towards translational application to anatomically larger tendons, the versatility of the JTA was next explored in porcine in situ. The JTA adhered strongly to porcine patellar tendon, flexor tendon, and Achilles tendon even in the presence of blood (FIG. 33A). Adhesion was generated rapidly, and the JTA conformed well to tissue surfaces. Maintenance of adhesion was further confirmed after incubation in 1×PBS (37° C., pH 7.4) of excised tendons in vitro as to model in vivo conditions for intrasynovial tendons. Next, the capacity of the JTA to support gliding in human cadaveric wrists was examined in situ when used as a protective barrier over the flexor pollicis longus (FIG. 33B, FIGS. 34A and 34B). Here, the JTA must withstand friction as it glides over the volar plate and also passes through the transverse carpal ligaments. The JTA adhered well to the flexor pollicis longus and withstood gliding over the volar plate into the transverse carpal ligaments.

Discussion

This study engineered and characterized a novel JTA for the treatment and prevention of tendon injury. Although many hydrogel-based materials are used in wound dressings, tissue repair and regeneration, medical implants, transdermal drug delivery, and bioelectronics (Yang, J., Bai, R., Chen, B. & Zuo, S. Hydrogel Adhesion: A Supramolecular Synergy of Chemistry, Topology, and Mechanics. *Advanced Functional Materials,* 27 (2019)), none exhibit appropriate adhesive properties and the broad versatility necessary for tendon applications. In addition to investigate its adhesive properties in vitro, the JTA was tested in multiple tendon models in situ and in vivo, highlighting the broad utility of the material and its potential advantages when used as a mechanical support and delivery system of drug therapeutics.

The JTA interacts well with wet tendon surfaces and exhibits a ~16-fold increase in adhesion energy, as compared to the fibrin glue, TISSEEL®. This strong adhesion may be attributed to the multicomponent adhesion mechanisms and high toughness not present in adhesive hydrogels in clinical use (Li, J. et al., supra). The extremely high toughness of the tough gel plays an integral role in avoiding cohesive failure and dissipating energy at the adhesive interface to ensure strong adhesion to tendon and provide mechanical support. In contrast, naturally derived extracellular matrix (GraftJacket®) and small intestine submucosa (CuffPatch®), and synthetic variants (Artelon®) in clinical use to provide mechanical support for tendon repair, do not adhere strongly to tissue (Freedman and Mooney, supra) (Table 2).

TABLE 2

Comparison of the tough adhesive to existing products

| Product | Material | Adhesion (Jm$^{-2}$) | Drug Delivery |
|---|---|---|---|
| Adhesives | | | |
| JTA | Alginate-PAAM | 800 | Yes |
| TISSEEL ® | Fibrin | 60 | No |
| Grafts | | | |
| GraftJacket ® | Decellularized Skin | 0 | No |
| CuffPatch ® | Small Intestine Submucosa | 0 | No |
| Artelon ® | Urethane urea | 0 | No |

The importance of augmenting tendon gliding following repair has prompted active research, as a common limitation of healing is fibrosis presumably caused by high friction between the healing tendon and surrounding tissues (Zhao, C. et al. CORR(R) ORS Richard A. Brand Award for Outstanding Orthopaedic Research: Engineering flexor tendon repair with lubricant, cells, and cytokines in a canine model. *Clin Orthop Relat Res* 472, 2569-2578, doi:10.1007/s11999-014-3690-y (2014); Zhao, C. et al. Surface modification counteracts adverse effects associated with immobilization after flexor tendon repair. *J Orthop Res* 30, 1940-1944, doi:10.1002/jor.22177 (2012)). Notably, the non-chitosan coated side of the tough adhesive supported gliding at lower friction than normal tendon on tendon. This capacity to promote gliding with surrounding tissue could improve joint range of motion and accelerate return to activity, and will be further examined in future studies. The design of a JTA that exhibit low friction and tunable mechanical properties is likely relevant for other orthopedic applications with tissues requiring gliding, including cartilage, meniscus, and muscle.

Local delivery often requires placement of drug delivery depots (Langer, R. & Folkman, J. Polymers for the sustained release of proteins and other macromolecules. Nature 263, 797-800, doi:10.1038/263797a0 (1976)) near the or sutured to the tissue of interest, but this approach may suffer from depot migration and depot disintegration over time due to dynamic tissue movements (Freedman and Mooney, supra; Markl and Zeitler, supra). The JTA is appealing since its adhesive properties eliminate migration over time and its extremely high toughness makes it resistant to mechanical disintegration due to tissue movement. The adhesive depot system may also enable other drug delivery systems to be easily integrated and stabilized. Further, while many drug depot systems suffer limited loading capacities (0.01-1 mg/ml) and frequently exhibit burst release of a large fraction of the loaded drug (LI and Mooney, supra), the JTA is capable of drug loading over 4-times its polymer content (up to 500 mg/ml), and release over 10 days under perfect sink conditions in vitro and over 1-week in vivo, which is unprecedented for hydrogels. The dissolution-controlled release of the corticosteroid, triamcinolone acetonide, from the JTA examined here suggests that this strategy may be effective for other hydrophobic drug therapeutics as well. While triamcinolone acetonide was used as a model drug, the use of corticosteroids to mitigate pain and inflammation on tendon has been controversial for decades (Hugate, et al., supra; Zhang, et al., supra; Kapetanos, G, The effect of the local corticosteroids on the healing and biomechanical properties of the partially injured tendon. *Clin Orthop Relat Res,* 170-179 (1982); Yang, S. L. et al., Lidocaine potentiates the deleterious effects of triamcinolone acetonide on tenocytes. *Med Sci Monit* 20, 2478-2483, doi:10.12659/MSM.891116 (2014); Blomgran, P. et al., Systemic corticosteroids improve tendon healing when given after the early inflammatory phase. *Sci Rep* 7, 12468, doi:10.1038/s41598-017-12657-0 (2017). Although some studies suggest potentially harmful effects of corticosteroids on tendon health, e.g. decreased tissue viability (Harada, Y. et al. Dose- and time-dependent effects of triamcinolone acetonide on human rotator cuff-derived cells. *Bone Joint Res* 3, 328-334, doi: 10.1302/2046-3758.312.2000321 (2014); Wong, M. W. et al., Triamcinolone suppresses human tenocyte cellular activity and collagen synthesis. *Clin Orthop Relat Res,* 277-281, doi:10.1097/01.blo.0000118184.83983.65 (2004)), increased apoptosis (Harada, et al., supra), loss of fibroblastic appearance (Tempfer, H. et al. Effects of crystalline glucocorticoid triamcinolone acetonide on cultured human supraspinatus tendon cells. *Acta Orthop* 80, 357-362, doi: 10.3109/17453670902988360 (2009)), decreased expression of collagen-I (Tempfer, et al., supra), these studies tend to utilize in vitro tissue culture models with concentrations 20-200× higher than applied in the present study. Lower tendon tissue concentrations may have minor effects (Wang, J. C. et al., supra; Rudnik-Jansen, I. et al. Local controlled release of corticosteroids extends surgically induced joint instability by inhibiting tissue healing. *Br J Pharmacol* 176, 4050-4064, doi:10.1111/bph.14817 (2019)) and related sustained release may improve tendon biomechanics (Blomgran, et al., supra).

An appealing translational feature of the JTAs is that most components are approved for use by the FDA in other devices, and are widely used for other clinical applications.

Alginate, chitosan, and polyacrylamide are used in a number of commercialized products and have undergone extensive animal testing for internal and external indications (Li, J. et al., supra; Darnell, M. C. et al. Performance and biocompatibility of extremely tough alginate/polyacrylamide hydrogels. *Biomaterials* 34, 8042-8048, doi:10.1016/j.biomaterials.2013.06.061 (2013); Blacklow, S. O. et al. Bioinspired mechanically active adhesive dressings to accelerate wound closure. *Sci Adv* 5, eaaw3963, doi:10.1126/sciadv.aaw3963 (2019)). Alginate and chitosan have been used in many wound dressings, e.g. Algisite M™, ChitoFlex, and as systems for protein delivery, e.g. Emdogain (Smucker, J. D. & Fredericks, D. C. Assessment of Progenix((R)) DBM putty bone substitute in a rabbit posterolateral fusion model. *Iowa Orthop J*32, 54-60 (2012); Heijl, L., Heden, G., Svardstrom, G. & Ostgren, A. Enamel matrix derivative (EMDOGAIN) in the treatment of intrabony periodontal defects. *J Clin Periodontol* 24, 705-714, doi:10.1111/j.1600-051x.1997.tb00253.x (1997); Lee, K. Y. & Mooney, D. J. Alginate: properties and biomedical applications. *Prog Polym Sci* 37, 106-126, doi:10.1016/j.progpolymsci.2011.06.003 (2012)), and polyacrylamide, e.g. Bulkamid®, is used as a filler material in treatment of urinary incontinence (Lose, G., Mouritsen, L. & Nielsen, J. B. A new bulking agent (polyacrylamide hydrogel) for treating stress urinary incontinence in women. *BJU Int* 98, 100-104, doi:10.1111/j.1464-410X.2006.06205.x (2006); Kasi, A. D., Pergialiotis, V., Perrea, D. N., Khunda, A. & Doumouchtsis, S. K. Polyacrylamide hydrogel (Bulkamid (R)) for stress urinary incontinence in women: a systematic review of the literature. *Int Urogynecol J*27, 367-375, doi: 10.1007/s00192-015-2781-y (2016)). These favorable properties of the materials together with the demonstrated scalability to anatomical sizes to larger tissues position the JTA for further development for clinical applications. Taken together, the design of JTA for the treatment and prevention of tendon injury described here may provide a technology platform enabling many applications, including potential augmentation of sutures, simultaneous promotion of mechanical support and tendon gliding, and local delivery of drug therapeutics.

While a number of embodiments have been described, the scope of this disclosure is to be defined by the appended claims, and not by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. An interpenetrating networks (IPN) hydrogel composition, comprising:
a first polymer network and a second polymer network; and
at least one therapeutic agent, wherein
wherein the first polymer network comprises a first polymer that is covalently crosslinked and the second polymer network comprises a second polymer that is ionically crosslinked; and
wherein the therapeutic agent is released from the IPN hydrogel composition in a sustained manner;
wherein the concentration of the therapeutic agent (the therapeutic agent/hydrogel w/v %) is at least about 2 times, about 4 times, about 8 times, about 16 times, about 25 times, about 50 times, about 100 times, about 200 times, about 500 times, about 1000 times, about 2000 times, about 5000 times, about 10000 times, about 20000 times, or about 25000 times greater than the solubility limit of the therapeutic agent; and
wherein the therapeutic agent forms an aggregate suspended in the IPN hydrogel.

2. The interpenetrating networks (IPN) hydrogel composition of claim 1, further comprises a clay material.

3. An adhesive composition, comprising the composition of claim 2 and an adhesive polymer layer attached to the interpenetrating networks (IPN) hydrogel.

4. The composition of claim 3, wherein the adhesive polymer is a high density primary amine polymer and attached to the IPN via a coupling agent.

5. The composition of claim 2, wherein the clay material comprises a plurality of clay particles that aggregate in the second polymer network.

6. The composition of claim 5, wherein the therapeutic agent is encapsulated in the hydrophobic interlayer spaces of the aggregated clay particles and/or adsorbed onto the aggregated clay particles.

7. The composition of claim 2, wherein the clay material is selected from the group consisting of kaolinite, illite, chlorite, vermiculite, smectite, bentonite, sodium smectite, attapulgite, sepiolite, dicite, halloysite, nacrite, and laponite.

8. The composition of claim 2, wherein the composition comprises about 1 mg/ml to about 200 mg/ml of the clay material.

9. The composition of claim 2, wherein the weight ratio of the clay material to the therapeutic agent is from about 100:1 to about 2:5.

10. The composition of claim 1, wherein
(a) the first polymer is selected from the group consisting of polyacrylamide, poly(hydroxyethylmethacrylate) (PHEMA), poly(vinyl alcohol) (PVA), polyethylene glycol (PEG), polyphosphazene, collagen, gelatin, poly (acrylate), poly(methacrylate), poly(methacrylamide), poly(acrylic acid), poly(N-isopropylacrylamide) (PNI-PAM), poly(N,N-dimentylacrylamide), poly(allylamine) and copolymers thereof; and/or
(b) the first polymer network comprises a first polymer that is covalently crosslinked with a covalent cross linking agent selected from the group consisting of N,N-methylenebisacrylamide (MBAA), a methacrylate crosslinker, N,N'-dicyclohexylcarbodiimide (DCC), 1-ethyl-3-(3-dimethylaminopropyl)carbodiimide (ECC), N-hydroxysuccinimide, N-hydroxysulfosuccinimide, glutaraldehyde, and a transglutaminase; and/or
(c) the first polymer network comprises a first polymer that is covalently crosslinked with a biodegradable covalent crosslinking agent selected from the group consisting of a poly(ethylene glycol) acrylate, a gelatin acrylate, a hyaluronic acid acrylate, an alginate acrylate, and poloxamer (PEG-PPG-PEG) diacrylate; and/or
(d) the second polymer is selected from the group consisting of alginate, pectate, carboxymethyl cellulose, oxidized carboxymethyl cellulose, hyaluronate, chitosan, κ-carrageenan, ι-carrageenan and λ-carrageenan, wherein the alginate, carboxymethyl cellulose, hyaluronate chitosan, κ-carrageenan, ι-carrageenan and λ-carrageenan are each optionally oxidized, wherein the alginate, carboxymethyl cellulose, hyaluronate chitosan, κ-carrageenan, ι-carrageenan and λ-carrageenan optionally include one or more groups selected from the group consisting of methacrylate, acrylate, acrylamide, methacrylamide, thiol, hydrazine, tetrazine, norbornene, transcyclooctene and cyclooctyne; and/or (e) the second polymer network comprises a second polymer that is ionically crosslinked with an ionic crosslinking agent selected from the group consisting of $CaCl_2$, $CaSO_4$, $CaCO_3$, hyaluronic acid, and polylysine; and/or (f) the first polymer network and the second polymer network are covalently coupled.

11. A drug delivery system comprising the composition of claim 1 and an additional drug delivery device.

12. An adhesive composition, comprising the composition of claim 1 and an adhesive polymer layer attached to the interpenetrating networks (IPN) hydrogel, wherein the first polymer is polyacrylamide, the second polymer is alginate, and the adhesive polymer is chitosan.

13. The composition of claim 12, wherein the therapeutic agent is a corticosteroid.

14. The composition of claim 13, wherein the concentration of the therapeutic agent (the therapeutic agent/hydrogel w/v %) is at least about 25 times, about 50 times, about 100 times, about 200 times, about 500 times, about 1000 times, about 2000 times, about 5000 times, about 10000 times, about 20000 times, or about 25000 times greater than the solubility limit of the therapeutic agent.

15. The composition of claim 1, wherein the therapeutic agent is selected from the group consisting of a biologic, a small molecule, a metal, or a combination thereof.

16. The composition of claim 1, wherein the therapeutic agent is a corticosteroid.

17. The composition of claim 16, wherein the corticosteroid is triamcinolone or a pharmaceutically acceptable salt thereof.

* * * * *